US012299884B2

(12) United States Patent
Probert et al.

(10) Patent No.: US 12,299,884 B2
(45) Date of Patent: May 13, 2025

(54) MACHINE-LEARNING-ENABLED PREDICTIVE BIOMARKER DISCOVERY AND PATIENT STRATIFICATION USING STANDARD-OF-CARE DATA

(71) Applicant: Insitro, Inc., South San Francisco, CA (US)

(72) Inventors: Christopher Probert, Mill Valley, CA (US); Zachary Ryan McCaw, Chapel Hill, NC (US); Daphne Koller, Portola Valley, CA (US); Anna Shcherbina, San Bruno, CA (US)

(73) Assignee: Insitro, Inc., South San Francisco, CA (US)

( * ) Notice: Subject to any disclaimer, the term of this patent is extended or adjusted under 35 U.S.C. 154(b) by 0 days.

(21) Appl. No.: 18/442,041

(22) Filed: Feb. 14, 2024

(65) Prior Publication Data
US 2024/0273718 A1    Aug. 15, 2024

Related U.S. Application Data

(60) Provisional application No. 63/618,258, filed on Jan. 5, 2024, provisional application No. 63/445,980, filed on Feb. 15, 2023.

(51) Int. Cl.
*G06T 7/00*      (2017.01)
*G06T 11/60*     (2006.01)

(52) U.S. Cl.
CPC .......... *G06T 7/0012* (2013.01); *G06T 11/60* (2013.01); *G06T 2207/10081* (2013.01); *G06T 2207/10088* (2013.01); *G06T 2207/20081* (2013.01)

(58) Field of Classification Search
CPC .......... G06T 7/0012; G06T 11/60; G06T 2207/10081; G06T 2207/10088; G06T 2207/20081
See application file for complete search history.

(56) References Cited

U.S. PATENT DOCUMENTS

| 10,467,754 B1 | 11/2019 | Ando et al. |
| 11,423,256 B2 | 8/2022 | Marie-Nelly et al. |

(Continued)

FOREIGN PATENT DOCUMENTS

| WO | WO-2010082096 A2 | 7/2010 |
| WO | WO-2020113237 A1 | 6/2020 |
| WO | WO-2023023507 A1 | 2/2023 |

OTHER PUBLICATIONS

An et al. NPL "A deep learning model designed for Raman spectroscopy with a novel hyperparameter optimization method" (Year: 2022).*

(Continued)

*Primary Examiner* — Andrew W Bee
*Assistant Examiner* — Winta Gebreslassie
(74) *Attorney, Agent, or Firm* — MORRISON & FOERSTER LLP

(57) ABSTRACT

The present disclosure relates generally to biomarker discovery and patient stratification, and more specifically to machine learning techniques for discovering relevant biomarkers using data collected as part of the standard-of-care (SoC), which can be used to identify a relevant patient population for a therapeutic with a known mechanism of action (MoA). An exemplary method for predicting activity of a molecular analyte of a patient comprises: training a first module of a machine learning model based on a plurality of medical images of a first cohort; training a second module of the machine learning model based on one or more molecular analyte data sets obtained from a second cohort; receiving a medical image from the patient; and predicting, using the trained first and second modules of the machine learning model, the activity of the molecular analyte from the medical image of the patient.

29 Claims, 72 Drawing Sheets
(57 of 72 Drawing Sheet(s) Filed in Color)

(56) References Cited

U.S. PATENT DOCUMENTS

| | | |
|---|---|---|
| 11,875,506 B1 | 1/2024 | Herve et al. |
| 11,978,206 B2 | 5/2024 | Marie-Nelly et al. |
| 12,002,559 B2 | 6/2024 | Casale et al. |
| 2008/0201083 A1 | 8/2008 | Hata et al. |
| 2017/0204359 A1 | 7/2017 | Ando et al. |
| 2019/0295721 A1 | 9/2019 | Madabhushi et al. |
| 2019/0369098 A1* | 12/2019 | Hegde ............... A61K 31/404 |
| 2019/0371471 A1 | 12/2019 | Tan et al. |
| 2020/0005461 A1 | 1/2020 | Yip |
| 2020/0105413 A1* | 4/2020 | Vladimirova ............ G16H 20/30 |
| 2020/0258223 A1 | 8/2020 | Yip et al. |
| 2020/0388287 A1 | 12/2020 | Anushiravani et al. |
| 2021/0172931 A1 | 6/2021 | Larsen et al. |
| 2021/0200989 A1 | 7/2021 | Courtiol et al. |
| 2021/0210205 A1* | 7/2021 | Drake ................. G16B 20/00 |
| 2021/0256699 A1 | 8/2021 | Wainrib et al. |
| 2021/0271847 A1 | 9/2021 | Courtiol et al. |
| 2021/0374553 A1 | 12/2021 | Li et al. |
| 2022/0059240 A1 | 2/2022 | Schaeffer et al. |
| 2022/0261668 A1* | 8/2022 | Stumpe ............... G06F 16/284 |
| 2022/0292674 A1* | 9/2022 | Braman ............... G06T 7/0012 |
| 2022/0367053 A1 | 11/2022 | Mahmood et al. |
| 2023/0026189 A1 | 1/2023 | Kamato et al. |
| 2023/0036156 A1 | 2/2023 | Ho et al. |
| 2023/0142909 A1 | 5/2023 | Zhao |
| 2023/0154627 A1 | 5/2023 | Irving et al. |
| 2023/0245477 A1* | 8/2023 | Rothrock ............ G06V 20/698 382/128 |
| 2023/0360758 A1 | 11/2023 | Casale et al. |
| 2024/0104734 A1 | 3/2024 | Marie-Nelly et al. |
| 2024/0119593 A1 | 4/2024 | Marie-Nelly et al. |
| 2024/0274254 A1 | 8/2024 | Casale et al. |
| 2024/0274255 A1 | 8/2024 | Casale et al. |

OTHER PUBLICATIONS

Amaro et al., (2021). "A Machine Learning Approach Enables Quantitative Measurement of Liver Histology and Disease Monitoring in NASH," Hepatology, 74(1):133-147.

Arslan et al., (2022). "Deep learning can predict multi-omic biomarkers from routine pathology images: A systematic large-scale study," BioRxiv, 477189, 44 pages.

Courtiol et al., (2020). "Classification and Disease Localization in Histopathology Using Only Global Labels: A Weakly-Supervised Approach," arXiv, 1802.02212, 13 pages.

De Jong et al., (2021). "Towards Realizing the Vision of Precision Medicine: AI Based Prediction of Clinical Drug Response Authors," Brain, 144:1738-1750.

Galton, (1886). "Regression Towards Mediocrity in Hereditary Stature," The Journal of the Anthropological Institute of Great Britain and Ireland, 15:246-263.

Goldsborough et al., (2017). "CytoGAN: generative modeling of cell images," BioRxiv, 227645, 6 pages.

Ingale et al., (2023). "Prediction of met overexpression in non-small cell lung adenocarcinomas from hematoxylin and eosin images," arXiv, 2310.07682, 45 pages.

International Search Report and Written Opinion received for International Patent Application No. PCT/US2022/075006 mailed on Jan. 27, 2023, 19 pages.

International Search Report and Written Opinion received for International Patent Application No. PCT/US2022/080200 mailed on May 23, 2023, 20 pages.

Kopf et al., (2021). "Latent representation learning in biology and translational medicine," Patterns, 2(3):100198, 15 pages.

Liu et al., (2018). "An integrated tcga pan-cancer clinical data resource to drive high-quality survival outcome analytics," Cell, 173(2):400-416, 29 pages.

Taylor-Weiner et al., (2021). "A machine learning approach enables quantitative measurement of liver histology and disease monitoring in NASH," Hepatology, 74(1):133-147.

Ubbens et al., (2020). "Latent space phenotyping: automatic image-based phenotyping for treatment studies," Plant Phenomics, 2020:5801869, 13 pages.

Wells et al., (2009). "Phase contrast microscopy analysis of breast tissue: differences in benign vs. malignant epithelium and stroma," Anal Quant Cytol Histol., 31(4):197-207, 18 pages.

Courtiol et al., (2019). "Deep learning-based classification of mesothelioma improves prediction of patient outcome," Nature Medicine, 25(10):1519-1525.

International Search Report and Written Opinion received for International Patent Application No. PCT/US2024/015870 mailed on Jun. 14, 2024, 25 pages.

Li et al., (2021). "Deep learning-based predictive biomarker of pathological complete response to neoadjuvant chemotherapy from histological images in breast cancer," J Transl Med, 19:348, 13 pages.

Chao et al., (2021). "MAPS: machine-assisted phenotype scoring enables rapid functional assessment of genetic variants by high-content microscopy," BMC Bioinformatics, 22:202, 19 pages.

Clark et al., (2011). "Analysis of efficacy and side effects in CATIE demonstrates drug response subgroups and potential for personalized medicine," Schizophrenia Research, 132(2-3):114-120, 15 pages.

Han et al., (2019). "GCN-MF: disease-gene association identification by graph convolutional networks and matrix factorization," Proceedings of the 25th ACM SIGKDD International Conference on Knowledge Discovery & Data Mining, pp. 705-713, 10 pages.

International Search Report and Written Opinion received for International Patent Application No. PCT/US2024/015870 mailed on Aug. 5, 2024, 36 pages.

Li et al., (2015). "Identification of type 2 diabetes subgroups through topological analysis of patient similarity," Science Translational Medicine 7(311):311ra174, 17 pages.

Schulam et al., (2016). "Disease trajectory maps," Advances in Neural Information Processing Systems, 29, 9 pages.

* cited by examiner

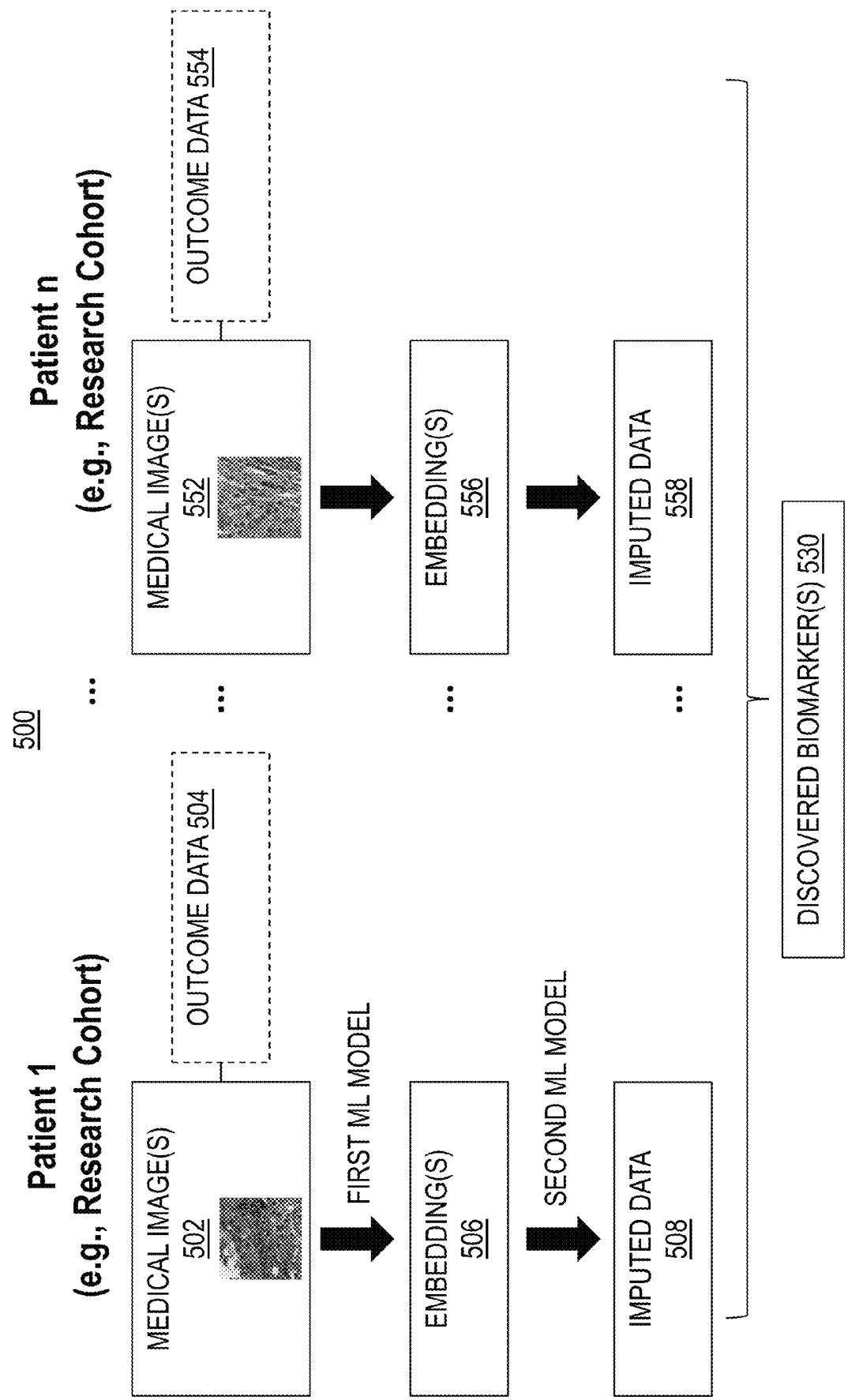

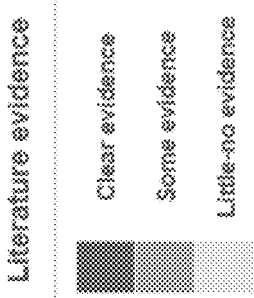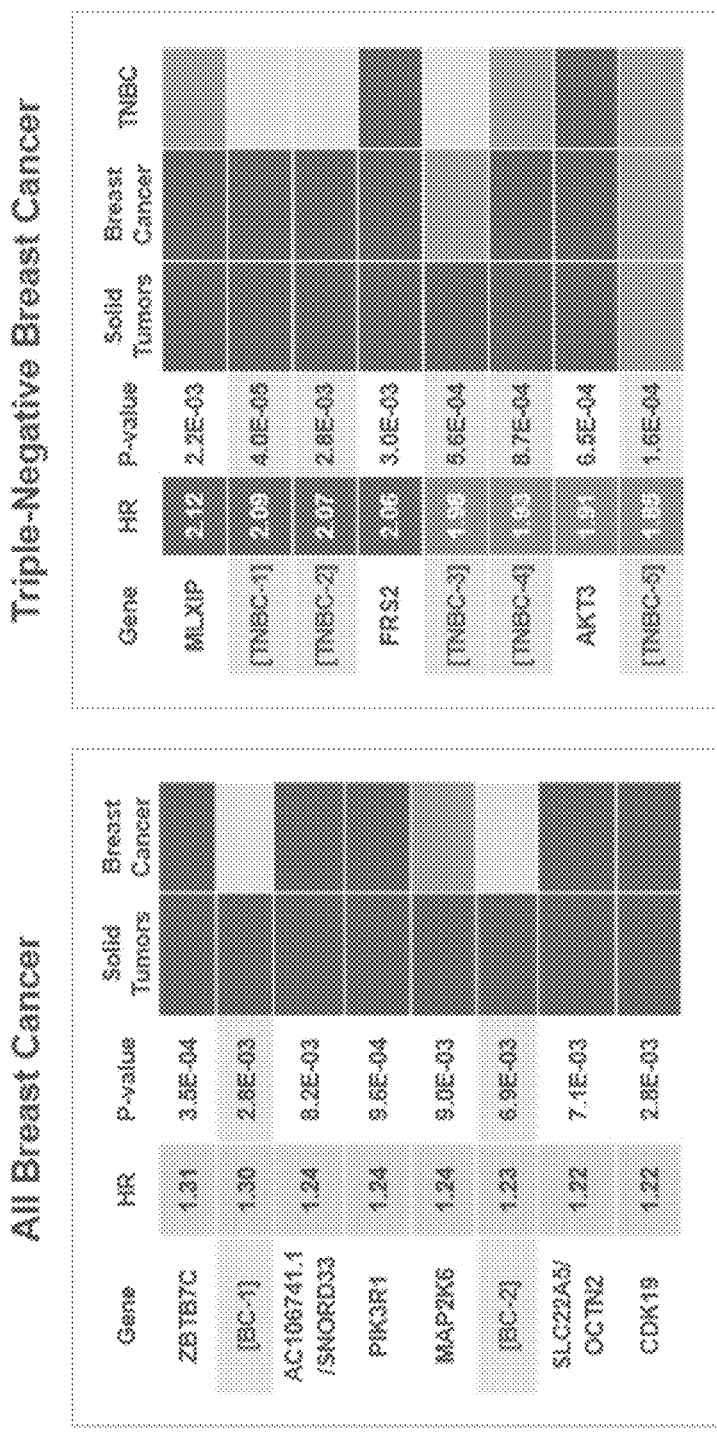
FIG. 8

Embeddings Predict Tumor Genetics
Trained ML model to predict tumor genotype from histology embedding
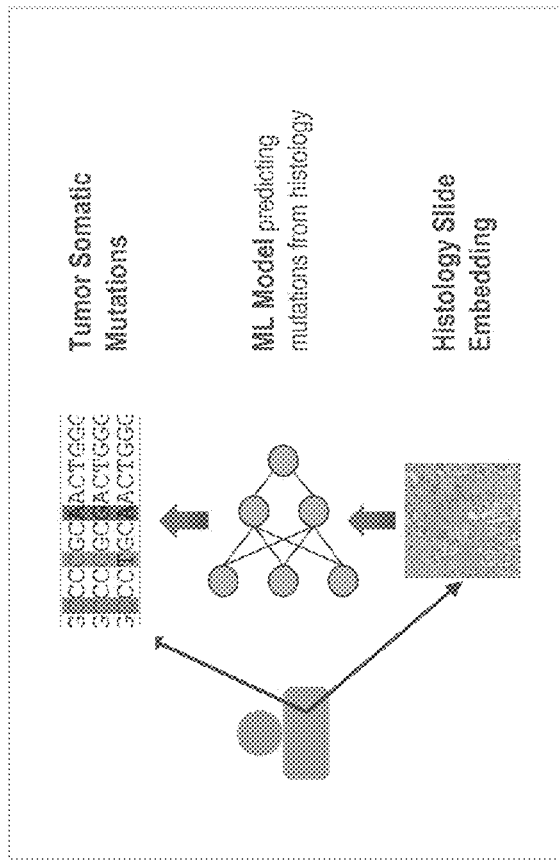
Somatic Mutation Detection in Breast Cancer (N=960 cases)
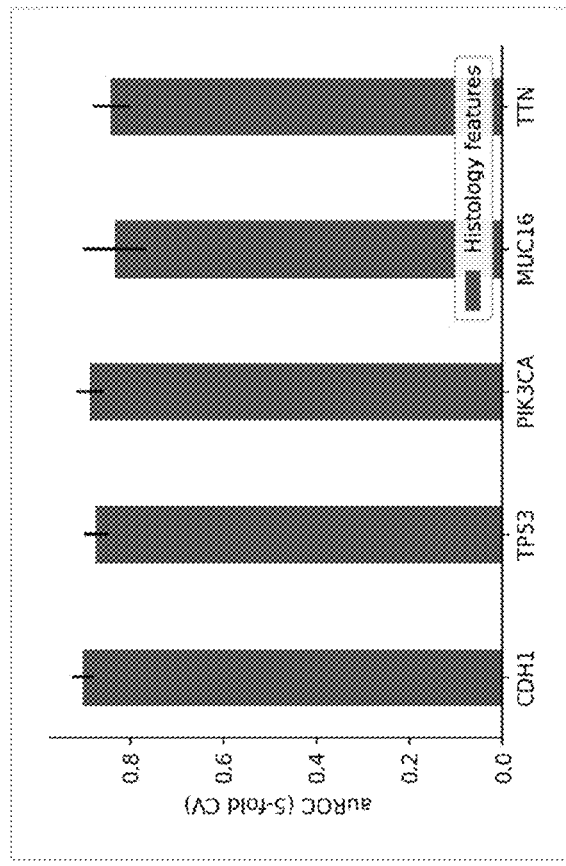
Predictive accuracy on held-out samples is comparable to fully supervised models, underscoring the utility of unsupervised embeddings as a basis for association discovery
FIG. 13

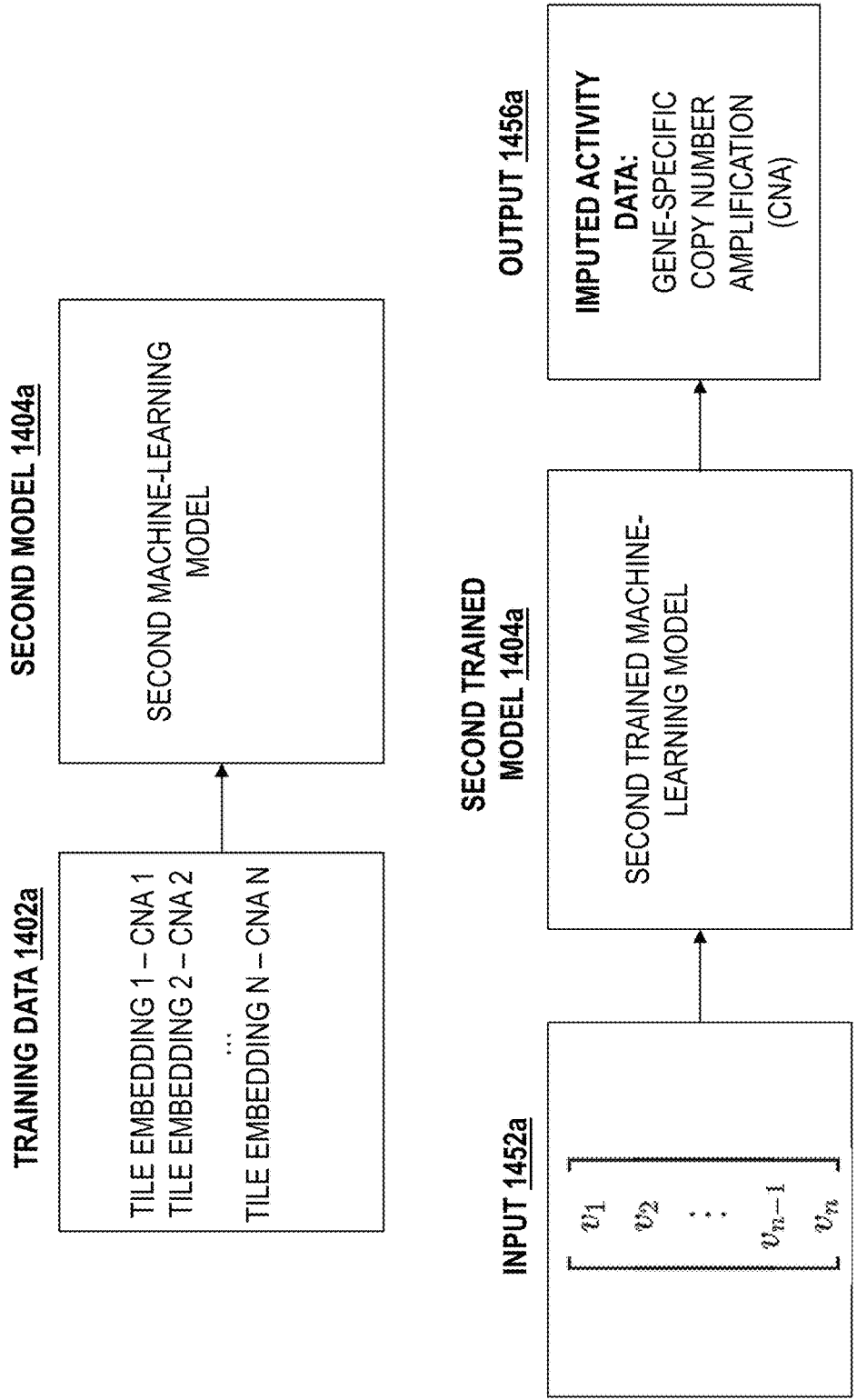

| Patients | Mean Signature | Relative Change |
|---|---|---|
| Cases | 0.549 | +46.3% |
| Controls | 0.375 | |

FIG. 26

| Metric | Min | Median | Mean | Max |
|---|---|---|---|---|
| Pearson $R^2$ | 0.000 | 0.018 | 0.053 | 0.568 |
| Spearman $R^2$ | 0.000 | 0.020 | 0.052 | 0.474 |

FIG. 28

| Biomarker | Cohort | N | N ≥ 0.1 | N ≥ 0.2 | N ≥ 0.3 | N ≥ 0.4 | N ≥ 0.5 |
|---|---|---|---|---|---|---|---|
| CNA | Pan-cancer | 352 | 58 | 18 | 6 | 3 | 1 |
| CNA | Stratified | 352 | 39 | 7 | 0 | 0 | 0 |
| RNA | Pan-cancer | 347 | 347 | 345 | 316 | 221 | 112 |
| RNA | Stratified | 347 | 347 | 230 | 71 | 16 | 0 |
| SIG | Pan-cancer | 351 | 350 | 290 | 218 | 187 | 147 |
| SIG | Stratified | 351 | 335 | 185 | 131 | 92 | 52 |

FIG. 30

| Biomarker | Cohort | N | N ≥ 0.65 | N ≥ 0.75 | N ≥ 0.85 | N ≥ 0.95 |
|---|---|---|---|---|---|---|
| CNA | Pan-cancer | 352 | 334 | 142 | 11 | 0 |
| CNA | Stratified | 352 | 255 | 25 | 0 | 0 |
| RNA | Pan-cancer | 347 | 347 | 339 | 200 | 18 |
| RNA | Stratified | 347 | 311 | 97 | 0 | 0 |
| SIG | Pan-cancer | 351 | 349 | 335 | 246 | 145 |
| SIG | Stratified | 351 | 346 | 201 | 76 | 7 |

FIG. 43

| Metric | Min | Median | Mean | Max |
|---|---|---|---|---|
| Pearson $R^2$ | 0.000 | 0.044 | 0.094 | 0.702 |
| Spearman $R^2$ | 0.000 | 0.045 | 0.090 | 0.671 |

FIG. 52

MACHINE-LEARNING-ENABLED PREDICTIVE BIOMARKER DISCOVERY AND PATIENT STRATIFICATION USING STANDARD-OF-CARE DATA

FIELD OF INVENTION

This application claims the benefit of U.S. Provisional Application 63/445,980 filed on Feb. 15, 2023, and U.S. Provisional Application 63/618,258 filed on Jan. 5, 2024, the entire contents of which are incorporated herein by reference for all purposes.

FIELD OF INVENTION

The present disclosure relates generally to biomarker discovery and patient stratification, and more specifically to machine learning techniques for discovering relevant biomarkers using data collected as part of the standard-of-care (SoC), which can be used to identify a relevant patient population for a therapeutic with a known mechanism of action (MoA).

BACKGROUND

A predictive biomarker can refer to a biomarker used to identify individuals who are more likely than similar individuals without the biomarker to experience a favorable or unfavorable effect from exposure to a medical product or an environmental agent. Generally, clinical programs using predictive biomarkers for patient selection are significantly more likely to be successful. Historically, predictive biomarkers are most often used in oncology (versus other therapeutic areas), because of the early realization of the heterogeneity of the disease and the ability to stratify patients using data that are increasingly collected as part of the SoC. Predictive biomarkers in oncology are usually based on specific somatic alterations measured via targeted gene panels, broader genetic changes such as tumor mutational burden (TMB) or microsatellite instability (MSI), changes in certain key proteins (e.g., ER or HER2), typically measured via IHC, and much less common, gene expression changes or signatures.

However, the promise of precision oncology has not, as of yet, come to full fruition. One important challenge is that the identification of a new biomarker of patient response often relies on results from small clinical trials, which can be underpowered for robust discovery. This biomarker discovery process also requires that the relevant assays are run as part of the clinical trials, often without knowing in advance which assays are likely to be informative on a predictive biomarker. Further, signatures of response that rely on biological measurements that are not currently collected as part of the SoC (e.g., gene expression data) can be hard to ascertain robustly (e.g., via a CLIA-certified process) and are also slow to obtain broad adoption.

Thus, it is desirable to provide techniques for discovering relevant biomarkers using data collected as part of the standard-of-care (SoC), which may lack important biological measurements typically required to power such discovery. The relevant biomarkers can be used for various downstream tasks, such as patient stratification, clinical trial design, and treatment recommendation.

BRIEF SUMMARY

An exemplary system for predicting activity of a molecular analyte of a patient comprises: one or more processors; a memory; and one or more programs, wherein the one or more programs are stored in the memory and configured to be executed by the one or more processors, the one or more programs including instructions for: training a first module of a machine learning model based on a plurality of medical images of a first cohort, wherein the first module comprises an embedding module; training a second module of the machine learning model based on one or more molecular analyte data sets obtained from a second cohort, wherein the second module comprises one or more heads; receiving a medical image from the patient; and predicting, using the trained first and second modules of the machine learning model, the activity of the molecular analyte from the medical image of the patient. In the present disclosure, any machine-learning model may be replaced by a module of a machine-learning model, optionally with one or more heads. Each machine-learning model or module of a machine-learning model can comprise a backbone and a head, which can include the final layer or set of layers in the model (e.g., a neural network).

In some embodiments, the one or more programs further include instructions for: determining if the patient belongs to one or more subgroups based on the predicted activity of the molecular analyte.

In some embodiments, the one or more programs further include instructions for: training a third module of the machine learning model based on a third cohort, the third cohort comprising a plurality of medical images and associated clinical outcomes, wherein the third module of the machine learning model is configured to predict a therapeutic and/or clinical outcome.

In some embodiments, the one or more programs further include instructions for: using the third machine learning model to determine a measure of significance or prognostic value of the molecular analyte to dynamically select a subset of molecular analytes for subsequent use.

In some embodiments, the second module of the machine learning model and/or the third module of the machine learning model are trained using transfer learning.

In some embodiments, the one or more molecular analyte data sets comprises: gene expression data; copy number amplification (CNA) data; amplification signature data; chromatin accessibility data; DNA methylation data; histone modification; RNA data; protein data; spatial biology data; whole-genome sequencing (WGS) data; somatic mutation data; germline mutation data; or any combination thereof.

In some embodiments, the one or more molecular analyte data sets comprise: a gene expression value comprising an abundance of a transcript; copy number amplification (CNA) data; amplification signature data; a chromosome accessibility score comprising an ATAC-seq peak value; abundance of one or more histone modifications comprising a ChIP-seq value; abundance of one or more mRNA sequences; abundance of one or more proteins; the presence of one or more somatic mutations; the presence of one or more germline mutations; the presence or absence of one or more specific DNA methylation marks in one or more specific genomic regions, or any combination thereof.

In some embodiments, the one or more molecular analyte data sets comprise two molecular analyte data sets.

In some embodiments, the medical image from the patient is obtained from a fourth cohort comprising a plurality of medical images of a plurality of patients and optionally one or more associated molecular analyte data sets for each of the plurality of medical images.

In some embodiments, the one or more programs further include instructions for determining for each of the patients of the fourth cohort that the patient belongs to one or more subgroups.

In some embodiments, the first cohort comprises a plurality of medical images from a plurality of patients.

In some embodiments, the plurality of medical images comprises: one or more histopathology images; one or more magnetic resonance imaging (MRI) images; one or more computerized tomography (CT) scans; or any combination thereof.

In some embodiments, the plurality of medical images are unlabeled and the first module is trained using unsupervised learning.

In some embodiments, the first cohort and second cohort are the same cohort.

In some embodiments, the second cohort comprises a plurality of medical images and data of one or more associated molecular analytes.

In some embodiments, the third cohort comprises a plurality of medical images and associated clinical outcomes.

In some embodiments, the first, second or third cohort further comprise one or more clinical covariates.

In some embodiments, the one or more clinical covariates comprise patient gender, patient age, height, weight, patient diagnosis, patient histology data, patient radiology data, patient medical history, or any combination thereof.

In some embodiments, the one or more programs further include instructions for removing data-specific biases in the first, second, and third cohort.

In some embodiments, the one or more programs further include instructions for: receiving a medical image of a new patient; obtaining an embedding by providing the medical image of the new patient to the first module; mapping the embedding based on domain adaptation.

In some embodiments, the molecular analyte is a first molecular analyte, and the one or more programs further include instructions for: training a fourth module of the machine learning model based on the second module using transfer learning, wherein the fourth module is configured to predict a second molecular analyte related to the first molecular analyte.

In some embodiments, the one or more programs further comprise instructions for: calculating a continuous score.

In some embodiments, training the second module of the machine learning model comprises: in a first stage, training a generalized module based on training data from the one or more molecular analyte data sets obtained from the second cohort; and in a second stage, finetuning the generalized module based on a subset of the training data to obtain the second module.

In some embodiments, the subset of training data corresponds to a patient attribute.

In some embodiments, the patient attribute comprises a patient cohort, a disease, a biomarker, or any combination thereof.

In some embodiments, the patient has the patient attribute.

In some embodiments, the first module of the machine learning model is trained to generate tile-level embeddings based on a plurality of tiles of the medical image, and wherein the tile-level embeddings are input into the second module of the machine learning model.

In some embodiments, at least a subset of the tile level embeddings are averaged prior to being input into the second module of the machine learning model.

In some embodiments, the second module of the machine learning model comprises an attention mechanism.

In some embodiments, the one or more programs further include instructions for: generating an annotation map of the predicted activity of the molecular analyte; and overlaying the annotation map on the medical image.

In some embodiments, the annotation map comprises a visualization distinguishing normal tissue from tumor tissue.

An exemplary method for predicting activity of a molecular analyte of a patient comprises: training a first module of a machine learning model based on a plurality of medical images of a first cohort, wherein the first module comprises an embedding module; training a second module of the machine learning model based on one or more molecular analyte data sets obtained from a second cohort, wherein the second module comprises one or more heads; receiving a medical image from the patient; and predicting, using the trained first and second modules of the machine learning model, the activity of the molecular analyte from the medical image of the patient.

An exemplary non-transitory computer-readable storage medium stores one or more programs for predicting activity of a molecular analyte of a patient, the one or more programs comprising instructions, which when executed by one or more processors of an electronic device, cause the electronic device to perform: training a first module of a machine learning model based on a plurality of medical images of a first cohort, wherein the first module comprises an embedding module; training a second module of the machine learning model based on one or more molecular analyte data sets obtained from a second cohort, wherein the second module comprises one or more heads; receiving a medical image from the patient; and predicting, using the trained first and second modules of the machine learning model, the activity of the molecular analyte from the medical image of the patient.

An exemplary system for predicting activity of a molecular analyte of a patient comprises: one or more processors; a memory; and one or more programs, wherein the one or more programs are stored in the memory and configured to be executed by the one or more processors, the one or more programs including instructions for: training a first machine learning model on a plurality of medical images from a first cohort; training a second machine learning model on embeddings obtained from the first machine learning model and on one or more molecular analyte data sets obtained from a second cohort; receiving a medical image from the patient; and predicting, using the second trained machine learning model, the activity of the molecular analyte from the medical image of the patient.

In some embodiments, the one or more programs further include instructions for: determining if the patient belongs to one or more subgroups based on the predicted activity of the molecular analyte.

In some embodiments, the one or more programs further include instructions for: training a third machine learning model based on a third cohort, the third cohort comprising a plurality of medical images and associated clinical outcomes, wherein the third machine learning model is configured to predict a therapeutic and/or clinical outcome.

In some embodiments, the one or more programs further include instructions for: using the third machine learning model to calculate a measure of significance or prognostic value of the molecular analyte to dynamically select a subset of molecular analytes for subsequent use.

In some embodiments, the second machine learning model and/or the third machine learning model are trained using transfer learning.

In some embodiments, the one or more molecular analyte data sets comprises: gene expression data; copy number amplification (CNA) data; amplification signature data; chromatin accessibility data; DNA methylation data; histone modification; RNA data; protein data; spatial biology data; whole-genome sequencing (WGS) data; somatic mutation data; germline mutation data; or any combination thereof.

In some embodiments, the one or more molecular analyte data sets comprise: a gene expression value comprising an abundance of a transcript; copy number amplification (CNA) data; amplification signature data; a chromosome accessibility score comprising an ATAC-seq peak value; abundance of one or more histone modifications comprising a ChIP-seq value; abundance of one or more mRNA sequences; abundance of one or more proteins; the presence of one or more somatic mutations; the presence of one or more germline mutations; the presence or absence of one or more specific DNA methylation marks in one or more specific genomic regions, or any combination thereof.

In some embodiments, the one or more molecular analyte data sets comprise two molecular analyte data sets.

In some embodiments, the medical image from the patient is obtained from a fourth cohort comprising a plurality of medical images of a plurality of patients and optionally one or more associated molecular analyte data sets for each of the plurality of medical images.

In some embodiments, the one or more programs further include instructions for determining for each of the patients of the fourth cohort that the patient belongs to one or more subgroups.

In some embodiments, the first cohort comprises a plurality of medical images from a plurality of patients.

In some embodiments, the plurality of medical images comprises: one or more histopathology images; one or more magnetic resonance imaging (MRI) images; one or more computerized tomography (CT) scans; or any combination thereof.

In some embodiments, the plurality of medical images are unlabeled and the first machine learning model is trained using unsupervised learning.

In some embodiments, the first cohort and second cohort are the same cohort.

In some embodiments, the second cohort comprises a plurality of medical images and data of one or more associated molecular analytes.

In some embodiments, the third cohort comprises a plurality of medical images and associated clinical outcomes.

In some embodiments the first, second or third cohort further comprise one or more clinical covariates.

In some embodiments, the one or more clinical covariates comprise patient gender, patient age, height, weight, patient diagnosis, patient histology data, patient radiology data, patient medical history, or any combination thereof.

In some embodiments, the one or more programs further include instructions for removing data-specific biases in the first, second, and third cohort.

In some embodiments, the one or more programs further include instructions for: receiving a medical image of a new patient; obtaining an embedding by providing the medical image of the new patient to the first machine learning model; mapping the embedding based on domain adaptation.

In some embodiments, the molecular analyte is a first molecular analyte, and the one or more programs further include instructions for: training a fourth machine learning model based on the second machine learning model using transfer learning, wherein the fourth machine learning model is configured to predict a second molecular analyte related to the first molecular analyte.

In some embodiments, the one or more programs further comprise instructions for: calculating a continuous score.

In some embodiments, training the second module of the machine learning model comprises: in a first stage, training a generalized module based on training data from the one or more molecular analyte data sets obtained from the second cohort; and in a second stage, finetuning the generalized module based on a subset of the training data to obtain the second module.

In some embodiments, the subset of training data corresponds to a patient attribute.

In some embodiments, the patient attribute comprises a patient cohort, a disease, a biomarker, or any combination thereof.

In some embodiments, the patient has the patient attribute.

In some embodiments, the first module of the machine learning model is trained to generate tile-level embeddings based on a plurality of tiles of the medical image, and wherein the tile-level embeddings are input into the second module of the machine learning model.

In some embodiments, at least a subset of the tile level embeddings are averaged prior to being input into the second module of the machine learning model.

In some embodiments, the second module of the machine learning model comprises an attention mechanism.

In some embodiments, the one or more programs further include instructions for: generating an annotation map of the predicted activity of the molecular analyte; and overlaying the annotation map on the medical image.

In some embodiments, the annotation map comprises a visualization distinguishing normal tissue from tumor tissue.

An exemplary method for predicting activity of a molecular analyte of a patient comprises: training a first machine learning model on a plurality of medical images from a first cohort; training a second machine learning model on embeddings obtained from the first machine learning model and on one or more molecular analyte data sets obtained from a second cohort; receiving a medical image from the patient; and predicting, using the second trained machine learning model, the activity of the molecular analyte from the medical image of the patient.

An exemplary non-transitory computer-readable storage medium stores one or more programs for predicting activity of a molecular analyte of a patient, the one or more programs comprising instructions, which when executed by one or more processors of an electronic device, cause the electronic device to perform: training a first machine learning model on a plurality of medical images from a first cohort; training a second machine learning model on embeddings obtained from the first machine learning model and on one or more molecular analyte data sets obtained from a second cohort; receiving a medical image from the patient; and predicting, using the second trained machine learning model, the activity of the molecular analyte from the medical image of the patient. An exemplary system for stratifying patients comprises: one or more processors; a memory; and one or more programs, wherein the one or more programs are stored in the memory and configured to be executed by the one or more processors, the one or more programs including instructions for: receiving a first plurality of medical images of a first cohort; determining a plurality of embeddings by providing the first plurality of images to a first trained machine learning model; training a second machine learning model to predict one or more molecular analytes by providing the second machine learning model with the plurality of embeddings from the first machine learning model and activity data of the one or more molecular analytes of the first cohort; predicting imputed activity data of the one or more molecular analytes of a second cohort by providing the trained second machine learning model with a second plurality of medical images of the second cohort; identifying one or more relevant biomarkers based on the imputed activity data of the second cohort and outcome data of the second cohort; receiving one or more medical images of a patient; determining if the patient belongs to one or more patient subgroups based on presence of the one or more relevant biomarkers.

In some embodiments, the first cohort is smaller than the second cohort.

In some embodiments, the activity data of the one or more molecular analytes of the first cohort and/or the imputed activity data of the second cohort comprise: gene expression data; copy number amplification (CNA) data; amplification signature data; chromatin accessibility data; DNA methylation data; histone modification; RNA data; protein data; spatial biology data; whole-genome sequencing (WGS) data; somatic mutation data; germline mutation data; or any combination thereof.

In some embodiments, the activity data of the one or more molecular analytes of the first cohort and/or the imputed activity data of the second cohort comprise: a gene expression value comprising an abundance of a transcript; copy number amplification (CNA) data; amplification signature data; a chromosome accessibility score comprising an ATAC-seq peak value; abundance of one or more histone modifications comprising a ChIP-seq value; abundance of one or more mRNA sequences; abundance of one or more proteins; the presence of one or more somatic mutations; the presence of one or more germline mutations; the presence or absence of one or more specific DNA methylation marks in one or more specific genomic regions, or any combination thereof.

In some embodiments, the first plurality of images of the first cohort and/or the second plurality of images of the second cohort comprises: one or more histopathology images; one or more magnetic resonance imaging (MRI) images; one or more computerized tomography (CT) scans; or any combination thereof.

In some embodiments, data associated with the second cohort is collected as part of the standard-of-care (SoC).

In some embodiments, data associated with the second cohort comprises The Cancer Genome Atlas (TCGA) data.

In some embodiments, the first trained machine learning model comprises an unsupervised model or a self-supervised model.

In some embodiments, the first trained machine learning model comprises a contrastive model.

In some embodiments, the second machine learning model is a linear model.

In some embodiments, the imputed activity data is related to an ATAC-seq peak.

In some embodiments, identifying the one or more relevant biomarkers comprises: determining, using a third machine learning model, an association of the imputed activity data of the second cohort and outcome data of the second cohort.

In some embodiments, determining the association comprises: training, using the imputed activity data and the outcome data of the second cohort, the third machine learning model configured to predict an outcome based on activity data of a molecular analyte; determining a correlation metric indicative of a degree of correlation between the activity data of the molecular analyte and clinical outcome.

In some embodiments, the correlation metric comprises: a p-value associated with the third machine learning model.

In some embodiments, the one or more biomarkers comprises a machine learning-based biomarker or an image-based biomarker.

In some embodiments, determining if the patient belongs to the one or more patient subgroups comprises: determining one or more embeddings by providing the one or more images of the patient to the first machine learning model; determining imputed activity data associated with the patient by providing the one or more embeddings to the trained machine learning model; and determining if the imputed activity data associated with the patient indicates the presence of the one or more biomarkers.

In some embodiments, the one or more programs further include instructions for: identifying a treatment for the patient based on the one or more biomarkers and known mechanism of action (MoA) of the treatment.

In some embodiments, the outcome data is indicative of mortality, disease diagnosis, disease progression, disease prognosis, disease risk, or any combination thereof, and wherein patient stratification is based on one or more of mortality, disease diagnosis, disease progression, disease prognosis, disease risk, or any combination thereof.

In some embodiments, the one or more programs further comprising instructions for: calculating a continuous score.

In some embodiments, training the second module of the machine learning model comprises: in a first stage, training a generalized module based on training data from the one or more molecular analyte data sets obtained from the second cohort; and in a second stage, finetuning the generalized module based on a subset of the training data to obtain the second module.

In some embodiments, the subset of training data corresponds to a patient attribute.

In some embodiments, the patient attribute comprises a patient cohort, a disease, a biomarker, or any combination thereof.

In some embodiments, the patient has the patient attribute.

In some embodiments, the first module of the machine learning model is trained to generate tile-level embeddings based on a plurality of tiles of the medical image, and wherein the tile-level embeddings are input into the second module of the machine learning model.

In some embodiments, at least a subset of the tile level embeddings are averaged prior to being input into the second module of the machine learning model.

In some embodiments, the second module of the machine learning model comprises an attention mechanism.

In some embodiments, the one or more programs further include instructions for: generating an annotation map of the predicted activity of the molecular analyte; and overlaying the annotation map on the medical image.

In some embodiments, the annotation map comprises a visualization distinguishing normal tissue from tumor tissue.

An exemplary method for stratifying patients comprises: receiving a first plurality of medical images of a first cohort; determining a plurality of embeddings by providing the first plurality of images to a first trained machine learning model; training a second machine learning model to predict one or more molecular analytes by providing the second machine learning model with the plurality of embeddings from the first machine learning model and activity data of the one or more molecular analytes of the first cohort; predicting imputed activity data of the one or more molecular analytes of a second cohort by providing the trained second machine learning model with a second plurality of medical images of the second cohort; identifying one or more relevant biomarkers based on the imputed activity data of the second cohort and outcome data of the second cohort; receiving one or more medical images of a patient; determining if the patient belongs to one or more patient subgroups based on presence of the one or more relevant biomarkers.

An exemplary non-transitory computer-readable storage medium stores one or more programs for predicting activity of a molecular analyte of a patient, the one or more programs comprising instructions, which when executed by one or more processors of an electronic device, cause the electronic device to perform: receiving a first plurality of medical images of a first cohort; determining a plurality of embeddings by providing the first plurality of images to a first trained machine learning model; training a second machine learning model to predict one or more molecular analytes by providing the second machine learning model with the plurality of embeddings from the first machine learning model and activity data of the one or more molecular analytes of the first cohort; predicting imputed activity data of the one or more molecular analytes of a second cohort by providing the trained second machine learning model with a second plurality of medical images of the second cohort; identifying one or more relevant biomarkers based on the imputed activity data of the second cohort and outcome data of the second cohort; receiving one or more medical images of a patient; determining if the patient belongs to one or more patient subgroups based on presence of the one or more relevant biomarkers.

DESCRIPTION OF THE FIGURES

The patent or application file contains at least one drawing executed in color. Copies of this patent or patent application publication with color drawing(s) will be provided by the Office upon request and payment of the necessary fee.

FIG. 5 illustrates an exemplary process for using the trained first machine learning model and the trained second machine learning model to identify one or more relevant biomarkers, in accordance with some embodiments.

FIG. 8 illustrates how imputed ATAC-seq signal helps identify novel outcome-associated genes, in accordance with some embodiments.

FIG. 13 illustrates an exemplary system's ability to predict somatic mutations from the embeddings in accordance with some embodiments.

FIG. 14A illustrates the training and use of the second machine learning model for directly predicting copy number amplification in accordance with some embodiments.

FIG. 26 illustrates mean signature scores in patients with (cases) and without (controls) amplifications in accordance with some embodiments.

FIG. 28 illustrates squared correlation between the amplification signature and expression of the amplified gene, pan-cancer in accordance with some embodiments.

FIG. 30 summarizes biomarker counts exceeding various cutoffs in accordance with some embodiments.

FIG. 43 illustrates a count of genes with AUROC exceeding a given threshold in accordance with some embodiments.

FIG. 52 illustrates squared correlation between the amplification signature and expression of the amplified gene, stratified in accordance with some embodiments.

DETAILED DESCRIPTION

Figure 1A:
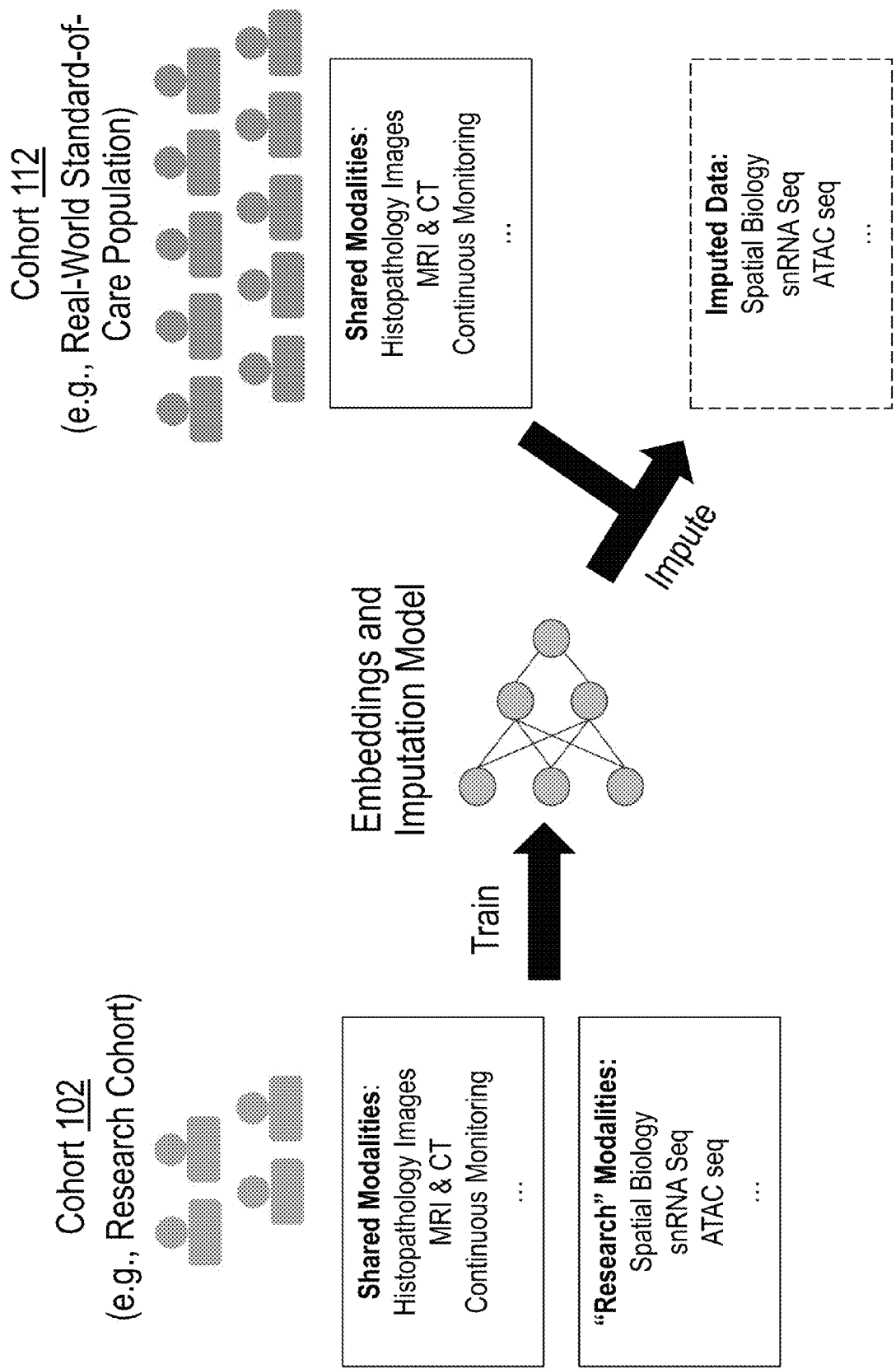
FIG. 1A illustrates an exemplary platform for leveraging machine learning techniques to bridge the gap between research biological data and real-world biological data, in accordance with some embodiments.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Disclosed herein are exemplary devices, apparatuses, systems, methods, and non-transitory storage media using an artificial intelligence (AI) platform for discovering relevant biomarkers and stratifying patients. Embodiments of the present disclosure can bridge the gap between richly profiled but small-scale research cohort(s) and larger-scale real-world cohort(s) for whom data is collected as part of the SoC, allowing discovery of novel clinical insights using SoC data despite its missingness. To do so, the system leverages the shared data modalities between the two cohorts, such as histopathology data (e.g., from H&E biopsy or Trichrome samples), MRI data, CT scans, X-ray, and continuous monitoring data, which are data types collected for both cohorts. The system can use data from the research cohorts to train an imputation model. The imputation model can receive embedding data of a subject (e.g., histopathology embeddings) and predict molecular analyte activity data of the subject. The trained imputation model can be applied to process data from the SoC cohort to obtain imputed molecular analyte activity data for the SoC cohorts to uncover novel clinical insights, such as identifying relevant biomarkers, performing patient stratification, identifying patients for clinical trials, and identifying treatments based on their known MoA, as discussed herein.

In some embodiments, the system can train a first machine learning model (or a first module of a machine learning model), such as a self-supervised or unsupervised model, that is configured to receive input data of a modality shared across cohorts and output embedding data. The embedding data is a numerical, low-dimensional featurization of the input data that can power downstream analyses. The system can then train a second machine learning mode (or a second module of the machine learning model) that is configured to receive embedding data of a given patient and output predicted activity data of one or more molecular analytes for the patient. Importantly, the second machine learning model can be trained using data from the research cohort, as molecular analyte activity data is available for the research cohort. Once trained, the second machine learning model can be used to obtain imputed molecular analyte activity data for the larger SoC cohort, for which molecular analyte activity data was never collected. Accordingly, the second machine learning model allows imputation of research modalities from SoC modalities at scale and can learn fine-grain phenotypes. In some embodiments, the first machine learning model and the second machine learning model may be implemented as a first module (i.e., the embedding module) and a second module (i.e., the imputation module) of a machine learning model.

The imputed activity data, coupled with the original data collected for the SoC cohort (e.g., longitudinal clinical outcome data), can be used to uncover novel clinical insights such as discovering relevant biomarkers (e.g., a machine learning-based biomarker, an image-based biomarker) to improve clinical development and utilize human genetics to identify high-confidence therapeutic targets. The relevant biomarkers may include a biological process that is highly associated with (ideally causal of) patient outcome or treatment response and can be modulated using an existing therapeutic intervention whose MoA directly targets that biological process. Further, the relevant biomarkers can be accurately and robustly predicted, using machine learning methods (e.g., first and second machine learning models), from data measured as part of the SoC. An exemplary relevant biomarker may be aberrant activation of a given gene that drives tumor proliferation, where there is a therapeutic that inhibits that gene, and where the activation of that gene is detectable (e.g., to machine learning methods) from histopathology images. Another exemplary relevant biomarker may be the infiltration (or lack thereof) of particular types of cells into the tumor microenvironment (TME), and the intervention might be the modulation of a particular cell migration signaling protein.

In some embodiments, the shared data modality comprises histopathology images. Given the almost universal extent to which H&E images are collected and the information richness of that data modality, histopathology images allow the system to discover robust, H&E-based predictive biomarkers for patient selection for a range of targeted cancer therapies. The discovered biomarkers may be more precise than broad patient demographics, providing a higher effect size for that targeted patient population, and more inclusive than patient selection based solely on somatic mutations, since it would also encompass other processes that converge on the same biology (e.g. phenocopies). Exemplary biomarkers disclosed herein include ATAC-based biomarkers, which provide hazard ratios (HRs) that are considerably higher than other risk stratification biomarkers, and also higher than what can be obtained from copy number alteration (CNA) based patient selection.

While some embodiments of the present disclosure are directed to imputation of ATAC peaks (and hence genomic activation) from H&E, the same approach can be applied more broadly to other molecular readouts and other shared data modalities. For example, abundance of RNA, bulk proteomics, spatial biology or other data modalities may be measured. The system can also impute readouts not only from H&E, but also histopathology images augment with IHC and/or genetics (both of which are rapidly becoming the SoC for many cancer types). One critical aspect is that MoAs of (at least some) therapeutic interventions can be mapped directly to readouts in those imputed assays, in the same way that an MoA inhibiting a driver gene aligns with an ATAC readout showing that this gene is activated. For example, the system may use imputed spatial biology, RNA, or proteomics to identify a patient population in which the infiltration of a particular cell type into the TME is associated with a poor prognosis, and align that with an MoA of modulating cell trafficking or with an MoA of depleting the relevant cell type.

Accordingly, embodiments of the present disclosure provide oncology discovery driven by multimodal clinical data. Exemplary systems can leverage unsupervised machine-learned histology phenotypes (e.g., embeddings) that capture rich, multi-scale tumor microenvironment structure, machine learning techniques (e.g., second machine learning model or imputation model) to impute clinical and genomic outcomes that provide additional layers of information, and data-driven assessment of the impact of genetic and genomic changes on clinical outcomes to uncover novel targets and biomarkers. Exemplary system can uncover novel targets and biomarkers leveraging techniques described herein.

The following description sets forth exemplary methods, parameters, and the like. It should be recognized, however, that such description is not intended as a limitation on the scope of the present disclosure but is instead provided as a description of exemplary embodiments.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1A illustrates an exemplary platform for leveraging machine learning techniques to bridge the gap between research biological data and real-world biological data, in accordance with some embodiments. FIG. 1A depicts two groups of subjects or patients: a cohort 102 and a cohort 112. Cohort 102 may be a relatively small cohort that is organized to collect rich biological information that may require dedicated equipment and setups, often for research purposes. In contrast, cohort 112 may be a larger group of patients for whom data is collected in real-world standard-of-care (SoC) settings. For example, cohort 112 may include data collected from patients as part of receiving medical care and treatments. As discussed below, the data collected for cohort 102 and the data collected for cohort 112 may have shared modalities, but also differ in many aspects.

With reference to FIG. 1A, the data collected for cohort 102 and the data collected for cohort 112 may have shared modalities. Share modalities refer to the types of data that are collected both for cohort 102 (e.g., for research purposes) and cohort 112 (e.g., as part of the SoC). For example, shared modalities may include histopathology images, magnetic resonance imaging (MRI) images, computerized tomography (CT) scans, continuous monitoring data (e.g., EEG, EKG, continuous glucose monitoring, activity monitoring via accelerometers), etc.

The data collected for cohort 102 and the data collected for cohort 112 also differ in many aspects. For example, the data collected for cohort 102 (e.g., a research cohort) may include rich, high-dimensional molecular content that may require dedicated equipment and setups, such as high-content assays. For example, the data may comprise gene expression data, a copy number amplification value (e.g., from WGS, WGBS or targeted sequencing), an amplification signature value (e.g., RNA-seq), chromatin accessibility data (e.g., ATAC-seq), DNA methylation data (e.g., WGBS, RRBS), histone modification data (e.g., histone ChIP-seq), RNA data (e.g., from RNA-seq), protein data, spatial biology data, whole-genome sequencing (WGS) data (e.g., GWAS), somatic mutation data (e.g., sequence data), germline mutation data (e.g., sequence data), or any combination thereof.

In some embodiments, the data may specifically comprise: a gene expression value comprising an abundance of a transcript, a chromosome accessibility score comprising an ATAC-seq peak value, abundance of one or more histone modifications comprising a ChIP-seq value, abundance of one or more mRNA sequences, abundance of one or more proteins, the presence of one or more somatic mutations, the presence of one or more germline mutations, or any combination thereof.

However, the data collected for cohort 102 may be smaller in scale and thus insufficient to power robust biomarker discovery. The data collected for cohort 102 may lack clinical outcome data altogether. One exemplary data collected for cohort 102, but not for cohort 112, may be ATAC-seq (Assay for Transposase-Accessible Chromatin using sequencing) data. ATAC-seq data includes molecular measurements that can provide important insights. ATAC-seq measurements measure chromatin accessibility, i.e., "activity" for genome segments. ATAC-seq data can reveal lowly-expressed driver genes, non-coding driver mutations, and/or epigenetic mechanisms of therapy resistance. ATAC-seq is generally highly sensitive to sample quality and is not used clinically, but rather is only available in limited-scale research datasets. In other words, ATAC-seq data is not collected for cohort 112 as part of the SoC. Thus, ATAC-seq data is collected on a smaller scale and may lack representations from a variety of diseases.

In contrast, the data collected for cohort 112 is larger-scale, often with longitudinal observations, because it is collected as part of the SoC. Further, the data can include high-density modalities that are generated across diverse disease contexts and include phenotypic content usually not fit for the purposes of R&D. In some embodiments, the data collected for cohort 112 can include imaging data, molecular data, genetics data, and outcome data (e.g., mortality, disease diagnosis, disease progression, disease prognosis, disease risk, or any combination thereof, and patient stratification is based on one or more of mortality, disease diagnosis, disease progression, disease prognosis, disease risk, etc.). One exemplary data set associated with the cohort 112 may be data from The Cancer Genome Atlas (TCGA) Program. The TCGA Program started in 2006 and involves over 20,000 tumor and normal samples and 33 cancer types. The TCGA data is diverse but sporadically collected, including genetics data, histopathology images and other images, molecular covariates, clinical outcomes, etc.

Embodiments of the present disclosure can bridge the gap between richly profiled but small-scale research cohorts (e.g., cohort 102 in FIG. 1A) and larger-scale real-world patients (e.g., cohort 112 in FIG. 1A) for whom data is collected as part of the SoC, allowing discovery of novel clinical insights using SoC data despite its missingness. To do so, the system leverages the shared data modalities between the two cohorts, such as histopathology data (e.g., from H&E or Trichrome biopsy samples), MRI data, CT scans, X-ray, and continuous monitoring data, which are data types collected for both cohorts. First, the system can train a first machine learning model (or a first module of a machine learning model), such as a self-supervised or unsupervised model, that is configured to receive input data of a shared modality and output embedding data. The embedding data is a numerical, low-dimensional featurization of the input data that can power downstream analyses. Second, the system can train a second machine learning model (or a second module of a machine learning model) that is configured to receive embedding data of a given patient and output predicted activity data of one or more molecular analytes for the patient. Importantly, the second machine learning model can be trained using data from the research cohort only, as molecular analyte activity data is available for the research cohort. Once trained, the second machine learning model can be used to obtain imputed molecular analyte activity data for the larger SoC cohort, for which molecular analyte activity data was never collected. Accordingly, the second machine learning model allows imputation of one or more research modalities from SoC modalities at scale and can learn fine-grain phenotypes.

Figure 1B:
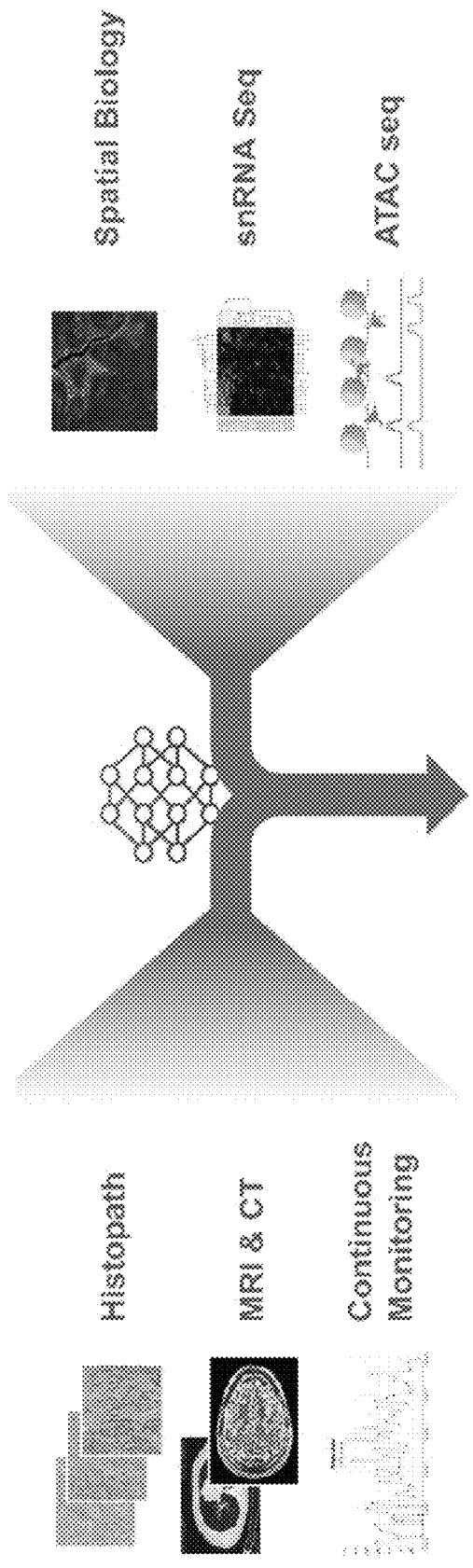
FIG. 1B illustrates an exemplary process for leveraging machine learning techniques to bridge the gap between research biological data and real-world biological data, in accordance with some embodiments.

The imputed activity data, coupled with the original data collected for the SoC cohort (e.g., longitudinal clinical outcome data), can be used to uncover novel clinical insights such as discovering relevant biomarkers (e.g., a machine learning-based biomarker, an image-based biomarker) to improve clinical development and utilize human genetics to identify high-confidence targets, as illustrated in FIG. 1B. The relevant biomarkers may include a biological process that is highly associated with (ideally causal of) patient outcome or treatment response and can be modulated using an existing therapeutic intervention whose MoA directly targets that biology. Further, the relevant biomarkers can be accurately and robustly predicted, using machine learning methods (e.g., first and second machine learning models), from data measured as part of the SoC. An exemplary relevant biomarker may be an aberrant activation of a given gene that drives tumor proliferation, where there is a therapeutic that inhibits that gene, and where the activation of that gene is visible (e.g., to machine learning methods) from histopathology images. Another exemplary relevant biomarker may be the infiltration (or lack thereof) of particular types of cells into the tumor microenvironment (TME), and the intervention might be the modulation of a particular cell migration signaling protein. FIG. 13 illustrates an exemplary system's ability to predict somatic mutations from the embeddings. As shown, a machine learning model is trained to predict tumor genotype from histology embeddings. The predictive accuracy of the machine learning model, which may be a linear model, is comparable to fully supervised models configured to receive and process histology data.

In some embodiments, the shared data modality comprises histopathology images. Given the almost universal extent to which H&E images are collected and the information richness of that data modality, histopathology images allow the system to discover robust, H&E-based predictive biomarkers for patient selection for a range of targeted cancer therapies. The discovered biomarkers may be more precise than broad patient demographics, providing a higher effect size for that targeted patient population, and more inclusive than patient selection based solely on somatic mutations, since it would also encompass other processes that converge on the same biology. Exemplary biomarkers disclosed herein include ATAC-based biomarkers, which provide hazard ratios (HRs) that are considerably higher than other risk stratification biomarkers, and also higher than what can be obtained from copy number alteration (CNA) based patient selection.

While some embodiments of the present disclosure are directed to imputation of ATAC peaks (and hence genomic activation) from H&E, the same approach can be applied more broadly to other shared data modalities. For example, bulk proteomics or spatial biology may be measured. The system can also impute readouts not only from H&E, but also augment with IHC and/or genetics (both of which are rapidly becoming the SoC for many cancer types). One critical aspect is that MoAs of (at least some) therapeutic interventions can be mapped directly to readouts in those imputed assays, in the same way that an MoA inhibiting a driver gene aligns with an ATAC readout showing that this gene is activated. For example, the system may use imputed spatial biology to identify a patient population in which the infiltration of a particular cell type into the TME is associated with a poor prognosis, and align that with an MoA of modulating cell trafficking or with an MoA of depleting the relevant cell type.

Accordingly, embodiments of the present disclosure provide oncology discovery driven by multimodal clinical data.

Exemplary systems can leverage unsupervised or self-supervised machine-learned histology phenotypes (e.g., embeddings) that capture rich, multi-scale tumor microenvironment structure, machine learning techniques (e.g., second machine learning model or imputation model) to impute clinical and genomic covariates that provide additional layers of information, and data-driven assessment of impact of genetic and genomic changes on clinical outcomes to uncover novel targets and biomarkers.

In some embodiments, the system can leverage co-embeddings. For example, the system can align embeddings of two different (in some embodiments, related) modalities, using a separate cohort where both are collected as a training set. For example, the system can align embeddings of the ATAC modality and the RNA modality.

In some embodiments, the system can identify a predictive biomarker for a drug within the context of a patient cohort that is defined by demographic correlates or an already known biomarker (e.g., an IHC biomarker). In some embodiments, the system can identify a predictive biomarker for a combination therapy of two or more drugs. In both cases, the MoA of the drug(s) would need to align directly with an imputable molecular analyte, and the drug's biomarker would be trained to the corresponding analyte. However, the ability to assess the efficacy of the biomarker within patient subsets or as part of a combination is enabled by the ability to impute the biomarker across a large patient population. This would allow an "in silico" process whereby a clinical trial design would be selected using a large real world data set.

In some embodiments, the techniques disclosed herein can expand beyond the case where the biomarker is entirely inferred from the drug's putative MoA. The system may use the molecular analytes to pretrain a model, and then fine tune the weights using a limited cohort of patients (e.g., from a Phase 1a or Phase 2 clinical trial) where the drug's clinical outcomes are actually observed. For example, the system may pretrain a neural network to predict ATAC peaks from the histopathology embedding, and then use the embedding layer as input to a machine learning model that is trained to the clinical outcomes. The system can also reduce dimensionality and increase power by focusing on a smaller set of analytes that may associate with the drug outcomes (e.g., based on prior knowledge).

Figure 2A:
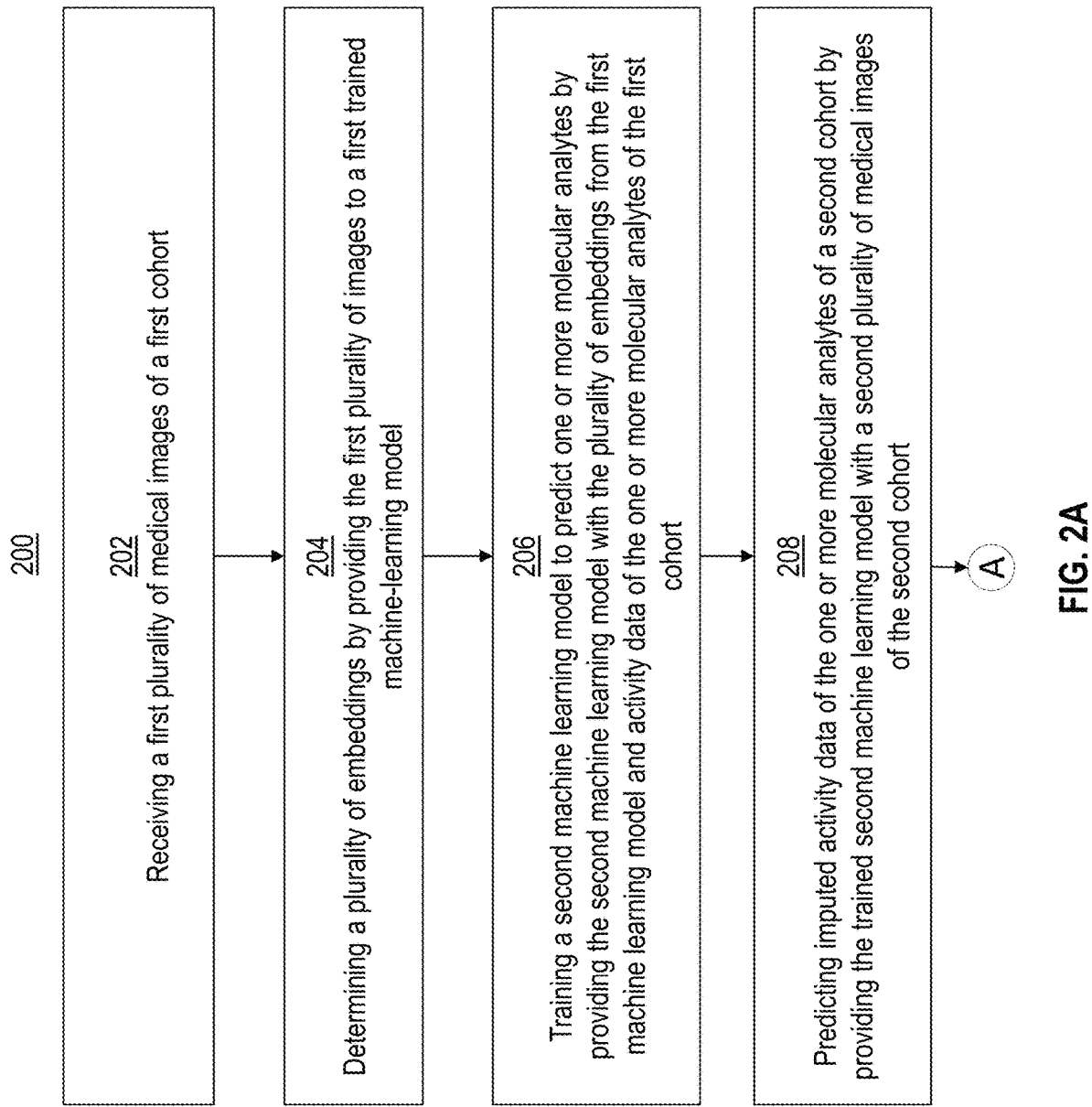
FIG. 2A illustrates an exemplary process for discovering relevant biomarkers and stratifying patients, according to some embodiments.
Figure 2B:
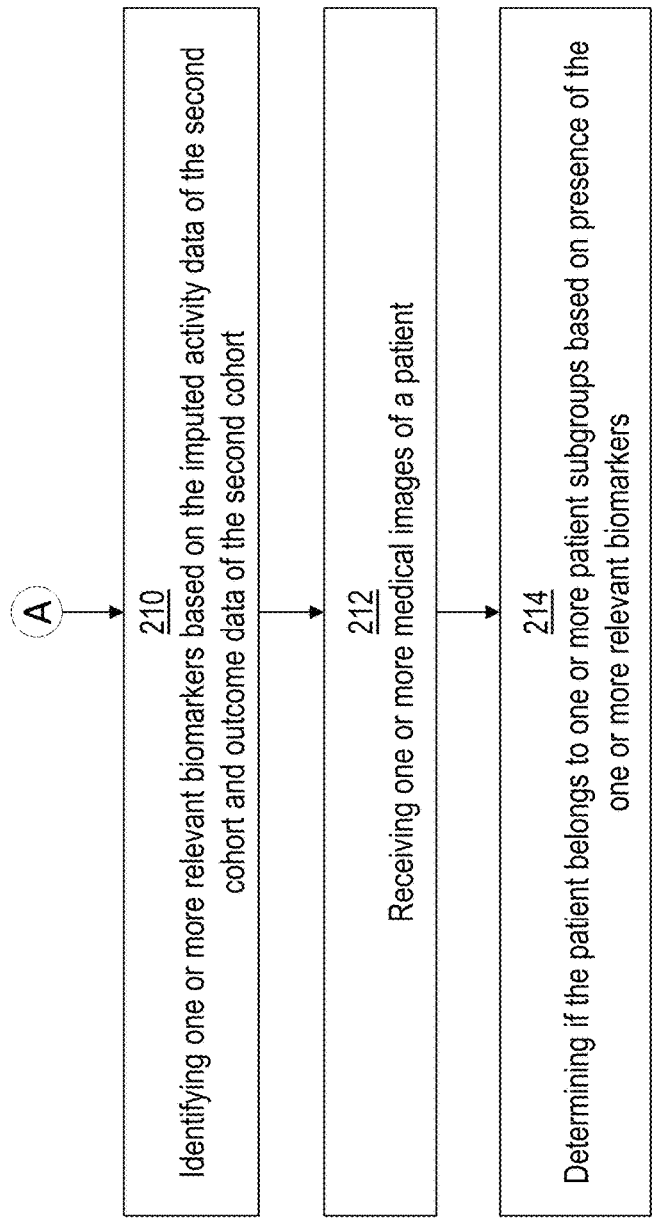
FIG. 2B illustrates an exemplary process for discovering relevant biomarkers and stratifying patients, according to some embodiments.

FIGS. 2A-B illustrate an exemplary process 200 for discovering relevant biomarkers and stratifying patients, according to some embodiments. Process 200 is performed, for example, using one or more electronic devices implementing a software platform. In some examples, process 200 is performed using a client-server system, and the steps of process 200 are divided up in any manner between the server and one or more client devices. In other examples, process 200 is performed using only a client device or only multiple client devices. In process 200, some steps are, optionally, combined, the order of some steps is, optionally, changed, and some steps are, optionally, omitted. In some examples, additional steps may be performed in combination with the process 200. Accordingly, the operations as illustrated (and described in greater detail below) are exemplary by nature and, as such, should not be viewed as limiting.

At block 202, an exemplary system receives a first plurality of medical images of a first cohort. The first cohort may be a small-scale cohort, such as the cohort 102 in FIG. 1A. As discussed above, data collected for the small-scale cohort can include data of shared modalities, such as imaging data. For example, the first plurality of images may comprise one or more histopathology images; one or more magnetic resonance imaging (MRI) images; one or more computerized tomography (CT) scans; or any combination thereof.

Each of the plurality of medical images of the first cohort can have an association with an activity readout of one or more molecular analytes of the first cohort. In other words, data collected for the small-scale cohort can also include high-content modalities where specific MoAs (e.g., activity of specific genes or processes) can be discerned from the data. For example, the activity data of one or more molecular analytes of the first cohort in block 202 may comprise gene expression data, a copy number amplification value (e.g., from WGS, WGBS or targeted sequencing), an amplification signature value (e.g., from RNA-seq), chromatin accessibility data (e.g., ATAC-seq), DNA methylation data (e.g., WGBS, RRBS), histone modification (e.g., histone ChIP-seq), RNA data (e.g., from RNA-seq), protein data, spatial biology data, whole-genome sequencing (WGS) data (e.g., GWAS), somatic mutation data, germline mutation data, or any combination thereof.

In some embodiments, the data may comprise: a gene expression value comprising an abundance of a transcript, a copy number amplification value, an amplification signature value, a chromosome accessibility score comprising an ATAC-seq peak value, abundance of one or more histone modifications comprising a ChIP-seq value, abundance of one or more mRNA sequences, abundance of one or more proteins, the presence of one or more somatic mutations, the presence of one or more germline mutations, the presence or absence of one or more specific DNA methylation marks in one or more specific genomic regions, or any combination thereof.

For example, for a patient in the first cohort, the activity data may comprise a scalar value (e.g., a normalized/log-scaled read count, p-value, or log fold change), or a base-pair level signal (e.g., regressing the ATAC-seq signal shape) corresponding to that patient.

At block 204, the system determines a plurality of embeddings by providing the first plurality of images to a first trained machine learning model. The first machine learning model is configured to receive image data (e.g., a histopathology image or a portion thereof) and output an embedding. An embedding is a numerical, low dimensional featurizations of the input image data. In some embodiments, the first machine learning model comprises an unsupervised model or a self-supervised model. In some embodiments, the first machine learning model comprises a contrastive model such as SimCLR and SwAV. Contrastive learning models can extract embeddings from imaging data, and the embeddings are linearly predictive of biological endpoints or labels (e.g., progression of the disease of interest) that may otherwise be assigned to such data, as described herein. A suitable contrastive learning model is trained such that it can maximize the similarity between embeddings from different augmentations of the same sample image and minimize the similarity between embeddings of different sample images. For example, the model can extract embeddings from images that are invariant to rotation, flipping, cropping, and color jittering. In some embodiments, the embeddings can be mean-aggregated and/or normalized before being used for downstream analysis. In some embodiments, normalizing the embeddings comprises performing a variance-stabilizing transformation, which may improve their ability to linearly predict biological endpoints of labels. As described herein, normalization can improve the performance of linear predictive models fitted based on the embeddings. In some embodiments, a linear model fitted with normalized embeddings has similar or superior predictive capability as a supervised machine-learning model and is more computationally efficient to generate and apply, as described further herein. The training and use of the first machine learning model are provided in detail with reference to FIGS. 3A and 3B.

At block 206, the system trains a second machine learning model to predict one or more molecular analytes by providing the second machine learning model with the plurality of embeddings from the first machine learning model and activity data of the one or more molecular analytes of the first cohort. Specifically, the system has, for each patient in the first cohort, one or more embeddings corresponding to the patient's image data, which are obtained from block 204, as well as the molecular analyte activity data of the patient. Such data can be used as a training dataset for the second machine learning model. Using this training dataset, the second machine learning model can be trained to receive embedding data of a given patient and predict molecular analyte activity data for that given patient. The training and use of the second machine learning model are provided in detail with reference to FIGS. 4A and 4B.

In some embodiments, the second machine learning model is a linear model. For example, the second machine learning model may be a linear model that is configured to receive one or more embeddings of a given patient and predict molecular analyte activity data related to ATAC-seq peaks for that given patient. For example, the predicted activity data may comprise a scalar value (e.g., a normalized/log-scaled read count, p-value, or LogFC), or a base-pair level signal (e.g., regressing the ATAC-seq signal shape). It should be appreciated that the second machine learning model may be other types of models can be trained using training data.

In some embodiments, the second machine learning model can be trained using transfer learning. For example, the system can first train the second model to predict per-gene activity using one modality (e.g., RNA-seq), and then fine-tune (i.e., "transfer") the model to predict a related modality instead (e.g., ATAC-seq). This option would be especially appealing if the cohort with the RNA-seq was larger, but if the ATAC-seq showed stronger correlation with outcome. As another example, if both cohorts have ATAC-seq data, but there are batch effects in one, or one lacks outcome/response data, transfer learning may be used.

At block 208, the system predicts imputed activity data of the one or more molecular analytes of a second cohort by providing the trained second machine learning model with a second plurality of medical images of the second cohort. The second cohort may be larger than the first cohort. In some embodiments, the second cohort can be part of a large-scale cohort such as the cohort 112 in FIG. 1A, for which data such as imaging data, continuous monitoring data, and/or clinical outcome data is collected (e.g., as part of the SoC). In some embodiments, the data collected for the second cohort comprises The Cancer Genome Atlas (TCGA) data.

As discussed above, data collected for the second cohort can have shared modalities as the first cohort. For example, the second plurality of medical images of the second cohort may have the same modalities as the first plurality of medical images of the first cohort and may include one or more histopathology images, one or more magnetic resonance imaging (MRI) images, one or more computerized tomography (CT) scans, or any combination thereof. Further, the data collected for the second cohort has sufficient power to stratify relevant patient outcomes in a given disease (e.g., having enough death or response events). The outcome data can be indicative of mortality, response to treatment, disease diagnosis, disease progression, disease prognosis, disease risk, or any combination thereof, and patient stratification is based on one or more of mortality, disease diagnosis, disease progression, disease prognosis, disease risk, or any combination thereof.

However, as discussed above, data collected for the second cohort may not include rich, high-dimensional molecular content that may require dedicated equipment and setups, such as high-content assays. Using the second machine learning model obtained in blocks 202-206, the system can predict imputed activity data for the second cohort and use such imputed activity data for downstream analysis, as discussed in blocks 210-218.

The system then determines, using the second trained machine learning model, imputed activity data of the one or more molecular analytes of the second cohort. As discussed above, the second machine learning model can be configured to receive embedding data of a given patient and predict molecular analyte activity data for that given patient. Thus, for each patient in the second cohort, the system can receive embedding data of the patient in the second cohort and predict imputed activity data for that patient in the second cohort. The generation of the imputed activity data is described in detail with reference to FIG. 5.

At block 210, the system identifies one or more relevant biomarkers based on the imputed activity data of the second cohort and outcome data of the second cohort. In some embodiments, the system determines, using a third machine learning model, an association of the imputed activity data and clinical outcome data from the second cohort. Specifically, the system can train, using the imputed activity data and the clinical outcome data of the second cohort, the third machine learning model that is configured to predict an outcome based on activity data of a molecular analyte. For example, for each candidate biomarker (i.e., a particular activity of a molecular analyte, a particular molecular analyte), the system can train a candidate-biomarker-specific prediction model configured to receive data related to the candidate biomarker and output a predicted clinical outcome (e.g., response to treatment, time-to-progression, time-to-death).

The candidate-biomarker-specific model is then evaluated to determine whether there is a significant association between the candidate biomarker and the clinical outcome. In some embodiments, the system can determine, based on the model, an association metric or correlation metric indicative of a degree of association or correlation between the candidate biomarker and clinical outcome. An association metric and a correlation metric are used interchangeably in the present disclosure.

For example, the association metric or correlation metric may be a hazard ratio, a risk ratio, or a p-value. In some embodiments, a hazard ratio may be estimated from a Cox proportional hazards model. More generally, the association between a candidate biomarker and a time-to-event outcome (e.g., overall survival, progression-free survival) may be quantified using a (weighted) log-rank test, a Cox proportional hazards model, an Aalen additive hazards model, or a parametric accelerated failure time model.

As another example, the model may be a generalized linear regression model or a time-to-event regression model, and the system can calculate a p-value associating one or more imputed molecular analytes with one or more clinical outcomes. The p-values can be obtained through a standard Wald, score, likelihood ratio, or Monte Carlo testing procedure, and the effect size and standard errors can be obtained through classical generalized linear model theory, in some embodiments. The p-value is indicative of the association between the candidate biomarker and the clinical outcome.

Other association testing procedures can be implemented to determine if there is a significant association between a candidate biomarker and clinical outcome. The association testing procedure can be also based on extensions of generalized linear models such as linear mixed models or generalized estimating equations or on nonlinear models (random forest, SVMs, etc.). Additional information for obtaining histopathology embeddings and conducting association testing can be found in U.S. Provisional Application No. 63/233,707 entitled "DISCOVERY PLATFORM" and PCT Application No. PCT/US2022/075006 entitled "DISCOVERY PLATFORM", the content of which is incorporated herein by reference for all purposes.

The system then identifies one or more relevant biomarkers based on the association. For example, the system can determine whether the p-value corresponding to a candidate biomarker exceeds a predefined threshold to determine if there is a significant association. If the p-value corresponding to the candidate biomarker exceeds the predefined threshold, the system may determine that the candidate biomarker is a relevant biomarker.

In some embodiments, the association metric may indicate a positive association or a negative association. In some embodiments, either a significant (e.g., statistically significant, exceeding a predefined threshold) positive association or a significant negative association may be identified as a relevant biomarker.

At blocks 212 and 214, the system can perform patient stratification based on the biomarkers identified in block 210. For example, a signature (e.g., histopathology signature) that aligns with the predicted MoA defines the "likely responder" patient population. In some embodiments, patient stratification can be based on one or more images of a particular patient. The system can determine if the patient belongs to one or more patient subgroups by determining if the one or more images of the patient indicate an alignment with the determined one or more relevant biomarkers. In addition to a discretized result (one or more discrete subgroups), the system may also return a continuous score to the patient/physician (e.g., level of PD-L1 expression, TMB, HER2 quantification by FISH, etc.).

Specifically, at block 212, the system receives one or more medical images of a patient. The system can provide the one or more images of the patient to the first trained machine learning model to determine one or more embeddings. The system can then provide the one or more embeddings to the second trained machine learning model to determine imputed activity data associated with the patient.

At block 214, the system determines if the patient belongs to one or more patient subgroups based on presence of the one or more relevant biomarkers. Specifically, if the imputed activity data associated with the patient indicates a presence of a relevant biomarker, the system can determine that the patient may belong to a patient subgroup associated with the biomarker.

The system can identify a treatment for the patient based on the one or more biomarkers and known mechanism of action (MoA) of the treatment. An exemplary relevant biomarker may be an aberrant activation of a given gene that drives tumor proliferation, where there is a therapeutic that inhibits that gene, and where the activation of that gene is visible (e.g., to machine learning methods) from histopathology images. Another exemplary relevant biomarker may be the infiltration (or lack thereof) of particular types of cells into the tumor microenvironment (TME), and the intervention might be the modulation of a particular cell migration signaling protein. Another exemplary biomarker might be an aberrant change in the sequence or structure of a protein product (inclusive of a missense variant, a protein truncation, a splice variant, or a fusion of distinct genes), where that change is visible from histopathology images and there is a therapeutic that is targeted selectively at the mutant protein versus the wildtype.

In some embodiments, the system can take a "compound-first" approach to deploy the techniques described herein to accelerate the path to patient impact. The system may first identify a set of targeted therapeutic agents in biopharmaceutical pipelines that have a clear MoA (e.g., a well-defined target) and are potentially cancer modifying. This set may include cancer agents, but can also include agents from other therapeutic areas, such as fibrosis or immunology. The system can then test each of these targets in the set to determine (1) whether the activity of this target can be well imputed from histopathology embeddings and (2) whether the imputed activity is significantly associated with a clinical outcome. If so, the target is identified as a relevant biomarker.

To determine whether the activity of the target can be well imputed from histopathology embeddings, the system can compare the predicted activity data by the second machine learning model and the actual activity data. In some embodiments, the system can determine that the activity is well imputed if the difference between the predicted activity data and the actual activity data does not exceed a predefined threshold. This would require a cohort where the actual activity is measure. In some embodiments, when applying the 2nd machine learning model to a new cohort with a limit set of molecular profiles available, an additional model could be trained to calibrate the outputs 2nd machine learning model to the new cohort.

To determine whether the imputed activity is significantly associated with clinical outcome, the system can determine an association metric between the activity data and clinical outcome. In some embodiments, the association metric can be calculated as described above with reference to FIGS. 2A and 2B. In some embodiments, the association metric comprises a hazard ratio and the system can determine whether the imputed activity provides a significant predicted hazard ratio in some cancer (e.g., is significantly associated with the time-to-progression or death), as discussed above.

The system can then assess whether the relevant biomarker offers an advantage, in terms of identifying patients likely to benefit from therapy, over the biomarkers (if any) currently used in the clinical trial or the clinical setting. For example, it may suggest a new cancer type that has not previously been a target for this therapy, allowing an indication expansion. As another example, the hazard ratio may be considerably higher for a given patient subset, allowing the therapy to be moved earlier in the SoC. As another example, the patient population for the biomarker is considerably larger, enabling a population expansion. As another example, the biomarker currently used requires additional testing that is costly or not always performed, which may be avoided using the proposed system, enabling a population expansion.

Figure 3A:
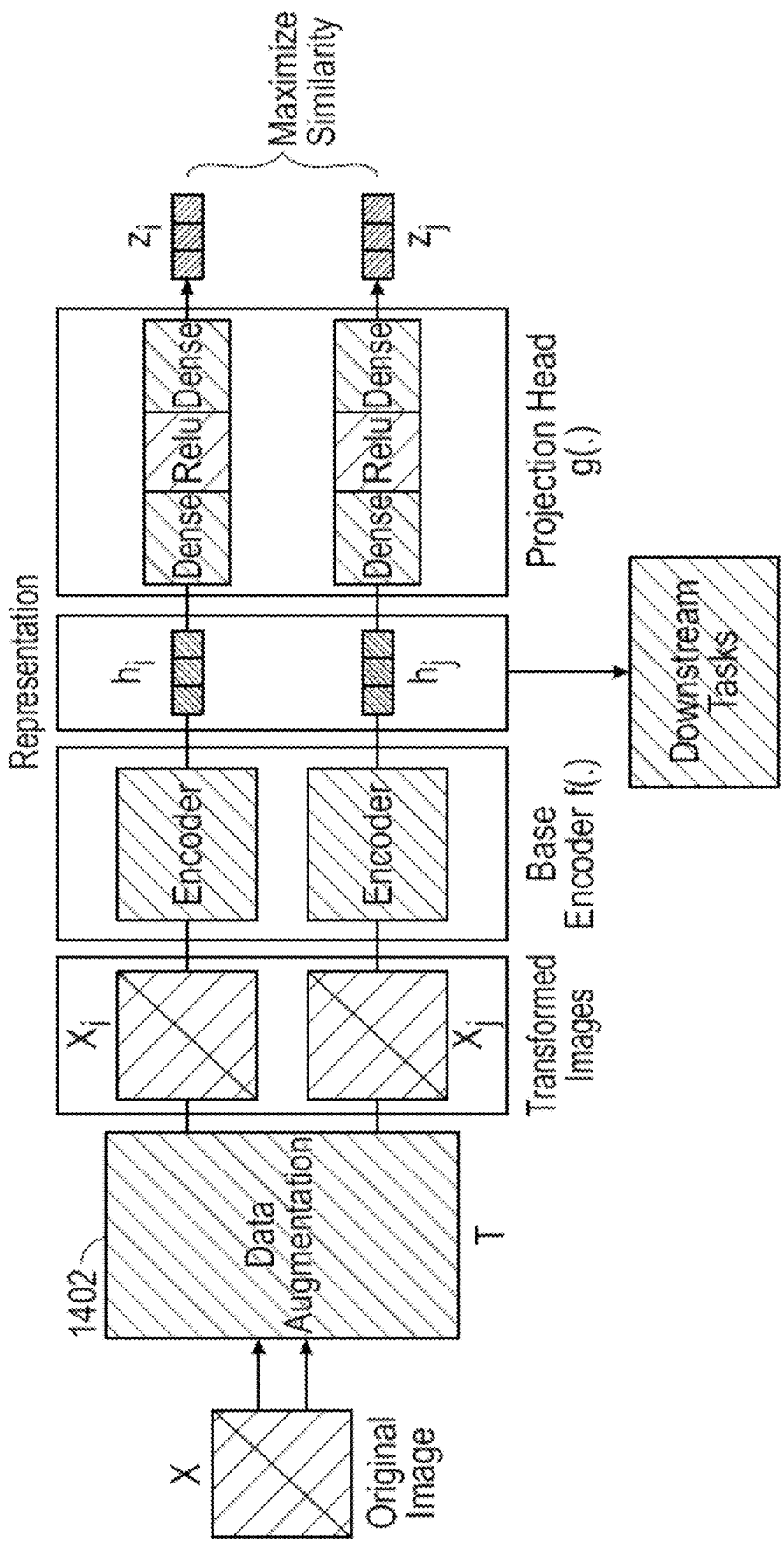
FIG. 3A illustrates the training of an exemplary first machine learning model, in accordance with some embodiments.

FIG. 3A illustrates training of an exemplary first machine learning model, in accordance with some embodiments. In the depicted example, the first machine learning model may be a contrastive learning algorithm and may be one of the encoders in FIG. 3A. In some embodiments, the first machine learning model may be one or more diffusion models. The first machine learning model can be trained using a training dataset associated with a large cohort of subjects with extensive image data. For example, the training dataset can be associated with a large cohort of patients whose histopathology images are collected. The training dataset does not need to include any other covariates, because the training dataset is only used for the purpose of training the first machine learning model to transform image data into embeddings. In some embodiments, this cohort may be neither the cohort 102 nor the cohort 112 in FIG. 1A.

Contrastive learning can refer to a machine learning technique used to learn the general features of a dataset without labels by teaching the model which data points are similar or different. Contrastive learning models can extract embeddings from imaging data that are linearly predictive of labels that might otherwise be assigned to such data. A suitable contrastive learning model is trained by minimizing a contrastive loss, which maximizes the similarity between embeddings from different augmentations of the same sample image and minimizes the similarity between embeddings of different sample images. For example, the model can extract tile embeddings from tile images that are invariant to rotation, flipping, cropping and color jittering. Exemplary contrastive learning models include SimCLR and SwAV, but it should be appreciated that any representation learning algorithm can be used as the first machine learning model.

With reference to FIG. 3A, during training, an original image X is obtained. Data transformation or augmentation can be applied to the original image X to obtain two augmented images $X_i$ and $X_j$. For example, the system can randomly apply two separate data augmentation operators (e.g., crop, flip, color jitter, grayscale, blur) to obtain $X_i$ and $X_j$.

Each of the two augmented images $X_i$ and $X_j$ is passed through an encoder to obtain respective vector representations in a latent space. In the depicted example, the two encoders have shared weights. In some examples, each encoder is implemented as a neural network. For example, an encoder can be implemented using a variant of the residual neural network ("ResNet") architecture. As shown, the two encoders output $h_i$ (vector outputted by the encoder from $X_i$) and $h_j$ (vector outputted by the encoder from $X_j$).

The two vector representations $h_i$ and $h_j$ are passed through a projection head to obtain two projections $z_i$ and $z_j$. In some examples, the projection head comprises a series of non-linear layers (e.g., Dense-Relu-Dense layers) to apply non-linear transformation on the vector representation to obtain the projection. The projection head amplifies the invariant features and maximizes the ability of the network to identify different transformations of the same image.

During training, the similarity between the two different projections $z_i$ and $z_j$ for the same image is maximized. For example, a loss is calculated based on $z_i$ and $z_j$, and the encoder is updated based on the loss to maximize a similarity between the two latent representations. In some examples, to maximize agreement (i.e., similarity) between the z-projections, the system can define the similarity metric as cosine similarity:

$$sim(u, v) = \frac{u^T v}{\|u\| \|v\|}$$

In some examples, the system trains the network by minimizing the normalized temperature-scaled cross-entropy loss:

$$\ell_{i,j} = -\log \frac{\exp(sim(z_i, z_j)/T)}{\sum_{k=1}^{2N} \mathbb{1}_{[k \neq i]} \exp(sim(z_i, z_k)/T)}$$

where π denotes an adjustable temperature parameter. Accordingly, via training, the encoder learns to output a vector representation that preserves the invariant features of the input image while minimizing image-specific characteristics (e.g., imaging angle, resolution, artifacts).

In some embodiments, the embeddings are standardized and then rescaled by the inverse of the square root of the number of embedding dimensions before further processing. The normalization can improve the performance of linear predictive models fitted based on the embeddings, as discussed herein.

Figure 3B:
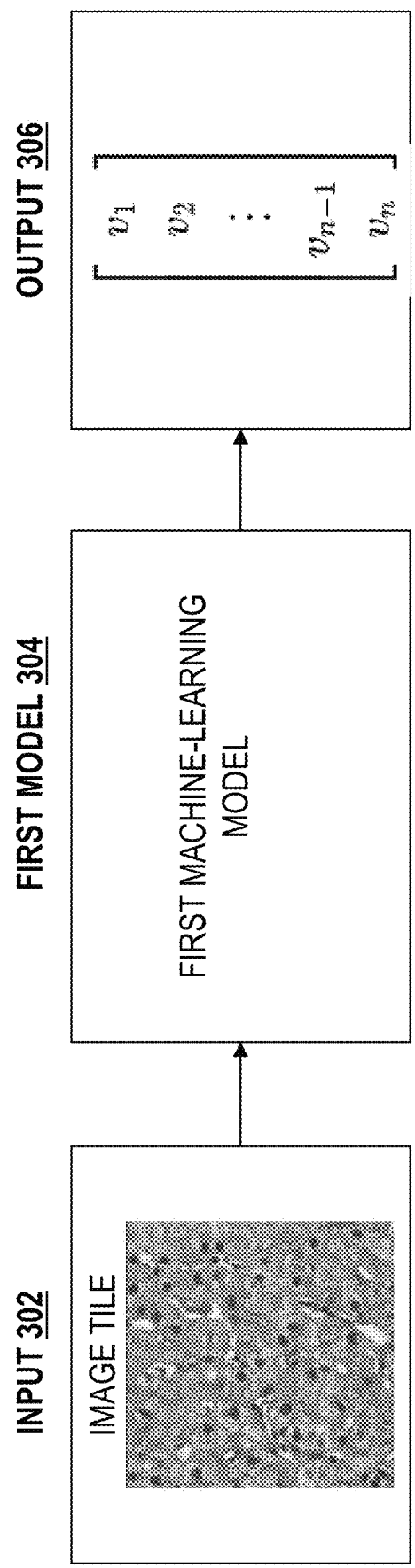
FIG. 3B illustrates the use of an exemplary first machine learning model, in accordance with some embodiments.

FIG. 3B illustrates the use of an exemplary first machine learning model configured to transform image data into embeddings, in accordance with some embodiments. The model 304 can be the first machine learning model used in FIG. 2A. In some embodiments, the model 304 is an unsupervised model or self-supervised model. As shown in FIG. 3B, the machine learning model 304 is configured to receive an input image 302 and provide an output embedding 306. The embedding 306 can be a vector representation of the input image 302 in the latent space. Translating an input image into an embedding can significantly reduce the size and dimension of the original data. In one exemplary implementation, an image sized 224 pixels×224 pixels can be reduced to a 2,048-dimensional vector. The lower-dimension embedding can be used for downstream processing, as described below.

Figure 4A:
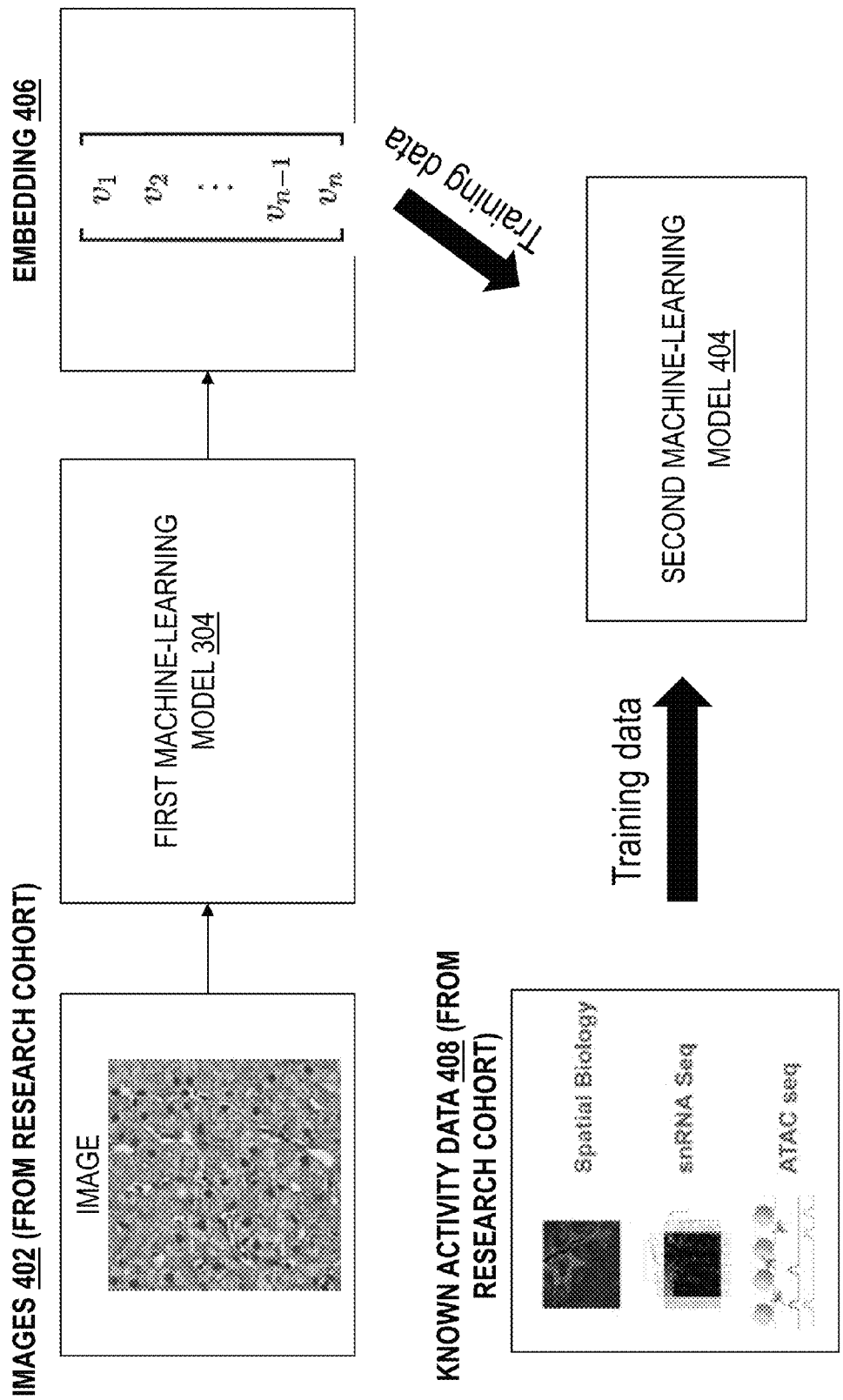
FIG. 4A illustrates the training of an exemplary second machine learning model, in accordance with some embodiments.

FIG. 4A illustrates an exemplary training process of the second machine learning model, in accordance with some embodiments. The training process is an example of blocks 202-206 of FIG. 2A. In the depicted example in FIG. 4A, images from the first cohort are provided to the first machine learning model 304, which outputs embeddings. For example, histopathology image 402 is provided to the first machine learning model 402 to obtain embedding 406, which is a low-dimensional representation of the histopathology image 402. The system also has access to known activity data 408 for the patients in the first cohort. In other words, the system has access to, for each subject in the first cohort, corresponding embedding data and corresponding activity data. Such data can be used as a training dataset to train the second machine learning model 404, which is configured to receive embedding data of a given patient and predict activity data of the patient. In some embodiments, the second machine learning model is a linear model (e.g., one or more penalized linear models). For example, the second machine learning model may be a linear model that is configured to receive one or more embeddings of a given patient and predict molecular analyte activity data related to ATAC-seq peaks for that given patient. For example, the predicted activity data may comprise a scalar value (e.g., a normalized/log-scaled read count, p-value, or LogFC), or a base-pair level signal (e.g., regressing the ATAC-seq signal shape). In some embodiments, the second machine learning model comprises one or more attention-based models (including transformer attention and/or multi-instance attention), one or more diffusion models, or any combination thereof.

Figure 4B:
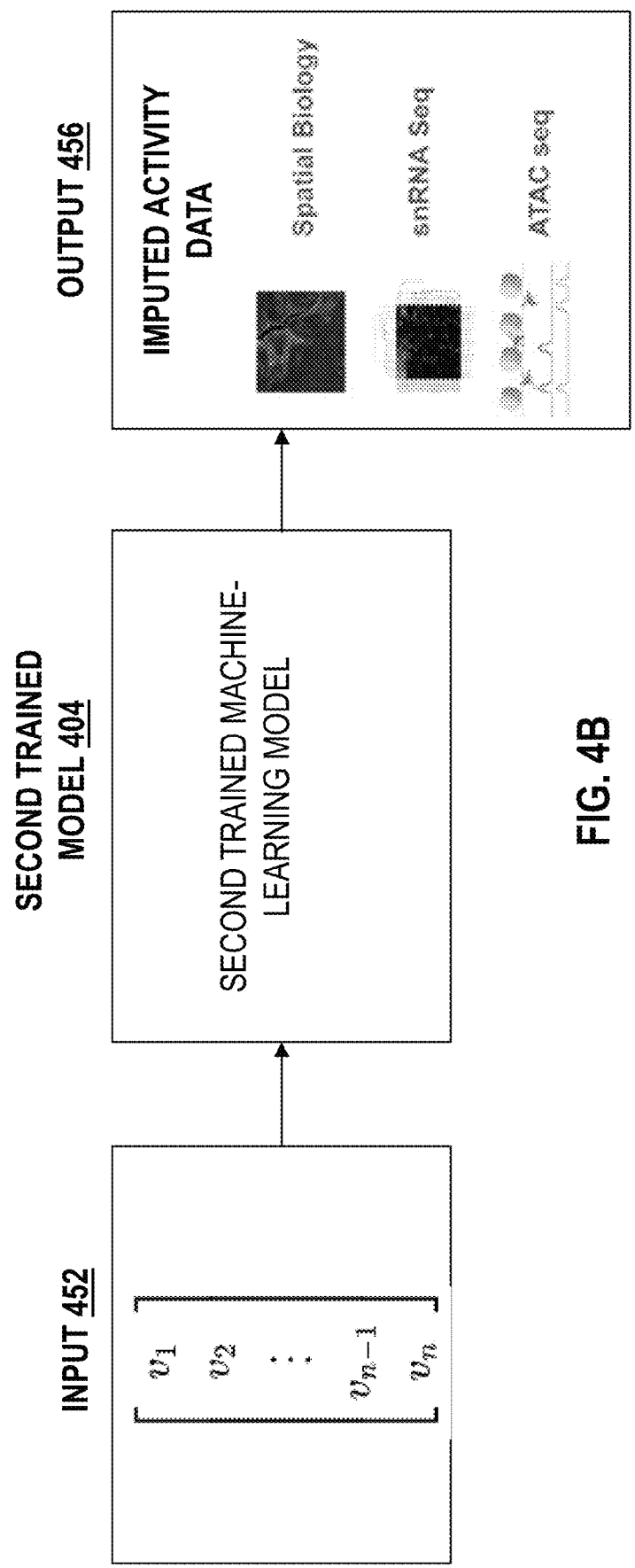
FIG. 4B illustrates the use of an exemplary trained second machine learning model, in accordance with some embodiments.

FIG. 4B illustrates the use of an exemplary trained second machine learning model, in accordance with some embodiments. The second machine learning model 404 can receive one or more embeddings 452 of a patient and output imputed molecular analyte activity data 456. As discussed above, the second machine learning model can be used in block 210 in FIG. 2B. In some embodiments, the input embedding data is obtained by providing imaging data of the patient to the first machine learning model.

FIG. 5 illustrates an exemplary process for using the trained first machine learning model and the trained second machine learning model to identify one or more relevant biomarkers, in accordance with some embodiments. The process 500 may correspond to blocks 208-214 of FIGS. 2A-B. An exemplary system (e.g., one or more electronic devices) can receive a plurality of medical images and outcome data of a cohort (e.g., a SoC cohort). With reference to FIG. 5, the cohort includes a plurality of patients 1-n. For each patient, the system can receive one or more images (e.g., histopathology images, MRI images, CT images) and optionally outcome data. For example, the system receives image data 502 and optionally outcome data 504 for patient 1, image data 552 and optionally outcome data 554 for patient n, etc.

The system can then determine a plurality of embeddings by providing the received images to a first trained machine learning model (e.g., model 304 in FIG. 3B). The first machine learning model is configured to receive image data and output one or more embeddings, which are numerical, low dimensional featurizations of the input. In the depicted example in FIG. 5, the system can provide image data 502 of patient 1 to the first machine learning model to obtain embedding(s) 506, provide image data 552 of patient n to the first machine learning model to obtain embedding(s) 556, etc.

The system can then determine imputed activity data of one or more molecular analytes by providing the plurality of embeddings to a second trained machine learning model (e.g., model 404 in FIG. 4B). The second machine learning model is configured to receive one or more embeddings and output imputed data. The imputed activity data of the one or more molecular analytes can comprise gene expression data, a copy number amplification value (e.g., from WGS, WGBS or targeted sequencing), an amplification signature value (e.g., from RNA-seq), chromatin accessibility data (e.g., ATAC-seq), DNA methylation data (e.g., WGBS, RRBS), histone modification (e.g., histone ChIP-seq), RNA data (e.g., from RNA-seq), protein data, spatial biology data, whole-genome sequencing (WGS) data (e.g., GWAS), somatic mutation data, germline mutation data, or any combination thereof.

In some embodiments, the data may comprise: a gene expression value comprising an abundance of a transcript, a chromosome accessibility score comprising an ATAC-seq peak value, abundance of one or more histone modifications comprising a ChIP-seq value, abundance of one or more mRNA sequences, abundance of one or more proteins, the presence of one or more somatic mutations, the presence of one or more germline mutations, or any combination thereof.

In the depicted example in FIG. 5, the system can provide embedding(s) 506 of patient 1 to the second machine learning model to obtain imputed data 508, provide embedding(s) 566 of patient n to the second machine learning model to obtain imputed data 568, etc.

In some embodiments, the second machine learning model is trained using a training dataset associated with a relatively small-scale cohort, such as the cohort 102 in FIG. 1A. This cohort may be smaller than the cohort comprising patients 1-n. As discussed above, data collected for the small-scale cohort can include data of shared modalities (e.g., imaging data) as well as high-content modality where specific MoAs (e.g., activity of specific genes or processes) can be discerned from the data. To generate the training dataset to train the second machine learning model, the imaging data (e.g., histopathology images) is provided to the trained first machine learning model to obtain corresponding embeddings. This way, for each subject in the cohort, both embeddings and the corresponding activity data of one or more molecular analytes (e.g., gene activation) for the subject are available. Accordingly, the second machine learning model can be then trained to receive embedding data and predict activity data of one or more molecular analytes for a subject, as discussed above with reference to FIG. 4A.

The system can then determine one or more relevant biomarkers 530 based on the outcome data of the cohort and the imputed activity data of the cohort. In the depicted example in FIG. 5, the outcome data of the cohort includes outcome data 504 for patient 1, . . . and outcome data 554 for patient n. The imputed activity data includes imputed data 508 for patient 1, . . . , and imputed data 559 for patient n.

In some embodiments, to determine a biomarker, the system calculates an association metric (e.g., p-value) indicative of a degree of association between the imputed activity data of a molecular analyte, which is a candidate biomarker, and the outcome data. In some embodiments, the association metric quantifies the association between the candidate biomarker and clinical outcome. By assessing associations between candidate biomarkers and the clinical outcome, the system identifies one or more biomarkers that have significant associations with the clinical outcome. For example, the association metric or correlation metric may be a hazard ratio, a risk ratio, or a p-value. In some embodiments, a hazard ratio may be estimated from a Cox proportional hazards model. More generally, the association between a candidate biomarker and a time-to-event outcome (e.g., overall survival, progression-free survival) may be quantified using a (weighted) log-rank test, a Cox proportional hazards model, an Aalen additive hazards model, or a parametric accelerated failure time model.

In some embodiments, the system performs the association test by generating, for each candidate biomarker, a candidate-biomarker-specific prediction model configured to receive data related to the candidate biomarker and output a predicted clinical outcome. The model is then evaluated to determine whether there is a significant association between the candidate biomarker and the clinical outcome. For example, the model may be a linear regression model and the system can calculate a p-value associated with the model and determines whether the p-value exceeds a predefined threshold to determine if there is a significant association. P-values are obtained through a standard Wald, score, likelihood ratio, or Monte Carlo testing procedure, and the effect size and standard errors are obtained through classical linear model theory, in some embodiments.

Other association testing procedures can be implemented to determine if there is a significant association between a candidate biomarker and clinical outcome. The association testing procedure can be also based on extensions of linear models such as linear mixed models or generalized linear regression or on nonlinear models (random forest, SVMs, etc.).

Figure 6:
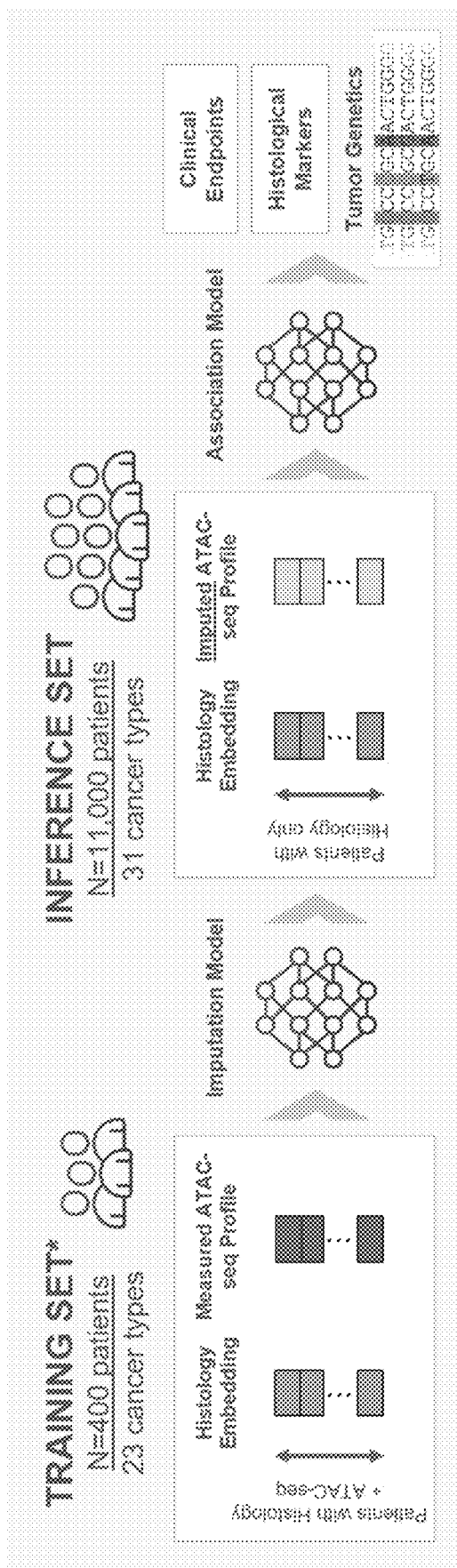
FIG. 6 illustrates an exemplary process for imputing molecular analyte activity measurements from histopathology embeddings, in accordance with some embodiments.

FIG. 6 illustrates an exemplary process for imputing molecular measurements from histopathology embeddings, in accordance with some embodiments. A first cohort includes 400 patients, and a dataset is collected for the first cohort to measure the ATAC-seq profiles on 400 TCGA samples, taken broadly across 23 cancer types. Due to the small number of patients and cancers in the dataset, the dataset can be underpowered for many insights across any cancer type.

On the other hand, a second cohort (e.g., a SoC cohort) includes 11,000 TCGA patients, but ATAC-seq profiles are not collected for the second cohort. According to embodiments of the present disclosure, an imputation model (i.e., the second machine learning model described in FIGS. 2A and 2B) is trained using a dataset of the first cohort. The trained imputation model is used to predict ATAC-seq signals for the second cohort from the histology embeddings of the second cohort, increasing power by close to 2 orders of magnitude.

Figure 7A:
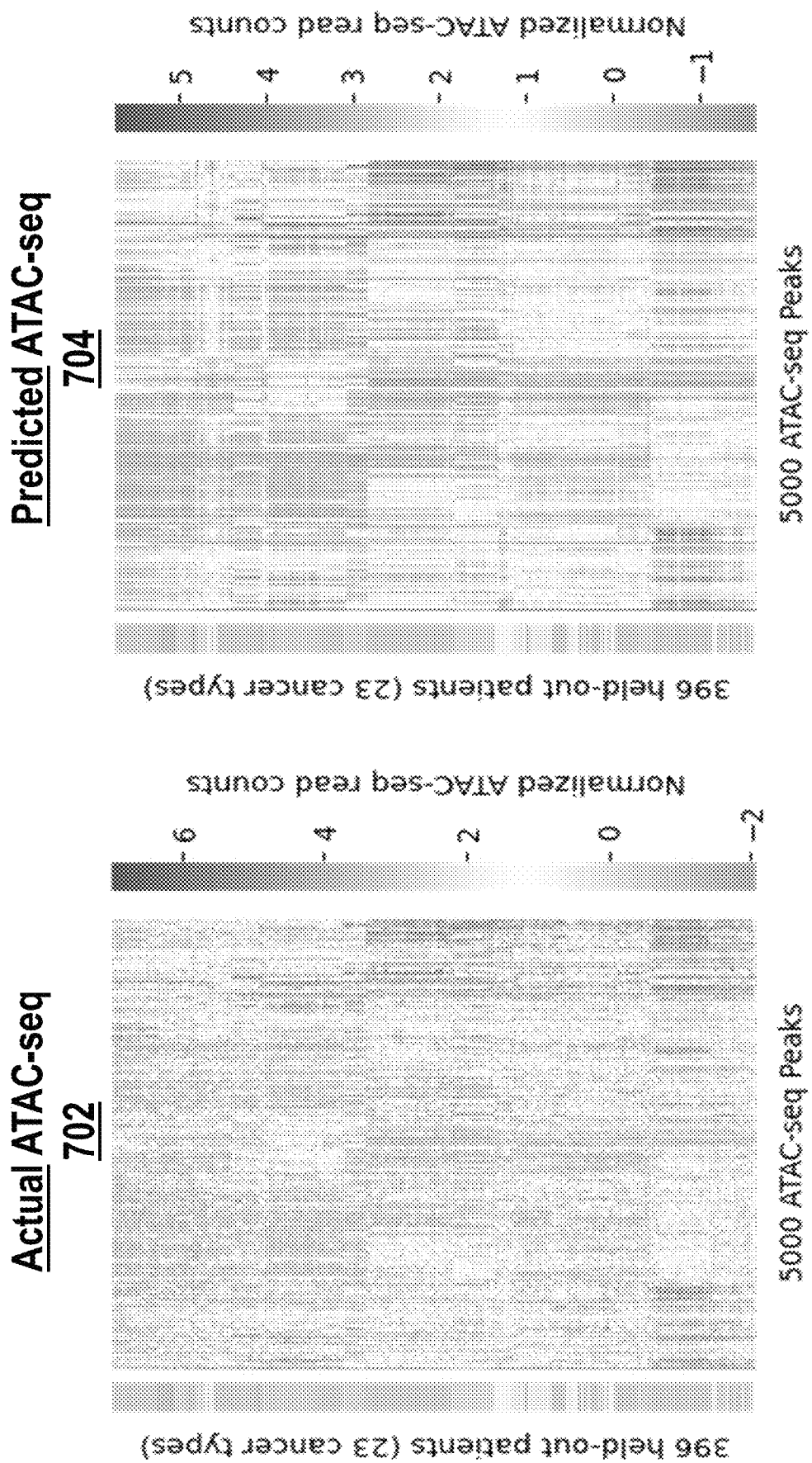
FIGS. 7A and 7B illustrate chromatin accessibility significantly predicted from histopathology embeddings, in accordance with some embodiments.
Figure 7B:
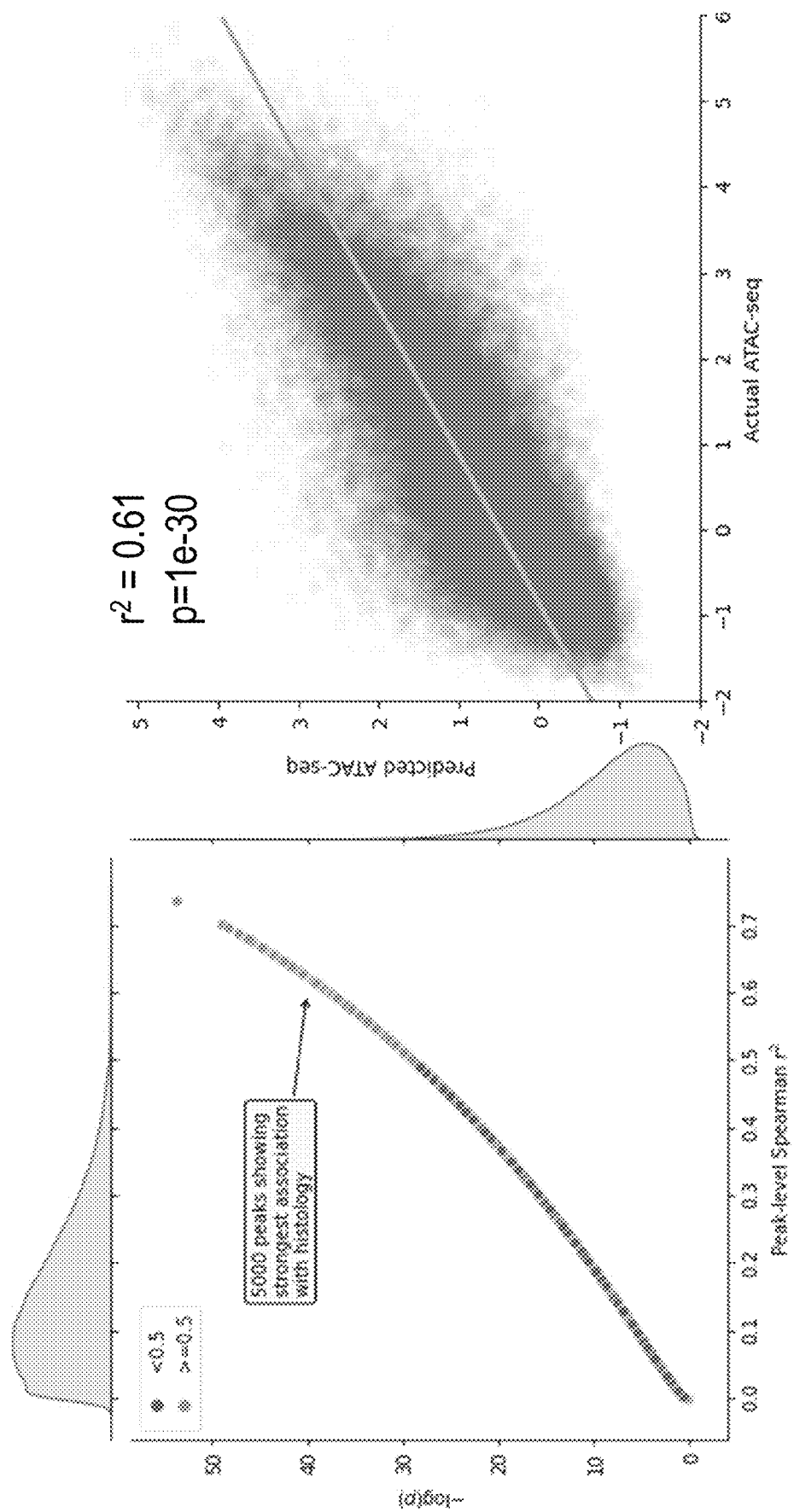

FIGS. 7A and 7B illustrate chromatin accessibility significantly predicted from histopathology embeddings, in accordance with some embodiments. A trained machine learning model (e.g., the second machine learning model in FIG. 2A) is configured to receive histopathology embeddings of one or more patients and predict measurement of activation of genomic regions for the one or more patients. FIG. 7A shows a comparison between actual ATAC-seq data 702 and predicted ATAC-seq data 704 of the same 396 patients across 23 cancer types. As shown in FIGS. 7A and 7B, high-accuracy predictions are obtained from approximately 5000 genomic regions. Specifically, approximately 5000 ATAC peaks were imputable at >0.5 Spearman r^2 on a held out test set. These 5000 peaks showing strong associations were prioritized and focused on in subsequent analysis.

Figure 7C:
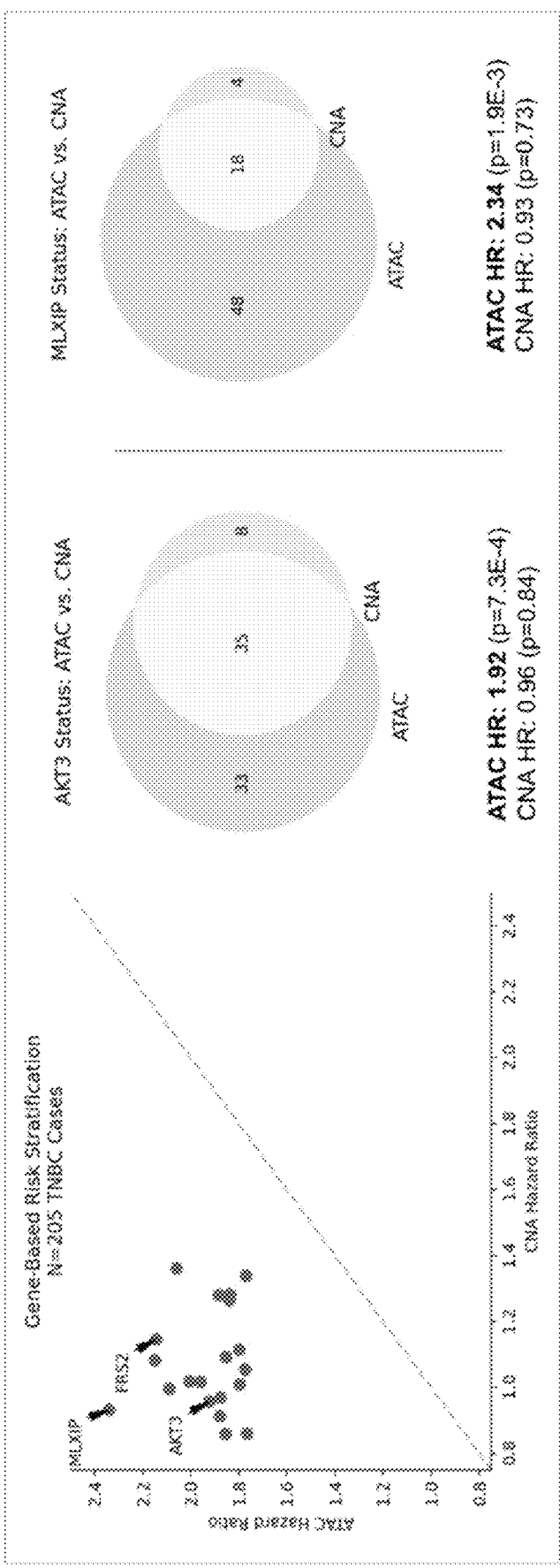
FIG. 7C shows an exemplary gene-based risk stratification, in accordance with some embodiments.

FIG. 7C shows an exemplary gene-based risk stratification, in accordance with some embodiments. As shown, a number of these showed strong association with survival (HRs~2)—considerably larger than the association with somatic alterations for the same genes, most of which did not even hit statistical significance. The size of the targeted patient population was also considerably larger, as demonstrated in FIG. 7C for two known cancer targets, including one—AKT3—currently under development in several biopharma pipelines across multiple indications.

FIG. 8 illustrates how imputed ATAC-seq signal helps identify novel outcome-associated genes, in accordance with some embodiments. As shown, the ATAC-seq peaks provide a layer of interpretability on the histopathology embeddings—pointing to specific genes that strongly associate with patient outcome. For both breast cancer and triple neg, the system can obtain some of the strongest known drivers as positive controls, and a few novel yet highly plausible genes, some with hazard ratios close to 2.

Figure 9:
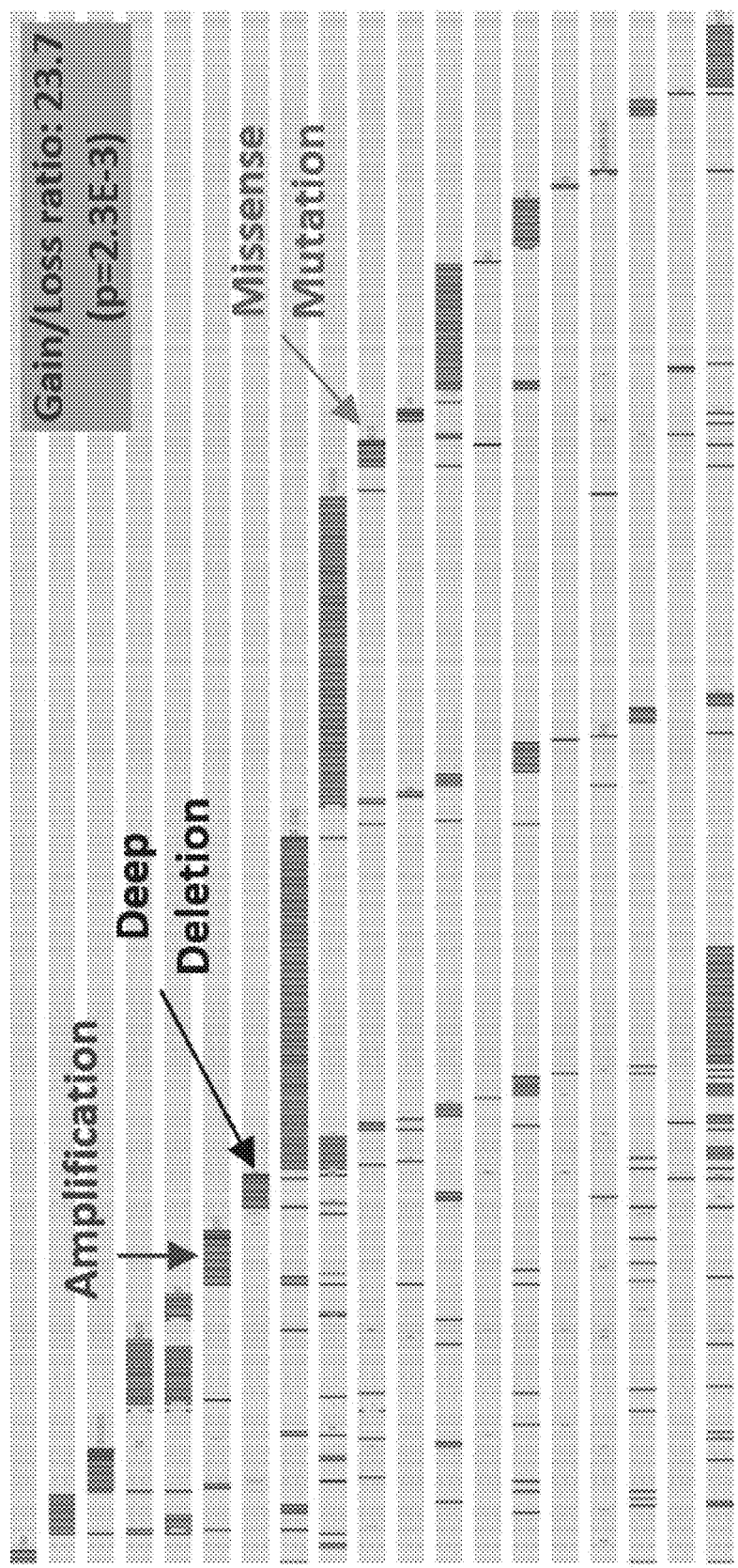
FIG. 9 illustrates exemplary validation data, in accordance with some embodiments.

FIG. 9 illustrates exemplary validation data, in accordance with some embodiments. FIG. 9 shows significant enrichment for amplification among ATAC-implicated TNBC genes and supports a causal role for gene activation in tumor proliferation and patient outcome. The system may increase conviction in targets via strong genetic evidence leveraging additional cohorts with high-content clinical data and complement with validation experiments leveraging in vitro and/or model systems.

While some of the embodiments disclosed herein involve training multiple machine learning models, it should be appreciated that similar techniques can be used to train a single machine learning model comprising multiple modules. For example, the first machine learning model, the second machine learning model, and the third machine learning model may instead be implemented as a first module (e.g., an embedding module), a second module (e.g., a molecularly analyte prediction head), and a third module (e.g., an outcome prediction head such as a survival head) of the same machine learning module, as discussed below with reference to FIG. 10. A head can comprise a set of one or more layers that are trained on one or more specific prediction tasks. The head can be part of the original model, or added to it post hoc. In some embodiments, a head can take in an embedding as input, and predict a given endpoint/molecular analyte, but they can also take other predictions as input (for example, a new head can be trained to predict survival from the molecular analyte predictions).

Figure 10:
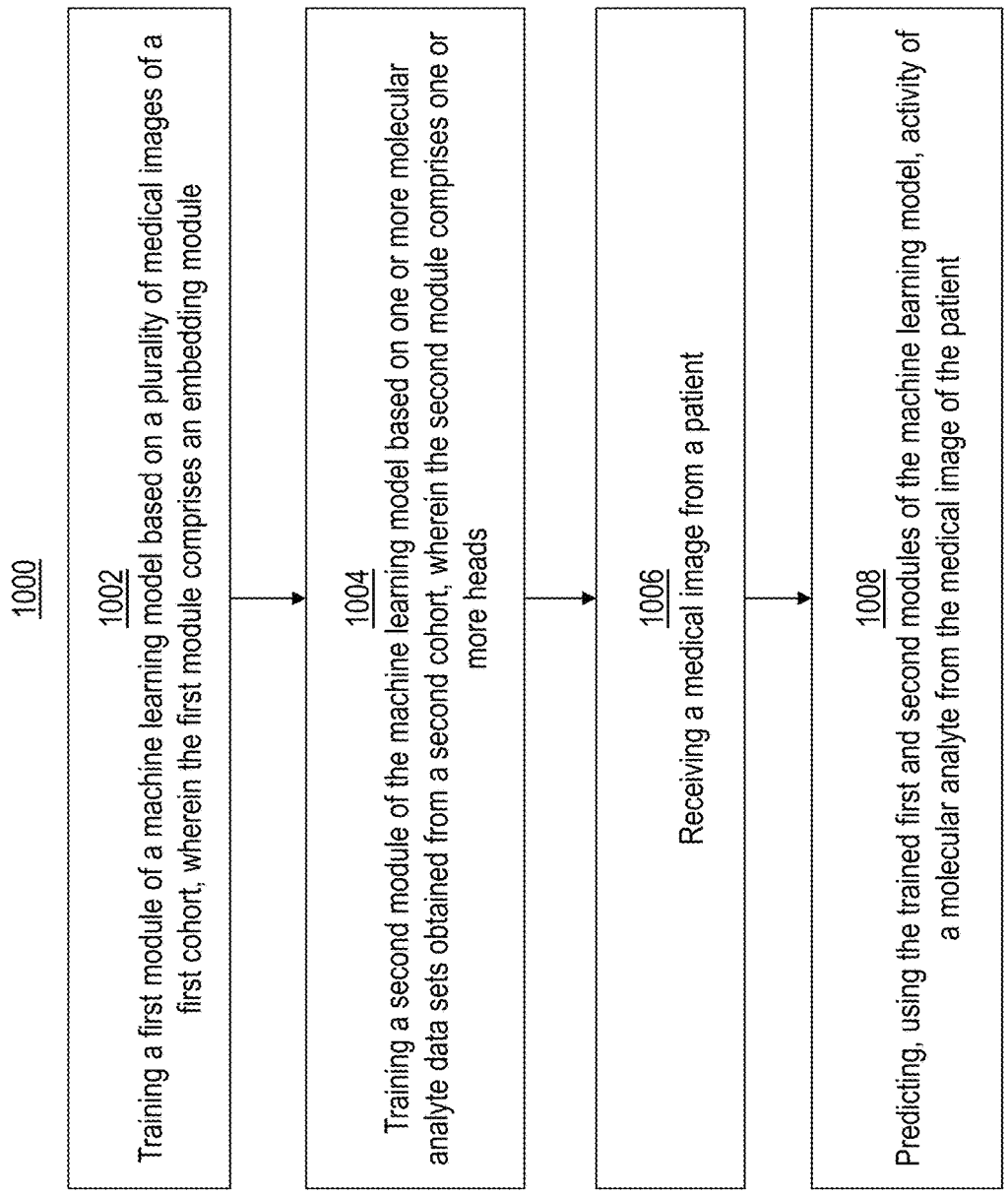
FIG. 10 illustrates an exemplary process in accordance with some embodiments.

FIG. 10 illustrates an exemplary process 1000 for predicting activity of a molecular analyte of a patient, according to some embodiments. Process 1000 is performed, for example, using one or more electronic devices implementing a software platform. In some examples, process 1000 is performed using a client-server system, and the steps of process 1000 are divided up in any manner between the server and one or more client devices. In other examples, process 1000 is performed using only a client device or only multiple client devices. In process 1000, some steps are, optionally, combined, the order of some steps is, optionally, changed, and some steps are, optionally, omitted. In some examples, additional steps may be performed in combination with the process 1000. Accordingly, the operations as illustrated (and described in greater detail below) are exemplary by nature and, as such, should not be viewed as limiting.

At block 1002, an exemplary system (e.g., one or more electronic devices) trains a first module of a machine learning model based on a plurality of medical images of a first cohort. The first module may comprise an embedding module that performs processing in a manner similar to the first machine learning model 304 in FIGS. 3A and 3B.

At block 1004, the system trains a second module of the machine learning model based on one or more molecular analyte data sets obtained from a second cohort. The second module may have one or more heads. The second module may perform processing in a manner similar to the second machine learning model 404 in FIGS. 4A and 4B.

At block 1006, the system receives a medical image from a patient. At block 1008, the system predicts, using the trained first and second modules of the machine learning model, the activity of the molecular analyte from the medical image of the patient. For example, the medical image can be provided to the first module to obtain an embedding, which is provided to the second module to obtain the prediction of the activity of the molecular analyte.

In some embodiments, the system further determines if the patient belongs to one or more subgroups based on the predicted activity of the molecular analyte. For example, if the predicted activity of the molecular analyte indicates the presence of a relevant biomarker, the system can determine that the patient belongs to a subgroup associated with the relevant biomarker.

In some embodiments, the system trains a third module of the machine learning model based on a third cohort, the third cohort comprising a plurality of medical images and associated clinical outcomes. The third module of the machine learning model is configured to predict a therapeutic and/or clinical outcome. The third module of the machine learning model may perform processing in a manner similar to the third machine learning model described with reference to FIGS. 2A and 2B.

In some embodiments, the system can use the third module to determine a measure of significance or prognostic value of the molecular analyte, which used to dynamically select a subset of molecular analytes for subsequent use (i.e., if the association between a molecular analyte and outcome is significant, the molecular analyte is selected for downstream use such as being identified as a relevant biomarker). As discussed herein, the significance value may be a cancer hazard ratio.

In some embodiments, the second module of the machine learning model and/or the third module of the machine learning model are trained using transfer learning. For example, the system can first train the second model/module to predict per-gene activity using one modality (e.g., RNA-seq), and then fine-tune (i.e., "transfer") the model to predict a related modality instead (e.g., ATAC-seq). This option would be especially appealing if the cohort with the RNA-seq was larger, but if the ATAC-seq showed stronger correlation with outcome. As another example, if both cohorts have ATAC-seq data, but there are batch effects in one, or one lacks outcome/response data, transfer learning may be used.

In some embodiments, the one or more molecular analyte data sets comprises: gene expression data (e.g., from RNA-seq), a copy number amplification value (e.g., from WGS, WGBS or targeted sequencing), an amplification signature value (e.g., RNA-seq), chromatin accessibility data (e.g., ATAC-seq), DNA methylation data (e.g., WGBS, RRBS), histone modification (e.g., histone ChIP-seq), RNA data (e.g., from RNA-seq), protein data, spatial biology data, whole-genome sequencing (WGS) data (e.g., GWAS), somatic mutation data, germline mutation data, or any combination thereof.

In some embodiments, the one or more molecular analyte data sets comprise: a gene expression value comprising an abundance of a transcript, a chromosome accessibility score comprising an ATAC-seq peak value, abundance of one or more histone modifications comprising a ChIP-seq value, abundance of one or more mRNA sequences, abundance of one or more proteins, the presence of one or more somatic mutations, the presence of one or more germline mutations, or any combination thereof. In some embodiments, the one or more molecular analyte data sets comprise two molecular analyte data sets (e.g., from two or more labs).

In some embodiments, the medical image from the patient is obtained from a fourth cohort comprising a plurality of medical images of a plurality of patients and optionally one or more associated molecular analyte data sets for each of the plurality of medical images. In some embodiments, the system can determine for each of the patients of the fourth cohort that the patient belongs to one or more subgroups.

In some embodiments, the first cohort comprises a plurality of medical images from a plurality of patients. In some embodiments, the plurality of medical images comprises: one or more histopathology images; one or more magnetic resonance imaging (MRI) images; one or more computerized tomography (CT) scans; or any combination thereof. In some embodiments, the plurality of medical images are unlabeled and the first module is trained using unsupervised learning.

In some embodiments, the first cohort and second cohort are the same cohort. In some embodiments, the second cohort (e.g., research cohort 102) comprises a plurality of medical images and data of one or more associated molecular analytes.

In some embodiments, the first, second or third cohort further comprise one or more clinical covariates.

In some embodiments, the third cohort (e.g., SoC cohort 112) comprises a plurality of medical images and associated clinical outcomes. The one or more clinical covariates can comprise patient gender, patient age, height, weight, patient diagnosis, patient histology data, patient radiology data, patient medical history (disease/treatment/billing history, physician notes), or any combination thereof.

In some embodiments, the system may remove data-specific biases in the first, second, and/or third cohort. For example, the system can use adversarial domain adaptation to learn to remove dataset-specific biases present in the second or third cohorts (i.e., map those embeddings to be indistinguishable from embeddings of the first cohort).

In some embodiments, at the test/inference time (i.e., on new/unseen patients), the system can use domain adaptation to map the new embeddings to the same space as the cohort 1-3 embeddings. For example, the system can receive a medical image of a new patient; obtain an embedding by providing the medical image of the new patient to the first module; and map the embedding based on domain adaptation. One example may be training a domain adaptation model on one or more additional training cohorts, or on augmented/perturbed examples from the prior cohorts using an adversarial loss, where the adaptation model is penalized if the adversary model is able to distinguish between the domains.

In some embodiments, the system can use transfer learning across related molecular analytes using a new cohort. For example, the system may train the second machine learning module to predict gene-level ATAC-seq signal on a large second cohort. Then, the system may transfer that second module (i.e., fine tune it) to train a fourth module to predict a related molecular analyte (which might also be ATAC-seq, or might be RNA-seq of the same genes) on a new cohort, which has fewer patients than the second.

Figure 11:
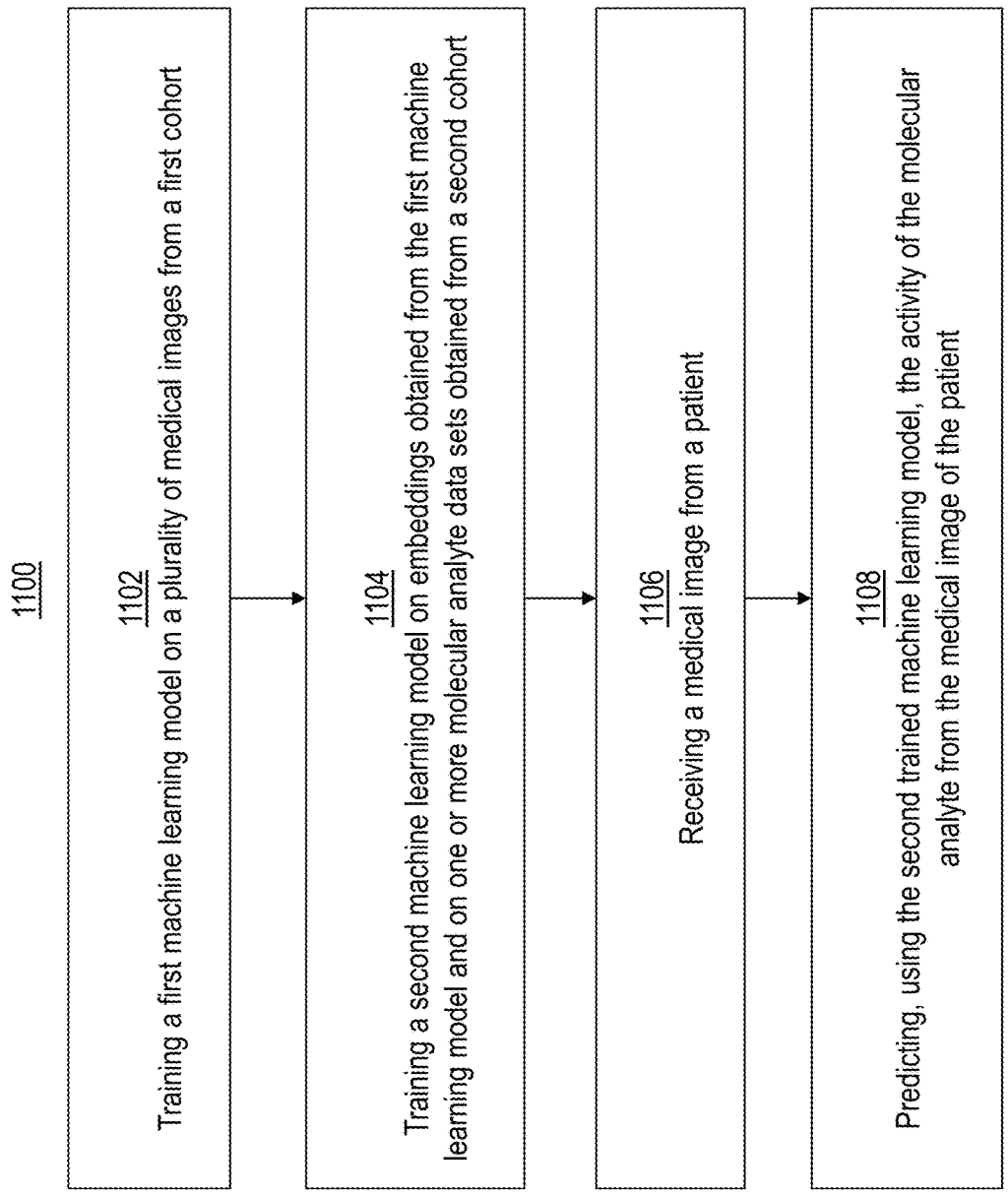
FIG. 11 illustrates an exemplary process in accordance with some embodiments.

FIG. 11 illustrates an exemplary process 1100 for predicting activity of a molecular analyte of a patient, according to some embodiments. Process 1100 is performed, for example, using one or more electronic devices implementing a software platform. In some examples, process 1100 is performed using a client-server system, and the steps of process 1100 are divided up in any manner between the server and one or more client devices. In other examples, process 1100 is performed using only a client device or only multiple client devices. In process 1100, some steps are, optionally, combined, the order of some steps is, optionally, changed, and some steps are, optionally, omitted. In some examples, additional steps may be performed in combination with the process 1100. Accordingly, the operations as illustrated (and described in greater detail below) are exemplary by nature and, as such, should not be viewed as limiting.

At block 1102, an exemplary system (e.g., one or more electronic devices) trains a first machine learning model on a plurality of medical images from a first cohort. The first machine learning model may be the first machine learning model 304 in FIGS. 3A and 3B.

At block 1104, the system trains a second machine learning model on embeddings obtained from the first machine learning model and on one or more molecular analyte data sets obtained from a second cohort. The second machine learning model may be the second machine learning model 404 in FIGS. 4A and 4B.

At block 1106, the system receives a medical image from the patient. At block 1108, the system predicts, using the second trained machine learning model, the activity of the molecular analyte from the medical image of the patient. For example, the medical image can be provided to the first model to obtain an embedding, which is provided to the second model to obtain the prediction of the activity of the molecular analyte.

In some embodiments, the system further determines if the patient belongs to one or more subgroups based on the predicted activity of the molecular analyte. For example, if the predicted activity of the molecular analyte indicates the presence of a relevant biomarker, the system can determine that the patient belongs to a subgroup associated with the relevant biomarker.

In some embodiments, the system trains a third machine learning model based on a third cohort, the third cohort comprising a plurality of medical images and associated clinical outcomes. The third machine learning model is configured to predict a therapeutic and/or clinical outcome. The third machine learning model may perform processing in a manner similar to the third machine learning model described with reference to FIGS. 2A and 2B.

In some embodiments, the system can use the third model to determine a measure of significance or prognostic value of the molecular analyte; and determine, based on the measure, if the molecular analyte is significantly associated with the therapeutic and/or clinical outcome such that the molecular analyte is used in subsequent patient stratification. As discussed herein, the significance value may be a cancer hazard ratio.

In some embodiments, the second machine learning model and/or the third machine learning model are trained using transfer learning.

In some embodiments, the one or more molecular analyte data sets comprises: gene expression data, a copy number amplification value (e.g., from WGS, WGBS or targeted sequencing), an amplification signature value (e.g., RNA-seq), chromatin accessibility data (e.g., ATAC-seq), DNA methylation data (e.g., WGBS, RRBS), histone modification (e.g., histone ChIP-seq), RNA data (e.g., from RNA-seq), protein data, spatial biology data, whole-genome sequencing (WGS) data (e.g., GWAS), somatic mutation data, germline mutation data, or any combination thereof.

In some embodiments, the one or more molecular analyte data sets comprise: a gene expression value comprising an abundance of a transcript, a chromosome accessibility score comprising an ATAC-seq peak value, abundance of one or more histone modifications comprising a ChIP-seq value, abundance of one or more mRNA sequences, abundance of one or more proteins, the presence of one or more somatic mutations, the presence of one or more germline mutations, or any combination thereof. In some embodiments, the one or more molecular analyte data sets comprise two molecular analyte data sets.

In some embodiments, the medical image from the patient is obtained from a fourth cohort comprising a plurality of medical images of a plurality of patients and optionally one or more associated molecular analyte data sets for each of the plurality of medical images. In some embodiments, the system can determine for each of the patients of the fourth cohort that the patient belongs to one or more subgroups.

In some embodiments, the first cohort comprises a plurality of medical images from a plurality of patients. In some embodiments, the plurality of medical images comprises:

one or more histopathology images; one or more magnetic resonance imaging (MRI) images; one or more computerized tomography (CT) scans; or any combination thereof. In some embodiments, the plurality of medical images is unlabeled and the first model is trained using unsupervised learning.

In some embodiments, the first cohort and second cohort are the same cohort. In some embodiments, the second cohort (e.g., research cohort 112) comprises a plurality of medical images and data of one or more associated molecular analytes.

In some embodiments, the first, second or third cohort further comprise one or more clinical covariates.

In some embodiments, the third cohort (e.g., SoC cohort 111) comprises a plurality of medical images and associated clinical outcomes. The one or more clinical covariates can comprise patient gender, patient age, height, weight, patient diagnosis, patient histology data, patient radiology data, patient medical history, or any combination thereof.

In some embodiments, the system may remove data-specific biases in the first, second, and/or third cohort. For example, the system can use adversarial domain adaptation to learn to remove dataset-specific biases present in the second or third cohorts (i.e., map those embeddings to be indistinguishable from embeddings of the first cohort).

In some embodiments, at the test/inference time (i.e., on new/unseen patients), the system can use domain adaptation to map the new embeddings to the same space as the cohort 1-3 embeddings. For example, the system can receive a medical image of a new patient; obtain an embedding by providing the medical image of the new patient to the first model; and map the embedding based on domain adaptation.

In some embodiments, the system can use transfer learning across related molecular analytes using a new cohort. For example, the system may train the second machine learning model to predict gene-level ATAC-seq signal on a large second cohort. Then, the system may transfer that second model (i.e., fine tune it) to train a fourth model to predict a related molecular analyte (which might also be ATAC-seq, or might be RNA-seq of the same genes) on a new cohort, which has fewer patients than the second.

Figure 12:
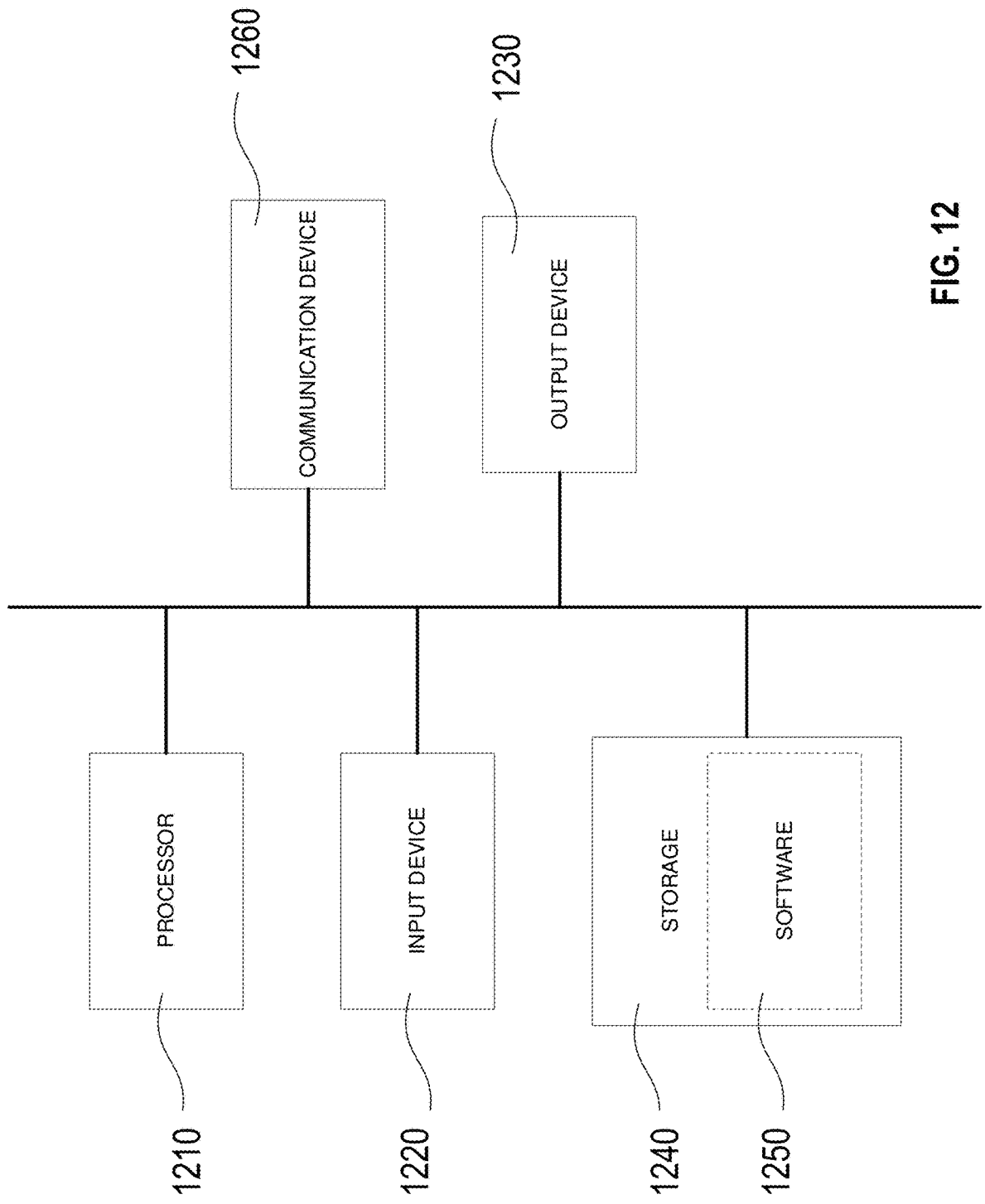
FIG. 12 illustrates an exemplary electronic device in accordance with some embodiments.

The operations described above are optionally implemented by components depicted in FIG. 12. It would be clear to a person having ordinary skill in the art how other processes are implemented based on the components depicted in FIG. 12.

FIG. 12 illustrates an example of a computing device in accordance with one embodiment. Device 1200 can be a host computer connected to a network. Device 1200 can be a client computer or a server. As shown in FIG. 12, device 1200 can be any suitable type of microprocessor-based device, such as a personal computer, workstation, server or handheld computing device (portable electronic device) such as a phone or tablet. The device can include, for example, one or more of processor 1210, input device 1220, output device 1230, storage 1240, and communication device 1260. Input device 1220 and output device 1230 can generally correspond to those described above, and can either be connectable or integrated with the computer.

Input device 1220 can be any suitable device that provides input, such as a touch screen, keyboard or keypad, mouse, or voice-recognition device. Output device 1230 can be any suitable device that provides output, such as a touch screen, haptics device, or speaker.

Storage 1240 can be any suitable device that provides storage, such as an electrical, magnetic or optical memory including a RAM, cache, hard drive, or removable storage disk. Communication device 1260 can include any suitable device capable of transmitting and receiving signals over a network, such as a network interface chip or device. The components of the computer can be connected in any suitable manner, such as via a physical bus or wirelessly.

Software 1250, which can be stored in storage 1240 and executed by processor 1210, can include, for example, the programming that embodies the functionality of the present disclosure (e.g., as embodied in the devices as described above).

Software 1250 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1240, that can contain or store programming for use by or in connection with an instruction execution system, apparatus, or device.

Software 1250 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 1200 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1200 can implement any operating system suitable for operating on the network. Software 1250 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Figure 14B:
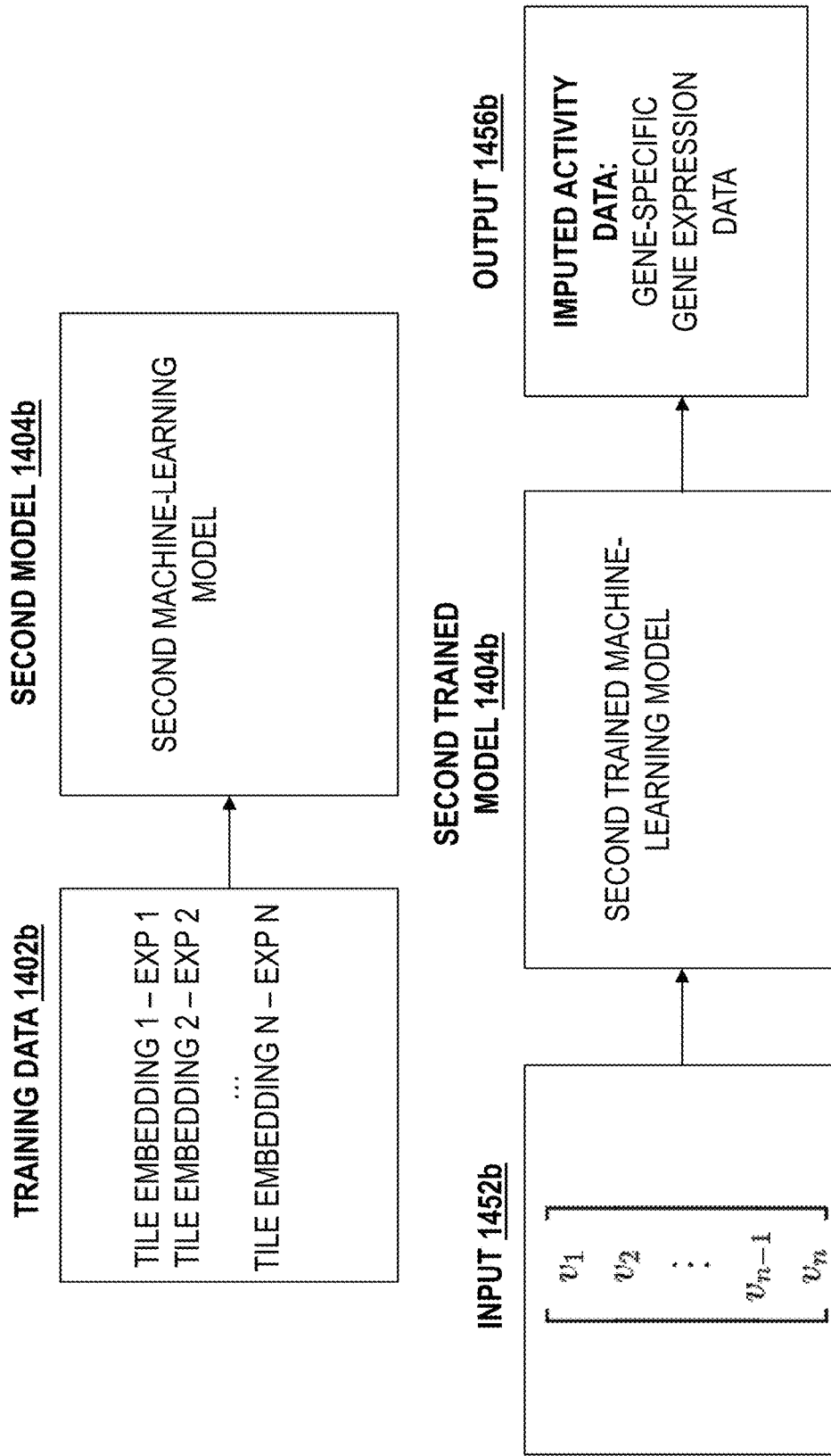
FIG. 14B illustrates the training and use of the second machine learning model for predicting gene expression in accordance with some embodiments.
Figure 14C:
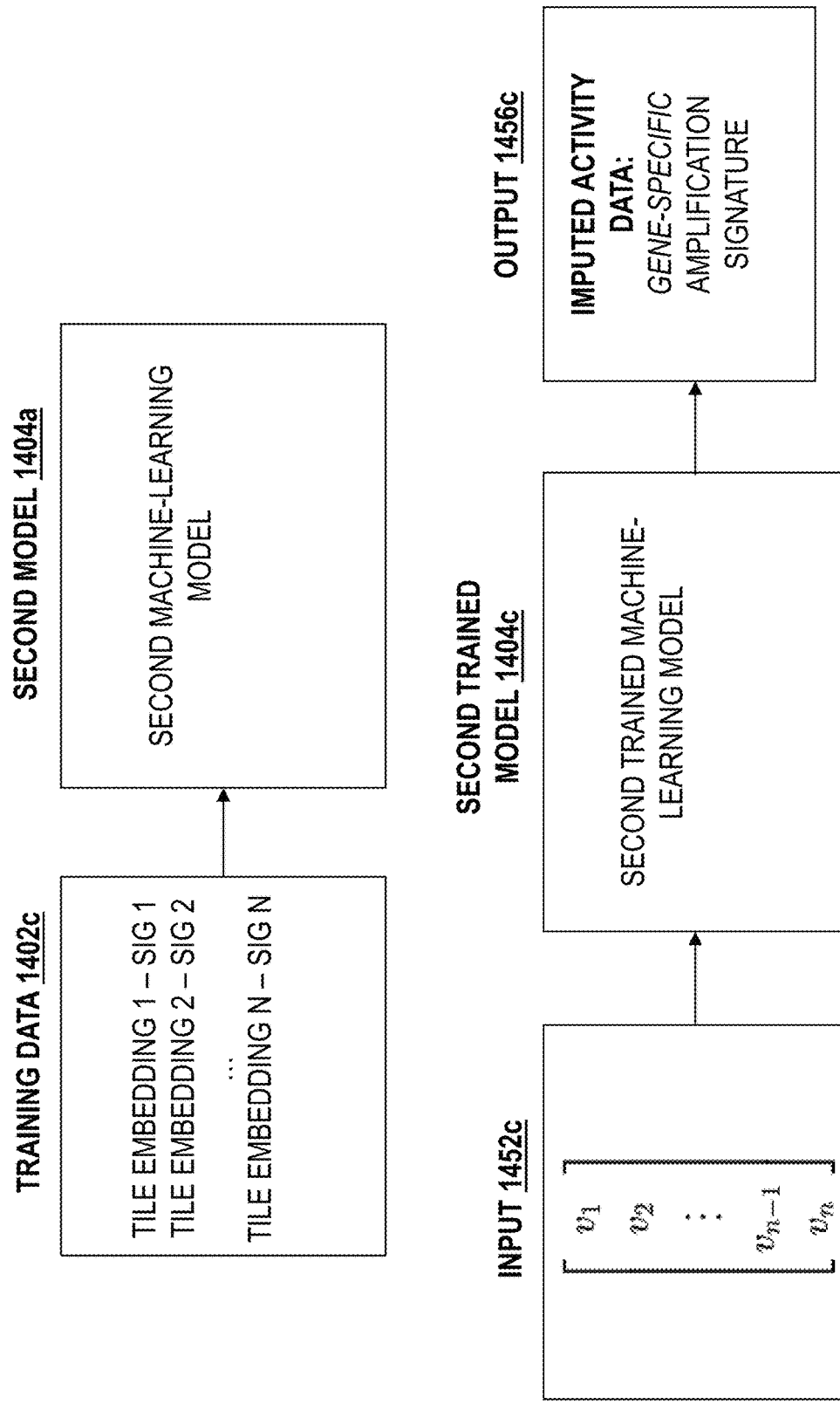
FIG. 14C illustrates the training and use of the second machine learning model for predicting a gene signature associated with copy number amplification in accordance with some embodiments.

An overview of exemplary embodiments configured for prediction of gene-specific copy number amplification (CNA), gene-specific expression, and gene-specific amplification signatures is provided below with reference to, for example, FIGS. 14A-14C and an Exemplary Studies section. While FIGS. 14A-14C are described with respect to imputing specific types of molecular analyte activity, it should be understood that the models may be configured to predict other factors, such as protein levels or any other molecular analyte activity described herein. Proteins, for instance, are the direct therapeutic targets of many drugs, including those evaluated in the Exemplary Studies section, below. Thus, a multi-task approach, such as the one described below, would be beneficial in this context as well. Further, the generality of the framework described herein would allow multi-task learning on multiple biomarker types in the same model, enabling information transfer across CNA, RNA, protein, and more.

Cancer is a highly heterogeneous disease, and despite significant advances in the discovery and development of "precision" approaches to management, patients' responses to targeted treatments can still be highly variable, without an understanding as to why. Growth in the development of targeted therapies has accelerated the use of predictive biomarkers to identify the patients that are more likely to respond to a drug. Indeed, studies have shown that oncology trials that use biomarkers have a considerably higher success rate, with a nearly 5-fold increased likelihood of drug approval across all indications combined, and a 12-, 8- and 7-fold improvement for breast cancer, melanoma and non-small cell lung cancer (NSCLC), respectively.

Current predictive biomarkers generally leverage one of several assay types: immunohistochemistry (IHC) on biopsy slides; genetic analysis, including karyotyping, fluorescence in situ hybridization, and DNA sequencing; or transcript levels of a small set of genes, measured either via polymerase chain reaction (PCR) or (rarely) broad-based RNA sequencing. The development and deployment of these approaches present significant challenges. First and foremost, these methods rely on specialized assays that are not universally available across cancer centers, and even more so in resource-poor settings. Second, some of these technologies such as IHC, require manual assessment by a trained individual, which might increase variability and decrease reproducibility of the assay results. Third, they entail additional cost and, even more importantly, require additional time that could postpone the time to a diagnosis and the initiation of treatment. Moreover, while the sequencing-based assays leverage technologies that have seen generally broad adoption and their use is fairly standardized, a biomarker that utilizes targeted staining or probes, including IHC and PCR, will usually require the development and extensive testing of specialized assays and reagents.

Current development paradigms and available technologies favor early selection of a biomarker, at a stage where available data is generally based on poorly representative preclinical models and/or underpowered phase 1 studies, both of which fail to capture the heterogeneity in human patient populations. This drives a tendency towards simple biomarkers that are largely driven by human mechanistic understanding of the disease, usually either genetic aberrations as measured by sequencing, or transcript/protein expression as measured by chemistry. As a consequence, the labeled population is often overly restricted-reducing the set of patients who benefit, or overly broad, subjecting a subset of patients to a drug that has limited efficacy, while still carrying the risk of toxicity and delaying treatment with a potentially more efficacious therapy.

Existing studies have predominantly utilized a per-task supervised learning framework, where a single deep learning model is trained to predict a specific, defined biomarker in clinical use, in a given type of cancer, directly from the H&E images. For example, in the work of S Arslan, D Mehrotra, J Schmidt, et al. *Deep learning can predict multi-omic biomarkers from routine pathology images: A systematic large-scale study*. bioRxiv, 2022, over 13,000 distinct models are trained, one for each cancer, biomarker, and fold. This approach limits the usable training data to individuals within a single cancer for whom the known biomarker has been measured.

Described herein (e.g., above with reference to FIGS. 1-13 and below with reference to FIGS. 14A-14C and an Exemplary Studies section) is an approach for the development and deployment of a class of predictive biomarkers to simultaneously predict a range of molecular factors that are relevant to treatment selection and response, leveraging deep learning on SoC obtained data such as images of H&E samples. Such images are routinely collected and processed for almost all solid tumor patients (world-wide) and are increasingly digitized. These images can be rich in information, and enable automated disease detection, prognosis prediction, cancer grading, histological and molecular subtyping, and customized treatment planning. Accordingly, the systems and methods described herein provide a novel multi-cancer, multi-biomarker prediction framework that leverages the commonality of cancer mechanisms across cancer types, as well as different genes and mutations, that manifest both in SoC data such as H&E slides and in the molecular readouts. The predictive performance of the models described herein increases significantly by moving from predicting a single molecular readout to a multi-task prediction across all defined target genes to a transcriptome-wide prediction. A broad comparison to the results of Arslan et al., is challenging due to the very limited overlap in biomarkers between their work and ours. However, for CDK4, which is the only shared RNA biomarker, they report at AUROC of around 0.72 (averaged across 3 cancer types), whereas the models described herein obtain an AUROC of 0.84 pan-cancer; of 0.75 in a stratified analysis, averaged across all cancer types; and of 0.77 when filtering to 4 relevant cancer types (specifically, breast, colorectal, lung, and pancreatic).

In some embodiments, one or more machine learning models described herein may be trained for multi-biomarker prediction. Embeddings generated based on images of tissue, for instance, hematoxylin and eosin (H&E)-stained biopsy samples, may be utilized to train discovery machine learning models to predict multiple biomarkers simultaneously using a multi-task learning approach. In some embodiments, a pan-solid tumor H&E foundation/discovery model is trained, learning a universal featurization of tissue H&E images. Foundational embeddings generated by the one or more foundation/discovery models may then be used as input to downstream machine learning models, such as the second machine learning model described above (and in additional detail below). By predicting multiple biomarkers simultaneously using a multi-task learning approach, a first set of downstream models allow for exploratory analysis and broad discovery. To enhance interpretability, these models may predict on the basis of tile-level rather than slide-level featurizations, where a tile constitutes a small element of the far larger whole slide image. Having tile-level predictions may enable the generation and overlay of annotation maps, highlighting the regions of a slide driving the model's predictions. Despite being trained on bulk, rather than spatially resolved, molecular data, the model is able to learn spatial variation in tumor cell molecular markers that correlates with the regions identified as cancerous by blinded pathologist review.

The initially broad set of imputations allows for hypothesis-free investigations of which biomarkers are relevant to which patient populations, and for the identification of biomarkers that differentiate patient subgroups. Once a smaller set of biomarkers specific to the patient population of interest has been selected from a discovery panel, specialized models can be trained, starting from the same foundational featurization, which may outperform the discovery model at predicting key biomarkers in targeted subgroups. This two-step process of imputing broadly then specializing on a more-focused subset enables both the discovery of novel biomarkers and the optimization of their diagnostic performance.

As such, the techniques described herein enable optimization of the patient population for a targeted therapy beyond the use of genetic alterations or IHC, but without going to the other extreme of an overly broad label covering an excessively heterogeneous patient set. Moreover, despite the fact that the imputation models were trained on bulk readouts, they enable overlay of spatially varying, tile-level predictions on top of the input histology images, providing a lens of interpretability and enabling clinicians to gauge (e.g.) if pairs or sets of biomarkers are spatially colocalizing within a tumor. Overall, the results described in detail below support the viability and ongoing exploration of using highly scalable molecular predictions from H&E as a flexible and generalizable approach to the development and deployment of predictive biomarkers for targeted therapeutics in cancer.

To demonstrate the value of this method, studies were performed focusing on biomarkers that are relevant to the efficacy of drugs whose mechanism of action (MOA) is based on the differential recognition and killing of cancer cells via the abundance of a particular protein target: antibodies (both mono-specific and multi-specific), antibody-drug conjugates (ADCs), and T-cell engagers. Three exemplary biomarkers, copy-number amplification (CNAs), RNA transcript level/gene expression level, and an RNA-derived amplification signature capturing the effect of a target's CNA on the transcriptome were evaluated as described in additional detail below with reference to the Exemplary Studies section. Across a large and diverse set of cancer types and biomarkers, the techniques described herein delivered high-accuracy patient-specific predictions of molecular readouts, both for continuous and dichotomized versions of these biomarkers. RNA-derived signatures, also referred to herein as amplification signatures, were shown to be reliable proxies for CNAs. Exemplary descriptions of models for imputing such biomarkers are provided below with reference to FIGS. 14A-14C and the performance of these exemplary models is described in the Exemplary Studies section below.

Antibody-Drug Conjugates (ADCs) are a class of targeted cancer therapies designed to deliver cytotoxic (cell-killing) drugs directly to cancer cells while minimizing damage to normal, healthy cells. ADCs deliver the chemotherapy via a linker attached to a monoclonal antibody that binds to a specific target expressed on cancer cells. After binding to the target (cancer protein or receptor), the ADC releases a cytotoxic drug into the cancer cell. As described herein, a plurality of target genes can be identified based on existing ADCs. For example, a pharmaceutical database can be queried to identify drugs whose therapeutic class was labeled as antibody-drug conjugate (ADC), T-cell engager, or antibody, including both mono-specific and multi-specific antibodies and the overall list of drugs can be then filtered to those with specified targets to identify targets. These targets can be imputed (e.g., by training the first and second machine-learning models) and, based on the imputed values, one or more biomarkers can be identified (e.g., via the third machine-learning model as described herein). The biomarker can be used to evaluate a new patient and identify/administer a treatment plan. For example, the biomarker value can be determined for the new patient, and if the biomarker value meets one or more criteria (e.g., exceeds a threshold, falls below a threshold, falls within or outside a range), a corresponding ADC can be prescribed accordingly.

In some embodiments, the second machine learning model described herein may be trained to impute copy number amplification for a set of genes (e.g., a set of target genes). Copy number amplification (CNA) may be imputed directly (as described with reference to FIG. 14A) by training the second machine learning model with image based embeddings (e.g., histopathology image based embeddings, MRI image based embeddings, and the like) labeled with observed CNA labels (e.g., binary values of zero or one indicating whether a CNA was detected) to impute a patient's target matrix (e.g., with binary values of zero or one indicating whether a CNA was detected and/or values corresponding to a probability score of 0 to 1 of a given patient having an amplification in a respective gene). CNA may also be imputed indirectly, as shown in FIG. 14B, by training a model using embeddings paired with target gene expression values to impute a patient's target matrix with values corresponding to the imputed expression (e.g., expression level) of each target gene within a patient. Patients with a CNA in a given target gene will generally have relatively higher expression of that target than those without CNA in a given target gene, so the expression matrix provides an approximation of CNA for each gene. FIG. 14C, described in detail below, illustrates an additional method for indirectly imputing CNA using a gene-specific amplification signature approach, wherein the amplification signatures are determined based on a weighted gene expression level for each differentially expressed gene. Model performance for each of the above referenced models was evaluated on a set of target genes and an overview of the results is provided in the attached exhibits. The imputation models described with reference to FIGS. 14A-14C may be trained and validated using data from a public research data resource (TCGA) that includes genetic, molecular, and histological data from over 20K primary tumors across 33 cancer types. Additional molecular and histological data were derived from a commercially available multi-center cancer research resource (referred to herein as cohort A).

Target genes may be identified based on data available related to targeted gene therapies. In some of the examples described herein, a commercial pharmaceutical database was queried to identify drugs whose therapeutic class was labeled as antibody-drug conjugate (ADC), T-cell engager, or antibody, including both mono-specific and multi-specific antibodies. For ADCs and T-cell engagers, drugs at any stage of development were retained, while for antibodies (a larger class), drugs whose development had ceased were excluded. The overall list of drugs was filtered to those with specified targets. Each remaining drug was mapped to a HGNC gene symbol, and the union of all gene symbols was taken, resulting in 352 unique targets.

In any of FIGS. 14A-C, the second machine-learning model may be a module of a machine-learning model. Any of these models may be trained for regression, classification tasks, or other tasks. Any of these models may be trained in a single-step process (e.g., imputing outputs directly) or in a two-step process (e.g., imputing broadly then specializing on a more-focused subset) as described herein. For example, the pan-cancer, pan-biomarker approach described herein may not maximally learn to recognize features that capture tumor- or biomarker-specific variation and instead may focus on learning features that generalize across tasks. This can be addressed by refining (e.g., fine-tuning) the base model (e.g., model 1404a, 1404b, 1404c) to a specific prediction task. This task can be a single cancer, a single biomarker, or a combination of both. A similar process could be applied to fine-tune one or more other models described herein (e.g., the third machine learning model described with reference to FIGS. 2A and 2B), for instance, to a treatment-response data set for a drug with a relevant mechanism of action (MOA), shifting the model towards better predicting patient response. Because of the extensive pre-training of the model, such fine-tuning might be feasible even from the small-scale cohorts available in phase 1/2 clinical trials. Exemplary results for such fine-tuned models are provided below in the Exemplary Studies section.

FIG. 14A illustrates an exemplary process for training and using the second machine learning model 1404a to impute copy number amplification (CNA) directly. In the depicted example in FIG. 14A, training data 1402a includes tile embeddings that may be generated by using the first trained machine learning model (e.g., first model 304 described above) to generate low dimensional embeddings of histopathology images (e.g., from the first cohort). Tile embeddings may be paired with observed CNA values from subjects. CNA values can be determined via observation to identify whether a given gene is amplified. For instance, in some examples, two approaches were utilized to identify genes with focal amplifications based on whole exomes from tumor specimens: GISTIC2 (v2.0.22), which estimates copy number relative to a matched normal sample, and Sequenza (v3), which estimates the absolute copy number. In some examples, a gene was designated as focally amplified if it received a GISTIC2 score of 2, or if it exhibited a copy number greater than twice the ploidy based on Sequenza. The tile embeddings may be obtained, for instance, by providing histopathology images from the first cohort to the first trained machine learning model (e.g., first model 304) to obtain a low-dimensional representation of each histopathology image.

Training data 1402a may be used to train the second machine learning model 1404a to directly predict subject CNA labels/values (e.g., a binary value of zero or one indicating whether a CNA was detected and/or probability values between zero and one indicative of the likelihood that a respective gene is amplified) given new input embedding data. In some embodiments, the training data may include binary amplification labels (e.g., 1 corresponding to an amplified gene and 0 corresponding to a non-amplified gene) and the trained model may generate predicted probabilities (e.g., between zero and one) indicating whether a gene is likely amplified). That is, in some embodiments, the model can be regression model configured to output a continuous value indicative of probability. In some embodiments, the model can be a classification model configured to output a binary outcome (e.g., amplified or not amplified).

In some examples, the second machine learning model 1404a is configured to make individual tile-level predictions, which are then averaged. Training model 1404a to predict on the tile-level rather than slide-level featurizations may enhance interpretability. For instance, having tile-level predictions may enable the generation and overlay of annotation maps, highlighting the regions of a slide driving the model's predictions. In some examples, second machine learning model 1404a is trained on bulk, rather than spatially resolved, molecular data, and second machine learning model 1404a is able to learn spatial variation in tumor cell molecular markers that correlates with the regions identified as cancerous by blinded pathologist review, as demonstrated in the Exemplary Studies section below.

Additionally, or alternatively, the second machine learning model 1404a may be trained to impute molecular analyte activity based on an average of the featurization of one or more tiles and/or the second machine learning model 1404a may be equipped with an attention mechanism (e.g., a cross-tile spatial attention mechanism) allowing the model to make patient-level predictions while attending to spatially adjacent tiles. However, in some examples, configuring model 1404a to make individual tile-level predictions may outperform models configured with attention mechanisms and/or models trained to impute molecular analyte activity based on an average of the featurization of one or more tiles. The improved performance resulting from configuring the model to make individual tile-level predictions may be due to the fact that averaging before making predictions attenuates the signal and loses resolution.

Once trained, the second trained model 1404a may be provided with input tile embeddings 1452a from a patient and output imputed molecular analyte activity data 1456a. In some embodiments, the input embedding data is obtained by providing imaging data of the patient to the first machine learning model. In the depicted example of FIG. 14A, the imputed molecular analyte activity data 1456a includes gene-specific copy number amplification values. The output may be a patient matrix with values corresponding to a probability score from 0 to 1 of a given patient having an amplification for each target gene and/or binary labels indicating whether or not each target gene is amplified, as described above.

In some examples, a second training stage may be utilized to finetune second machine learning model 1404a for specialized tasks. In some examples, second machine learning model 1404a may be finetuned for predicting imputed CNA molecular analyte activity data 1456a based on a subset of the training data. The subset of the training data may correspond to a patient attribute, which may include a specific cohort of patients, a disease, a biomarker, or a combination thereof. For instance, the second machine learning model 1404a may be finetuned to predict imputed CNA for a specific cohort of patients/subjects, a specific disease (e.g., type of cancer), a specific biomarker, or a combination thereof. Such fine-tuned models can provide improved performance for a specific prediction task (e.g., as shown in the MET case study below). Because of the extensive pre-training of the model, such fine-tuning might be feasible even from the small-scale cohorts available in phase 1/2 clinical trials. Moreover, a similar process could be applied to fine-tune a model to a treatment-response data set for a drug with a relevant MOA, shifting the model towards better predicting patient response.

As discussed above, the second machine learning model can be the second machine learning model described with reference to FIGS. 2A and 2B, and the imputed molecular analyte activity determined by model 1404a can be used in block 210 in FIG. 2B to determine a biomarker. The biomarkers determined at block 210 may thus include imputed gene-specific CNA values. Also, as described above with reference to FIGS. 2A and 2B, a variety of different clinical outcome prediction methods are available based on the imputed activity data. Any of those described above with reference to blocks 210-214 may be used to predict clinical outcomes based on imputed CNA values (e.g., a third machine learning model may be trained to determine an association between imputed activity data and clinical outcome data).

For example, the system may identify one or more relevant biomarkers based on the imputed activity data output by the second machine learning model 1404a and outcome data of patients/subjects associated with the image data from which input embeddings 1452a were obtained. In some embodiments, the system determines, using a third machine learning model, an association of the imputed activity data and clinical outcome data from the second cohort. Specifically, the system can train, using the imputed activity data and the clinical outcome data of the second cohort, the third machine learning model that is configured to predict an outcome based on activity data of a molecular analyte. For example, for each candidate biomarker (e.g., CNA value) the system can train a candidate-biomarker-specific prediction model configured to receive data related to the candidate biomarker and output a predicted clinical outcome (e.g., response to treatment, time-to-progression, time-to-death).

The candidate-biomarker-specific model is then evaluated to determine whether there is a significant association between the candidate biomarker and the clinical outcome. In some embodiments, the system can determine, based on the model, an association metric or correlation metric indicative of a degree of association or correlation between the candidate biomarker and clinical outcome. An association metric and a correlation metric are used interchangeably in the present disclosure.

For example, the association metric or correlation metric may be a hazard ratio, a risk ratio, or a p-value. In some embodiments, a hazard ratio may be estimated from a Cox proportional hazards model. More generally, the association between a candidate biomarker and a time-to-event outcome (e.g., overall survival, progression-free survival) may be quantified using a (weighted) log-rank test, a Cox proportional hazards model, an Aalen additive hazards model, or a parametric accelerated failure time model.

As another example, the model may be a generalized linear regression model or a time-to-event regression model, and the system can calculate a p-value associating one or more imputed molecular analytes with one or more clinical outcomes. The p-values can be obtained through a standard Wald, score, likelihood ratio, or Monte Carlo testing procedure, and the effect size and standard errors can be obtained through classical generalized linear model theory, in some embodiments. The p-value is indicative of the association between the candidate biomarker and the clinical outcome.

Other association testing procedures can be implemented to determine if there is a significant association between a candidate biomarker and clinical outcome. The association testing procedure can be also based on extensions of generalized linear models such as linear mixed models or generalized estimating equations or on nonlinear models (random forest, SVMs, etc.). Additional information for obtaining histopathology embeddings and conducting association testing can be found in U.S. Provisional Application No. 63/233,707 entitled "DISCOVERY PLATFORM" and PCT Application No. PCT/US2022/075006 entitled "DISCOVERY PLATFORM", the content of which is incorporated herein by reference for all purposes.

The system then identifies one or more relevant biomarkers based on the association. For example, the system can determine whether the p-value corresponding to a candidate biomarker exceeds a predefined threshold to determine if there is a significant association. If the p-value corresponding to the candidate biomarker exceeds the predefined threshold, the system may determine that the candidate biomarker is a relevant biomarker.

In some embodiments, the association metric may indicate a positive association or a negative association. In some embodiments, either a significant (e.g., statistically significant, exceeding a predefined threshold) positive association or a significant negative association may be identified as a relevant biomarker.

The system may also perform patient stratification based on the identified biomarkers. For example, a signature (e.g., histopathology signature) that aligns with the predicted MoA defines the "likely responder" patient population. In some embodiments, patient stratification can be based on one or more images of a particular patient. The system can determine if the patient belongs to one or more patient subgroups by determining if the one or more images of the patient indicate an alignment with the determined one or more relevant biomarkers. In addition to a discretized result (one or more discrete subgroups), the system may also return a continuous score to the patient/physician (e.g., level of PD-L1 expression, TMB, HER2 quantification by FISH, etc.).

Specifically, the system may receive one or more medical images of a patient. The system can provide the one or more images of the patient to the first trained machine learning model to determine one or more embeddings. The system can then provide the one or more embeddings to the second trained machine learning model to determine imputed activity data associated with the patient. The system may determine if the patient belongs to one or more patient subgroups based on presence of the one or more relevant biomarkers. Specifically, if the imputed activity data associated with the patient indicates a presence of a relevant biomarker, the system can determine that the patient may belong to a patient subgroup associated with the biomarker. The system can identify a treatment for the patient based on the one or more biomarkers and known mechanism of action (MoA) of the treatment.

FIG. 14B illustrates an exemplary process for training and using the second machine learning model 1404b to impute gene-specific gene expression data (e.g., for approximating CNA values for each target gene). As described above, differential gene expression may provide a relatively strong approximation for copy number amplification because patients with a CNA of a respective target gene will often have a higher expression of that target gene. In the depicted example in FIG. 14B, training data 1402b including tile embeddings may be obtained by using the first machine learning model to generate low dimensional embeddings of histopathology images (e.g., from the first cohort) and paired with observed gene-specific gene expression data. Gene-specific gene expression levels may be determined via differential expression analysis between copy-number amplified and copy-number normal (e.g., diploid) subjects.

The data used for differential expression analysis may be preprocessed according to various preprocessing procedures. For instance, in some of the examples described herein (e.g., those described in additional detail below with reference to the Exemplary Studies section), augmented TCGA STAR+RSEM gene counts for 11,155 samples, generated from the Genomic Data Commons (GDC) standard pipeline and aligned to GRCh38, were obtained from the GDC portal and provided to the system. In some examples, a corresponding STAR+RSEM gene count matrix for at least a subset of the samples (e.g., 2,733 samples in at least one example) were prepared in cohort A. In some examples, transcript per million (TPM) matrices were be concatenated, filtered to genes with non-trivial expression (requiring TPM>1 in at least one subject), and subset to protein-coding genes from Gencode V43, resulting In a set of unique genes (e.g., 19,421 unique genes in at least one example).

In some examples, the resulting TPM matrix was log 2-transformed and then quantile normalized via the limma voom function in R. Subsequently, in some examples, edgeR's removeBatchEffects function was applied to regress out the cohort effect (TCGA vs. cohort A). In some examples, the resulting log 2(TPM) matrix was assessed for possible batch effects from sequencing instrument and sequencing center via principal component analysis and lmfit on potential batch drivers. No significant batch effects were identified in the examples described herein. This joint expression matrix was used in some examples as input for downstream analyses.

In some examples, differential expression analysis between copy-number amplified and copy-number normal (e.g., diploid) patients was performed using the limma voom package in R. In some examples, for each amplification, limma models (~CNA status (presence or absence of CNA status)+cohort related to cancer type) were fit to identify deferentially expressed genes with a false discovery rate (FDR)-corrected p-value (i.e. q-value)<0.01 and an absolute log 2 fold change>0.3. The gene expression values for each target gene may be paired with corresponding tile embeddings generated using the first trained machine learning model and used to train the second machine learning model for imputing gene-specific gene expression data.

In some examples, the second machine learning model 1404b is configured to make individual tile-level predictions, which are then averaged. Training model 1404b to predict on the tile-level rather than slide-level featurizations may enhance interpretability. For instance, having tile-level predictions may enable the generation and overlay of annotation maps, highlighting the regions of a slide driving the model's predictions. In some examples, second machine learning model 1404b is trained on bulk, rather than spatially resolved, molecular data, and second machine learning model 1404b learns spatial variation in tumor cell molecular markers that correlates with the regions identified as cancerous by blinded pathologist review, as demonstrated in the Exemplary Studies section below.

Additionally, or alternatively, the second machine learning model 1404b may be trained to impute molecular analyte activity based on an average of the featurization of one or more tiles and/or the second machine learning model 1404b may be equipped with an attention mechanism (e.g., a cross-tile spatial attention mechanism) allowing the model to make patient-level predictions while attending to spatially adjacent tiles. However, in some examples, configuring model 1404b to make individual tile-level predictions may outperform models configured with attention mechanisms and/or models trained to impute molecular analyte activity based on an average of the featurization of one or more tiles. The improved performance resulting from configuring the model to make individual tile-level predictions may be due to the fact that averaging before making predictions attenuates the signal and loses resolution.

The second trained model 1404b may be provided with input tile embeddings 1452b from a patient and generate output imputed molecular analyte activity data 1456b. In some embodiments, the input embedding data is obtained by providing imaging data of the patient to the first machine learning model. In the depicted example of FIG. 14B, the imputed molecular analyte activity data 1456a includes gene-specific gene expression values. The output may be a patient target matrix with values corresponding to the imputed expression of each target gene within a patient. As discussed above, the second machine learning model 1404b can be the second machine learning model described with reference to FIGS. 2A and 2B, and the imputed molecular analyte activity determined by model 1404b can be used in block 210 in FIG. 2B to determine a biomarker. The biomarkers determined at block 210 may thus include gene-specific gene expression values.

In some examples, a second training stage may be utilized to finetune second machine learning model 1404b for specialized tasks. In some examples, second machine learning model 1404b may be finetuned for predicting imputed molecular analyte activity data 1456b including gene-specific gene expression based on a subset of the training data. The subset of the training data may correspond to a patient attribute, which may include a specific cohort of patients, a disease, a biomarker, or a combination thereof. In some examples, second machine learning model 1404a may be finetuned during the second training stage to predict imputed molecular analyte activity data 1456b including gene-specific gene expression for a specific cohort of patients/subjects, a specific disease (e.g., type of cancer), a specific biomarker, or a combination thereof. Such fine-tuned models can provide improved performance for a specific prediction task (e.g., as shown in the MET case study below). Because of the extensive pre-training of the model, such fine-tuning might be feasible even from the small-scale cohorts available in phase 1/2 clinical trials.

Moreover, a similar process could be applied to fine-tune a model to a treatment-response data set for a drug with a relevant MOA, shifting the model towards better predicting patient response. As described above with reference to block 210, a variety of different clinical outcome prediction methods are available based on the imputed activity data. Any of those described above with reference to blocks 210-214, and with reference to FIG. 14A, may be used to predict clinical outcomes based on imputed expression values (e.g., a third machine learning model may be trained to determine an association between imputed activity data and clinical outcome data).

FIG. 14C illustrates an exemplary process for training and using the second machine learning model 1404c to impute gene-specific amplification signature values. In the depicted example in FIG. 14C, training data 1402c includes tile embeddings that may be generated by using the first trained machine learning model (e.g., first model 304) to generate low dimensional embeddings of histopathology images (e.g., from the first cohort). Tile embeddings may be paired with amplification signatures determined based on weighted expression levels of differentially expressed genes. For instance, a signature for each amplification may be constructed by taking the dot product of the differentially expressed genes with a set of weights. More specifically, for amplification k, suppose there were $J_k$ differentially expressed genes. Let $G_{ij}$ denote the expression level of gene j in subject i. The signature for subject i with respect to the $k^{th}$ amplification may be determined using:

$$S_{ik} = \sum_{j=1}^{J_k} w_{jk} G_{ij}.$$

The weight $w_{jk}$ may be the sign of the $\log_2$ fold change of gene j in amplification k scaled by the absolute $\log_{10}$ q-value. This scheme may afford more weight to genes where there is greater evidence of differential expression. A more positive signature $S_{ik}$ indicates that subject i has an expression profile consistent with amplification k, even if that subject did not have amplification of k based on copy number analysis. Accordingly, signature biomarkers were derived directly from the imputed RNA profiles, allowing for substitution of a hard-to-estimate (and potentially limited) biomarker with one that can be estimated much more robustly; other signatures, which combine RNA measurements in different ways, can be defined and evaluated similarly. Amplification signatures can be calculated from imputed expression levels. However, better performance may be obtained by developing machine learning models to directly impute the amplification signature (trained using labels derived from observed expression levels), such as model 1404c of FIG. 14C.

The tile embeddings may be obtained, for instance, by providing histopathology images from the first cohort to the first trained machine learning model to obtain a low-dimensional representation of each histopathology image and paired with corresponding signatures. Training data 1402c may be used to train the second machine learning model 1404c to predict patient/subject signature values given new input embedding data.

In some examples, the second machine learning model 1404c is configured to make individual tile-level predictions, which are then averaged. Training model 1404c to predict on the tile-level rather than slide-level featurizations may enhance interpretability. For instance, having tile-level predictions may enable the generation and overlay of annotation maps, highlighting the regions of a slide driving the model's predictions. In some examples, second machine learning model 1404b is trained on bulk, rather than spatially resolved, molecular data, and second machine learning model 1404b learns spatial variation in tumor cell molecular markers that correlates with the regions identified as cancerous by blinded pathologist review, as demonstrated in the Exemplary Studies section below.

Additionally, or alternatively, the second machine learning model 1404c may be trained to impute molecular analyte activity based on an average of the featurization of one or more tiles and/or the second machine learning model 1404c may be equipped with an attention mechanism (e.g., a cross-tile spatial attention mechanism) allowing the model to make patient-level predictions while attending to spatially adjacent tiles. However, in some examples, configuring model 1404c to make individual tile-level predictions may outperform models configured with attention mechanisms and/or models trained to impute molecular analyte activity based on an average of the featurization of one or more tiles. The improved performance resulting from configuring the model to make individual tile-level predictions may be due to the fact that averaging before making predictions attenuates the signal and loses resolution.

Once trained, the second trained model 1404c may be provided with input tile embeddings 1452c from a patient and output imputed molecular analyte activity data 1456c. In some embodiments, the input embedding data is obtained by providing imaging data of the patient to the first machine learning model. In the depicted example of FIG. 14C, the imputed molecular analyte activity data 1456c includes gene-specific amplification signature values. The output may be a patient matrix with values corresponding to an amplification signature of a patient for each target gene. As discussed above, the second machine learning model can be the second machine learning model described with reference to FIGS. 2A and 2B, and the imputed molecular analyte activity determined by model 1404c can be used in block 210 in FIG. 2B to determine a biomarker. The biomarkers determined at block 210 may thus include gene-specific amplification signature values.

In some examples, a second training stage may be utilized to finetune second machine learning model 1404c for specialized tasks. In some examples, second machine learning model 1404a may be finetuned during a second training stage to predict imputed molecular analyte activity data 1456c including gene-specific amplification signature(s) based on a subset of the training data. The subset of the training data may correspond to a patient attribute, which may include a specific cohort of patients, a disease, a biomarker, or a combination thereof. For instance, the second machine learning model may be finetuned for a specific cohort of patients/subjects, a specific disease (e.g., type of cancer), a specific biomarker, or a combination thereof. Such fine-tuned models can provide improved performance for a specific prediction task (e.g., as shown in the MET case study below). Because of the extensive pre-training of the model, such fine-tuning might be feasible even from the small-scale cohorts available in phase 1/2 clinical trials. Moreover, a similar process could be applied to fine-tune a biomarker predictive model to a treatment-response data set for a drug with a relevant MOA, shifting the model towards better predicting patient response.

As described above with reference to block 210, a variety of different clinical outcome prediction methods are available based on the imputed activity data. Any of those described above with reference to blocks 210-214, and with reference to FIGS. 14A and 14B, may be used to predict clinical outcomes based on imputed amplification signature values (e.g., a third machine learning model may be trained to determine an association between imputed activity data and clinical outcome data).

Tile images used to generate the embeddings referred to above for any of the models depicted in FIGS. 14A-14C may be obtained from stained whole slide images. For example, a set of hematoxylin and eosin (H&E)-stained whole slide images (WSIs) (e.g., a set of 30,032 images in some examples described herein), corresponding to a set of unique patients (e.g., 11,428 unique patients in some examples described herein), may downloaded from a data source such as GDC. The tissue-bearing foreground of the image may be extracted, and low-frequency super-cellular artifacts such as tissue folds, out-of-focus regions, and pen markings may be removed, for instance using WSI Spectral Thresholding for Artifact Removal (WSI-STAR) as described in U.S. Application No. 63/548,141 titled "SYSTEMS AND METHODS FOR ARTIFACT DETECTION AND REMOVAL FROM IMAGE DATA", which is incorporated by reference in its entirety for all purposes. To account for differences in staining protocols across studies centers, color channels may be normalized, for instance, using Macenko's method. Each slide may be divided into non-overlapping 256 by 256 tiles at a resolution of 1 μm per pixel (MPP), and tiles may be filtered to those with at least 90% foreground. In some examples, this resulted in 180 million individual tiles. In some examples, WSIs for 1,000 patients of cohort A were processed in the same manner, resulting in 8 million tiles.

Embeddings may be generated from the aforementioned image tiles using an embedding model as described throughout. For instance, a vision transformer (ViT)-type model may be trained on randomly selected 256×256 1 MPP tiles from TCGA using the self-supervised distillation with no labels (DINO) algorithm. Given a collection of unlabeled images, DINO trains a student network (e.g., the ViT) to match the output of a teacher network. This task is made more challenging by the fact that the student and teacher networks receive different "views" of the input image. Training may be monitored by periodically evaluating the utility of embeddings extracted from the teacher network for several downstream tasks, including cancer subtype classification and overall survival prediction, within an independent validation set of tiles (e.g., 100,00 tiles in some examples described herein). Tile-level embeddings generated by the final model may serve as the inputs to downstream modeling tasks such as those described with reference to FIGS. 14A-14C.

In some examples, the models described herein (e.g., 1404b 1404c) may achieve considerably higher performance at predicting RNA and even higher performance at predicting amplification signatures relative to predicting CAN directly (e.g., using model 1404a), as illustrated below in the Exemplary Experimental Studies section. This higher performance may derive from several sources. First, in some examples quantitative traits offer enhanced statistical power over binary or ordinal traits such as CNA, since continuous data capture more granular phenotypic variation, and provide meaningful information across the entire set of individuals, significantly increasing the effective sample size. Second, multiple studies have shown that copy number amplification is only one mechanism by which clinically relevant activation of a gene or pathway might be achieved, and other mechanisms might converge on the same pathway, resulting in the same phenotypic consequences. Use of alternative genome-wide signatures captures a broader range of these "CNA phenocopy" mechanisms and avoids creating artificial and biologically meaningless distinctions in the training set, which may serve to confuse the ML model. Moreover, there are indications that patients lacking a mutation in a particular target but with a transcriptional pattern concordant with that mutation may benefit from the same class of treatments as a patient harboring a genuine amplification.

Figure 15:
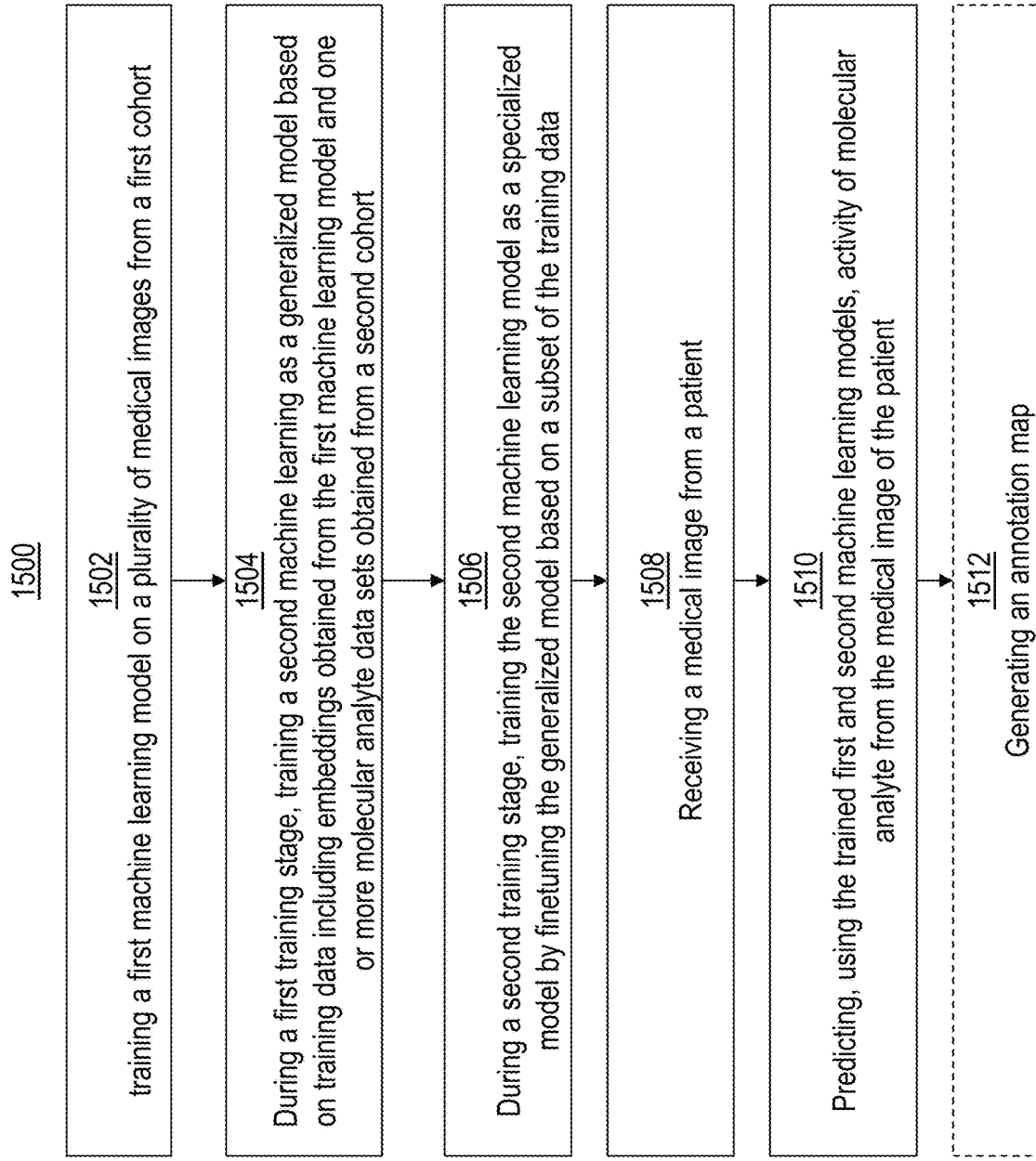
FIG. 15 illustrates an exemplary method for predicting molecular analyte activity using a model trained as a specialized model by finetuning a generalized model based on a subset of training data in accordance with some embodiments.

FIG. 15 illustrates an exemplary method 1500 for predicting molecular analyte activity using a model trained as a specialized model by finetuning a generalized model based on a subset of training data. At block 1502, a first machine learning model may be trained on a plurality of medical images from a first cohort. The first machine learning model may be an embedding model that includes any of the features of the embedding model(s) described throughout. The first machine learning model may be trained to generate tile-level embeddings based on a plurality of tiles of the medical image. The tile-level embeddings may be input into the second machine learning model described below. In some examples, at least a subset of the tile level embeddings are averaged prior to being input into the second module of the machine learning model.

At block 1504, during a first training stage, a second machine learning model may be trained as a generalized model based on training data including embeddings obtained from the first machine learning model and one or more molecular analyte data sets obtained from a second cohort. The second machine learning model may be trained during the first training stage to predict imputed molecular analyte activity, as described with reference to the second machine learning model throughout. The second machine learning model may include any of the features described throughout the disclosure herein.

At block 1506, during a second training stage, the second machine learning model may be trained as a specialized model by finetuning the generalized module based on a subset of the training data. The subset of training data may correspond to a patient attribute, which may be a cohort of patients/subjects (e.g., any set of individuals), a disease (e.g., lung cancer, breast cancer, colorectal cancer), a biomarker, or any combination thereof. Case studies demonstrating the improved performance of specialized models created by finetuning a generalized model are provided below under the subheadings Use Case: MET Case Study, Use Case: TACSTD2 Case Study, and Use Case: Cabozantinib Case Study.

At block 1508, a medical image may be received from a patient. The patient may include the patient attribute to which the subset of training data corresponds (e.g., a particular type of cancer). At block 1510, the first and second machine learning models may predict activity of a molecular analyte from the medical image of the patient. The predicted activity of the molecular analyte may be utilized to identify a biomarker, predict patient response to a therapeutic intervention, etc., as described throughout the disclosure.

At block 1510, an annotation map of the predicted activity of the molecular analyte may be generated. The annotation map may be overlayed on the medical image. The map may include a visualization distinguishing normal tissue from tumor tissue, for instance, as illustrated in FIGS. 33A-37.

Exemplary Experimental Studies: Foundational Models and Specialized Models

An exemplary study employed data from The Cancer Genome Atlas (TCGA), a public research resource that includes genetic, molecular, and histological data from 11K patient and over 20K primary tumors across 33 cancer types. Molecular and histological data from an additional 2.6K patients were obtained from a commercially available multi-center cancer research resource (cohort A). Target genes were identified as described above. A commercial pharmaceutical database was queried to identify drugs whose therapeutic class was labeled as antibody-drug conjugate (ADC), T-cell engager, or antibody, including both mono-specific and multi-specific antibodies. For ADCs and T-cell engagers, drugs at any stage of development were retained, while for antibodies (a larger class), drugs whose development had ceased were excluded. The overall list of drugs was filtered to those with specified targets. Each remaining drug was mapped to a HGNC gene symbol, and the union of all gene symbols was taken, resulting in 352 unique targets.

Three sets of neural network models were trained via 8-fold cross validation to predict gene expression, copy number amplification, and gene signatures from H&E tile embeddings of dimension 768. The training was performed in pytorch (2.1.0). Two major architecture classes were used. The first, a 4-layer sequential network consisting of linear layers interspersed with ReLU and dropout layers, is reproduced below. Training and evaluation data was fed to the model in batches of size 2000.

```
net = torch.nn.Sequential(
    torch.nn.Linear(768, 512),
    torch.nn.ReLU( ),
    torch.nn.Dropout(0.6),
    torch.nn.Linear(512, 256),
    torch.nn.ReLU( ),
    torch.nn.Dropout(0.6),
    torch.nn.Linear(256, 256),
    torch.nn.ReLU( ),
    torch.nn.Dropout(0.6),
    torch.nn.Linear(256, N_GENES))
```

The second class of model extended the first to include cross-tile attention, building on the transMIL architecture, using batch size of 1 with gradient accumulation for 400 batches. Optimization was performed using Adam, starting with a learning rate of 1e-4, which decayed exponentially (gamma=0.96) after 2 consecutive epochs of no improvement. An early stopping threshold of 3 or 4 (depending on the model) consecutive epochs with no improvement in validation loss was utilized to indicate training completion.

For regression tasks (predicting target expression or the amplification signature), the objective was Huber loss with delta=1.0. For classification tasks (predicting copy number amplification, elevated target expression, or elevated amplification signature), the objective was binary cross entropy loss, with the minority (positive) class inversely weighted by class prevalence. When performing classification for elevated target expression or amplification signature, the positive class was defined as those patients exceeding the 95% percentile (p95). Label smoothing was applied during training, with p0-p50 assigned a label of 0; p50-p90 a label of 0.1; p90-p95 a label of 0.9; and p95-p100 a label of 1.0. Label smoothing was not possible in the case of CNA labels, which are intrinsically binary.

Building on the promising results from the expression and signature classification foundation models, specialized models were trained to predict MET expression and signature within NSLC and COAD (colon adenocarcinoma) cohorts. Training was performed on tile-level H&E embeddings using the architecture:

```
net = torch.nn.Sequential(
    torch.nn.Linear(768, 32),
    torch.nn.Tanh( ),
    torch.nn.Linear(32,1))
```

Inputs to the model were restricted to H&E data from the cohort of interest (NSLC or COAD), keeping the same subject splits as in the foundation models to avoid contamination, but pruning out training and evaluation subjects from other cohorts. Training for the specialized models was performed via a binary cross entropy loss using the Adam optimizer with a weight decay of 1-4, a learning rate 0.001, and early stopping enabled after three consecutive epochs of no reduction in evaluation loss. Binarization and label smoothing was performed as described above for the foundation models.

Model performance was evaluated via an 8-fold cross-validation procedure, where the model was trained on 7 folds and the evaluated on the held-out fold. For regression tasks, the evaluation metrics included the Pearson and Spearman correlations. For classification tasks, the evaluation metrics included the area under the precision-recall curve (AUPRC) and the area under the receiver operating characteristic (AUROC). While the models emit tile-level predictions, tiles are clustered within patients, and the labels are patient level. Performance metrics were aggregated from tile to patient level by taking the mean. For pan-cancer analyses, performance is assessed across all patients, whereas for stratified analyses, performance is assessed first within each cancer type, than averaged across cancer types. The stratified analysis restricts to cancer types with at least 100 available patients to ensure the performance metrics can be estimated with reasonable precision. Due to the low prevalence (e.g. <1%) of certain CNAs, for stratified CNA analyses, on targets where at least 3 patients harbored CNAs in a given cancer type are included.

Curated OS labels for patients in The Cancer Genome Atlas TCGA were obtained from J Liu, T Lichtenberg, KA Hoadley, et al. An integrated tcga pan-cancer clinical data resource to drive high-quality survival outcome analytics. Cell, 173(2):400-416, 2018. Within cohort A (2.6K patients obtained from a commercially available multi-center cancer research resource), therapy specific OS was defined as the time from therapy onset to the patient's death. In instances where no death report was available, patients were censored at the time of last follow-up. Analyses were performed in cohort A, where more-detailed clinical data were available. Hazard ratios quantifying the association between OS and predicted biomarkers were estimated via the Cox proportional hazards model, adjusting for the age at diagnosis, age at disease staging, pre-treatment stage, sex, cancer type, metastatic status, number of unique prior therapies, and time from diagnosis to treatment with the therapy of interest. Patients were partitioned into two groups ("high" and "low") on the basis of their amplification signature, but without reference to their survival. The significance of differential survival between these groups was assessed via the HR from the Cox model. Adjusted Kaplan-Meier curves were calculated using the direct standardization approach.

Results: Biomarker Prediction

CNA Prediction

Figure 16:
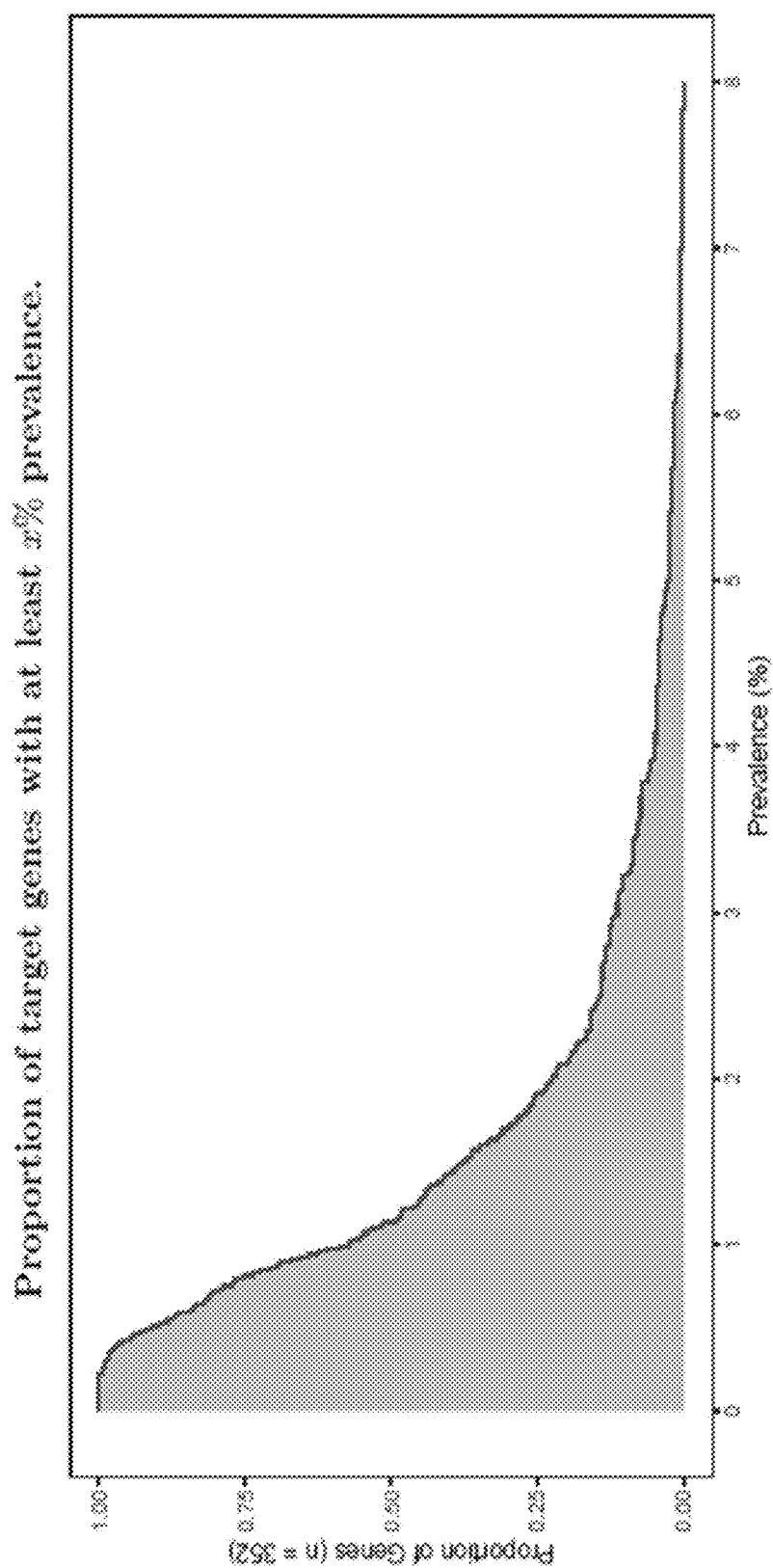
FIG. 16 shows a proportion of target genes with at least a threshold prevalence in accordance with some embodiments.

Copy number amplifications (CNAs) were called for each of 352 target genes (hereafter, "targets"). Within the overall cohort (n=14, 007), the median amplification prevalence was 1.1% (range: 0.2% to 7.8%; also see FIG. 16). Multi-task, binary-outcome models were developed to simultaneously predict CNA status for all 352 targets. The inputs to these prediction models were embeddings of 256 by 256, 1 μm per pixel tiles from digital, whole-slide histopathology images (WSIs). Patient-level predictions are obtained by taking the mean across all tiles within a patient's WSIs. Here and throughout, patient predictions are generated using an 8-fold cross-validation (CV) procedure such that the model which generates a patient's prediction does not see that patient's data during training.

Figure 17A:
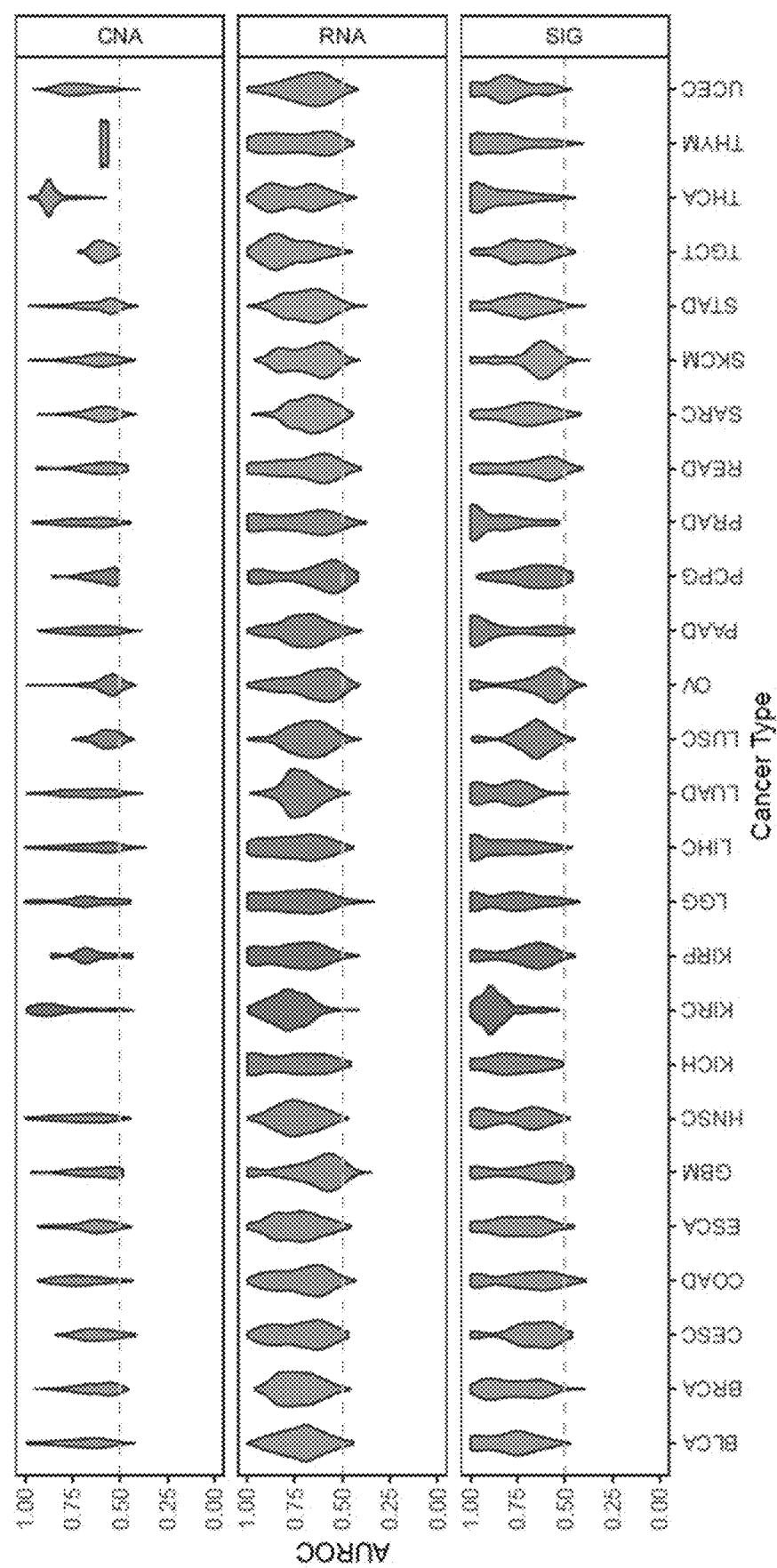
FIG. 17A illustrates a distribution of area under the receiver operating characteristic (AUROCs) in accordance with some embodiments.
Figure 17B:
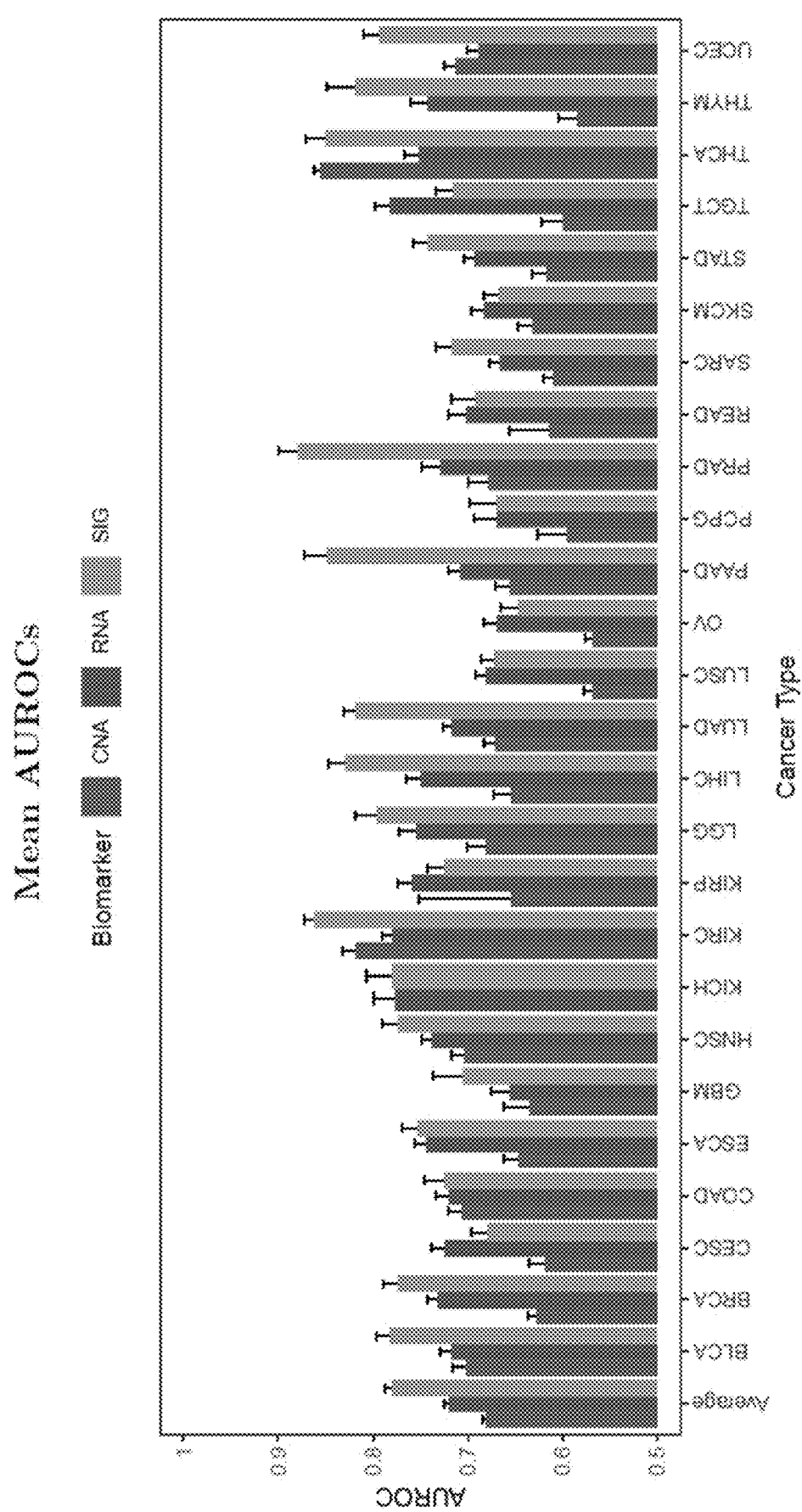
FIG. 17B illustrates mean area under the receiver operating characteristic (AUROCs) in accordance with some embodiments.
Figure 18A:
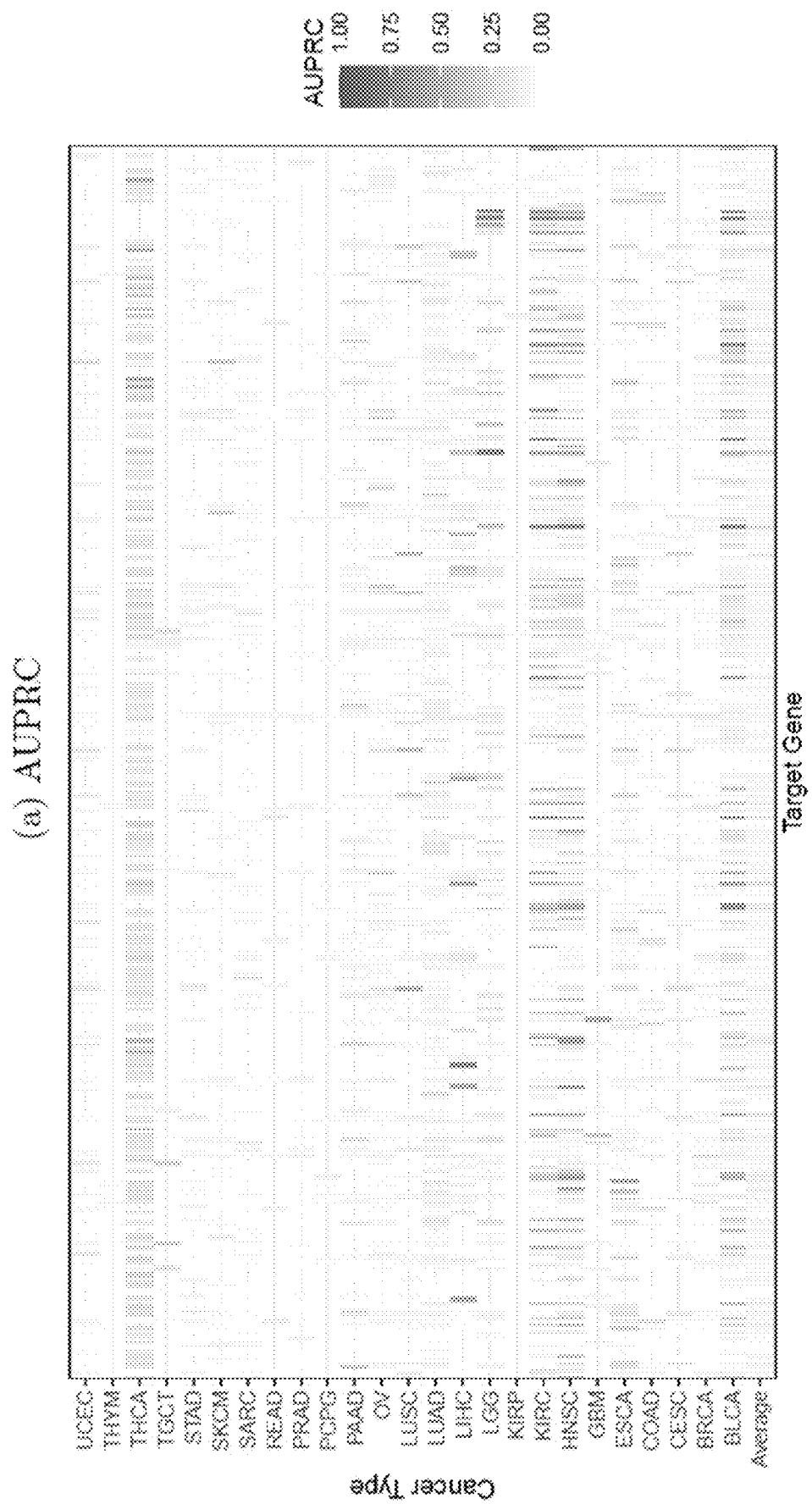
FIGS. 18A and 18B illustrate the area under the receiver operating characteristic (AUROC) for predicting copy number amplifications (CNAs) stratified by cancer type in accordance with some embodiments.
Figure 18B:
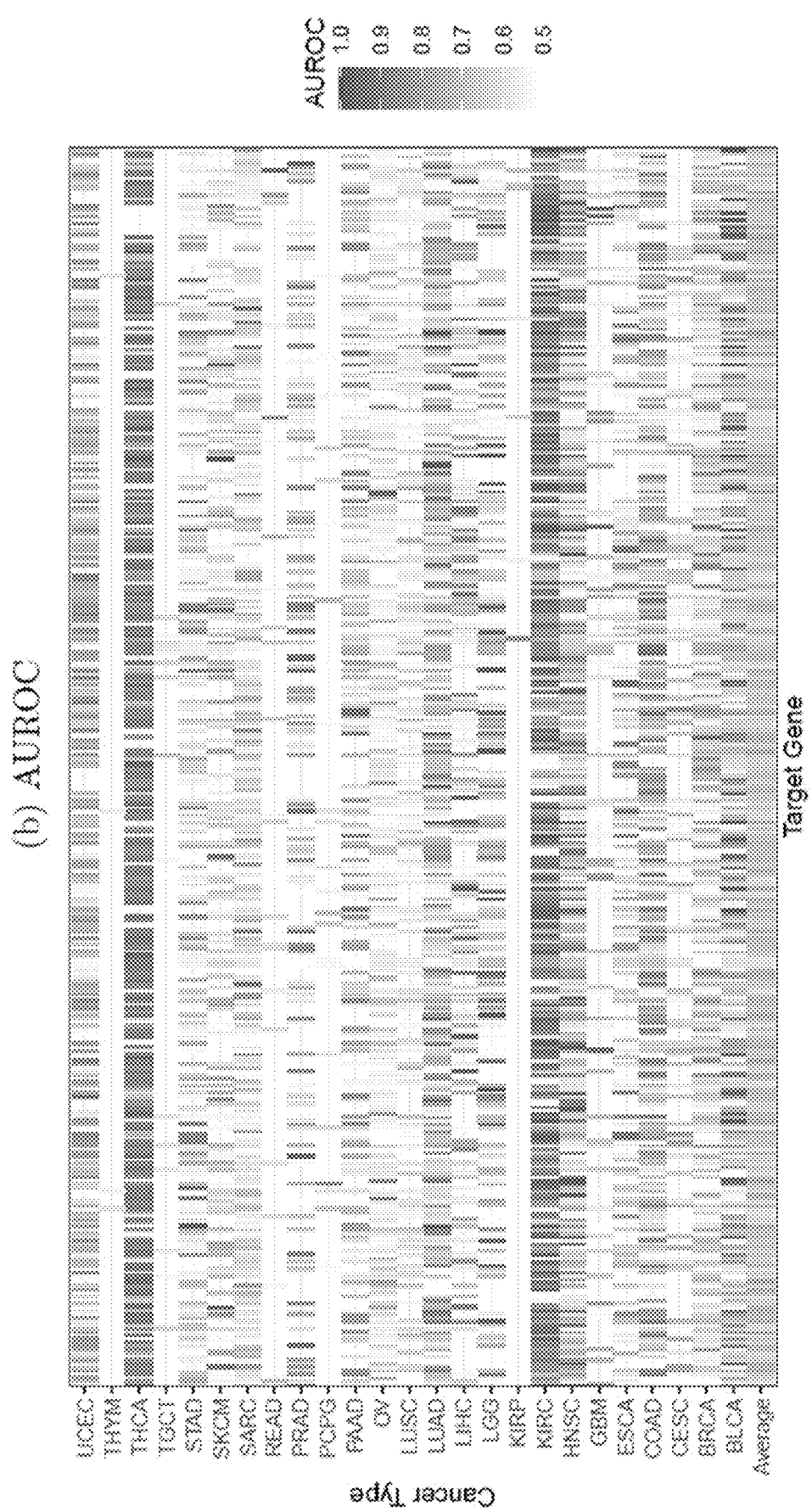

FIGS. 17A and 17B presents a cross-modality comparison of binary digital biomarker prediction quality, stratified by cancer-type. More specifically, FIGS. 17A and 17B respectively illustrate the distribution of AUROCs, across targets, and mean AUROC in each of 26 cancer types with at least 100 patients. Performance was evaluated at the patient level in a held-out evaluation set and averaged across 8 cross-validation folds. Due to the low prevalence of certain CNAs, when assessing performance within cancer types, metrics are only reported for those targets where at least 3 patients harbored amplifications. The mean and distribution are shown across up to 352 target genes. For CNA, the task was to predict whether the patient harbored an amplification. For target expression (RNA) and the amplification signature (SIG), the task was to predict whether the patient's expression/signature level exceeded the 95th percentile. Error bars are 95% confidence intervals. The mean AUROC across targets is summarized in Table 1. The heatmaps in FIGS. 18A and 18B present, for each target, the area under the receiver operating characteristic (AUROC) for predicting CNAs, stratified by cancer type. Performance was evaluated at the patient level in a held-out evaluation set and averaged across 8 cross-validation folds. Metrics are only presented where at least 3 patients within a cancer type harbored a mutation in the target gene. The pan-cancer analysis evaluates performance across all available patients.

The stratified analysis evaluates performance separately in each cancer type, then takes the mean across cancer types. The distinction between these approaches is that the stratified analysis evaluates how well the model learns to differentiate CNA risk within cancer types, whereas the pan-cancer analysis examines how well the model learns to differentiate risk both within and between cancer types. To demonstrate the within-cancer-type performance, the performance within two specific cohorts of interest, breast and colorectal, is also presented.

TABLE 1

Overall performance for biomarker prediction from digital histopathology. Performance is evaluated at the patient level in a held-out evaluation set and averaged across 8 cross-validation folds. The 3 types of biomarkers are copy number amplification (CNA), target expression level (RNA), and amplification signature score (SIG). For binary classification, the area under the receiver operating characteristics (AUROC) is shown. For regression, Spearman correlation between the observed and predicted values is shown.

| Cohort | N | Biomarker | AUROC | Spearman |
|---|---|---|---|---|
| Pan-cacner | 14,007 | CNA | 0.734 | |
| Pan-cacner | 14,007 | RNA | 0.853 | 0.628 |
| Pan-cacner | 14,007 | SIG | 0.897 | 0.665 |
| Stratified | 12,328 | CNA | 0.680 | |
| Stratified | 12,328 | RNA | 0.719 | 0.318 |
| Stratified | 12,328 | SIG | 0.779 | 0.333 |
| Breast | 1,455 | CNA | 0.627 | |
| Breast | 1,455 | RNA | 0.731 | 0.372 |
| Breast | 1,455 | SIG | 0.773 | 0.418 |
| Colorectal | 629 | CNA | 0.707 | |
| Colorectal | 629 | RNA | 0.720 | 0.324 |
| Colorectal | 629 | SIG | 0.724 | 0.293 |

Expression Prediction

Figure 19:
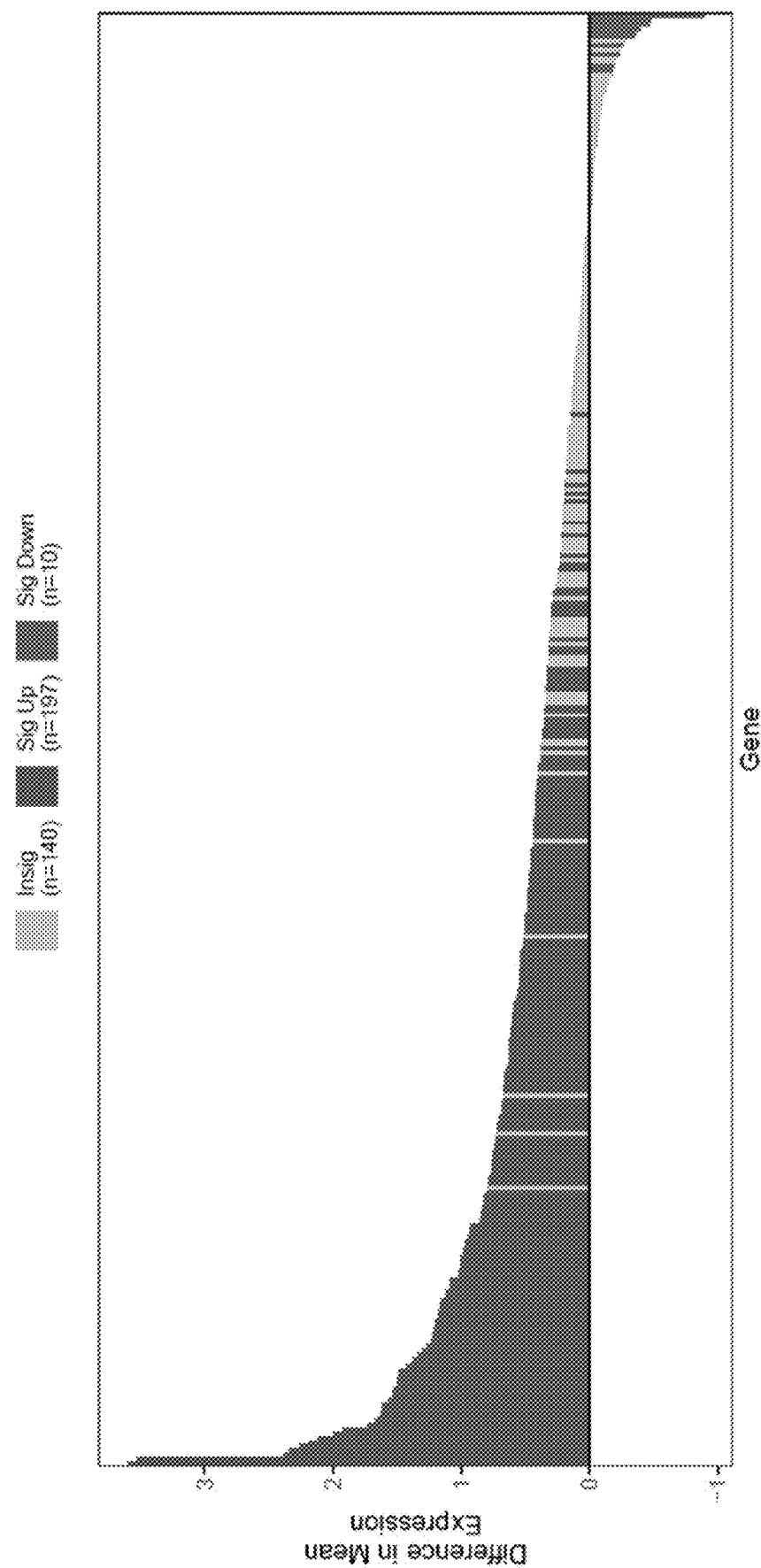
FIG. 19 illustrates the differences in expression between patients with and without CNAs across 347 targets with available RNA in accordance with some embodiments.

Previous work has associated copy number amplification with differential gene expression across cancer types. FIG. 19 presents the differences in expression between patients with and without CNAs across 347 targets with available RNA. Of these, 207 (59.7%) were significantly differentially expressed, the vast majority (197/207; 95.2%) having higher mean expression in patients with amplifications. It was hypothesized that, by providing a continuous supervisory signal, modeling RNA would enable training of more accurate biomarker prediction models.

Figure 20:
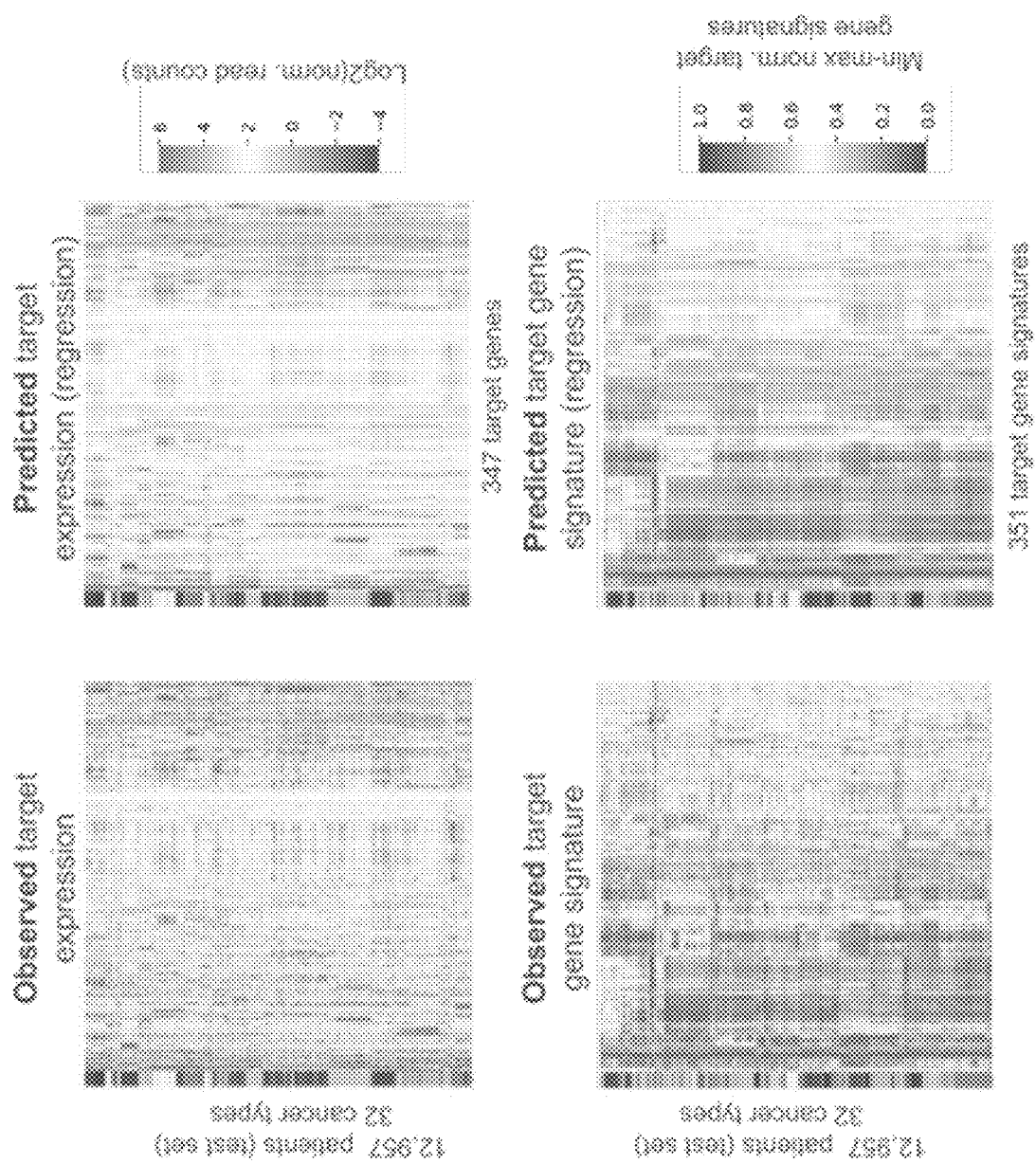
FIG. 20 illustrates observed and predicted expression matrices pan-cancer in accordance with some embodiments.

Accordingly multi-task, continuous-outcome models were developed to simultaneously predict, on the basis of histopathology tile embeddings, the expression levels for 347 of the 352 targets with available RNA. FIG. 20 compares the observed and predicted expression matrices pan-cancer. Predictions were generated via cross-validation, such that a patient is not used to train the model that generates their predictions. The matrices on the left show the observed gene expression or signature matrix. The matrices on the right shown prediction based on digital pathology. The color within the matrices describes the level of expression or magnitude of the amplification signature. The color bar on the left of each plot annotates cancer type.

Figure 21:
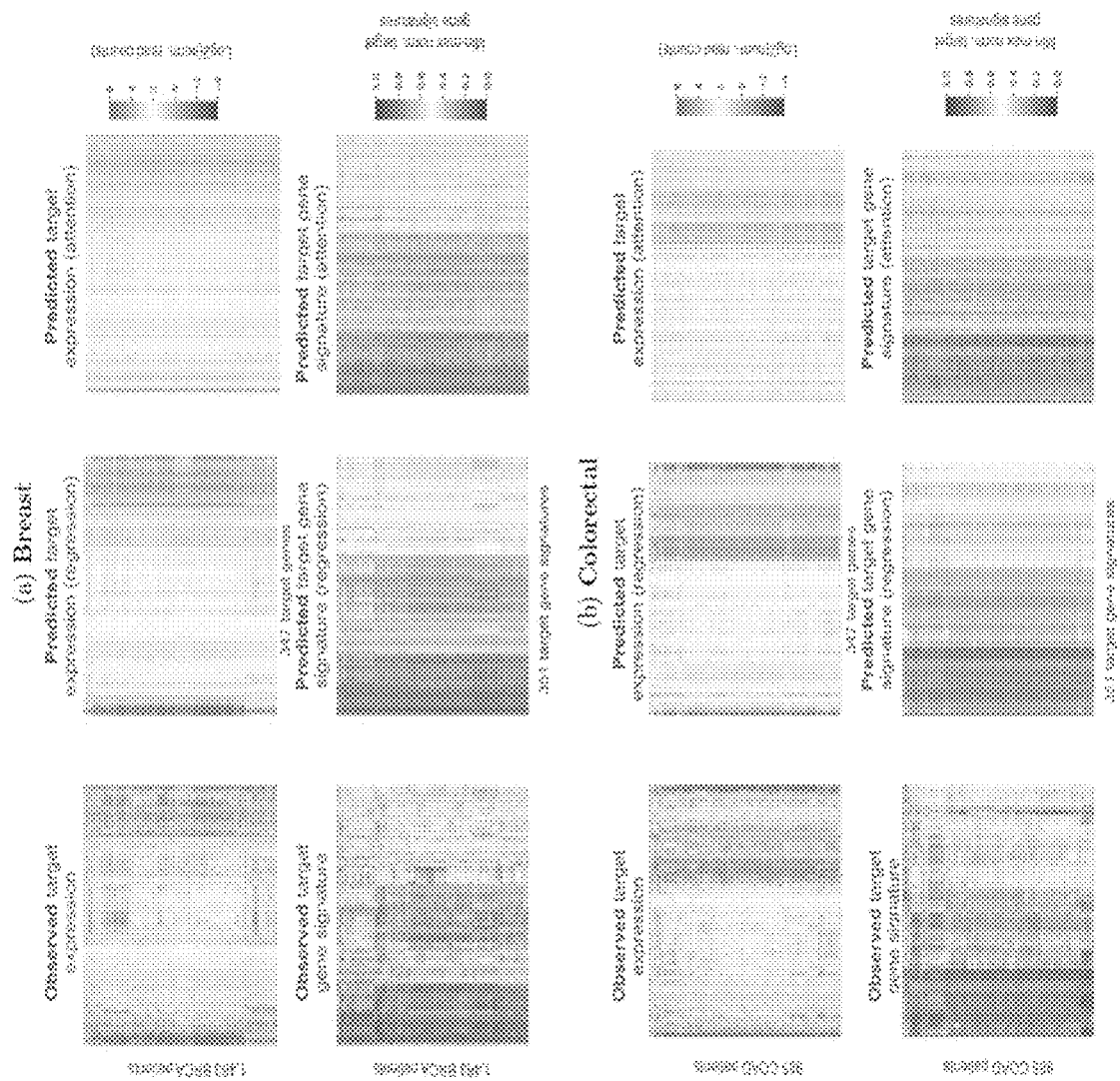
FIG. 21 illustrates a comparison of observed expression/signature matrices with those predicted on the basis of histopathology, stratified by cancer type in accordance with some embodiments.
Figure 22A:
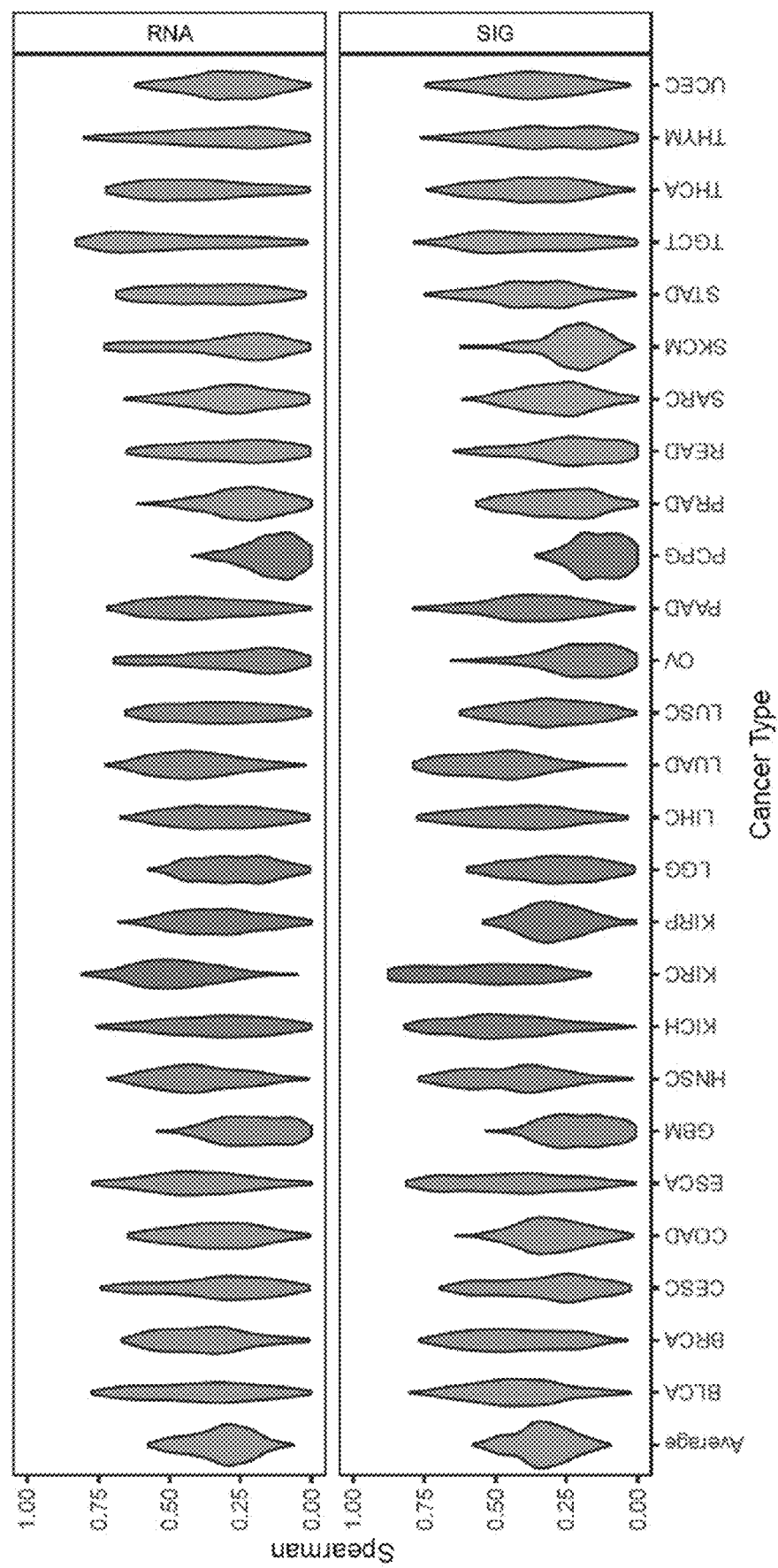
FIG. 22A presents a distribution of correlations, across targets, between a patient's observed and predicted expression levels in accordance with some embodiments.
Figure 22B:
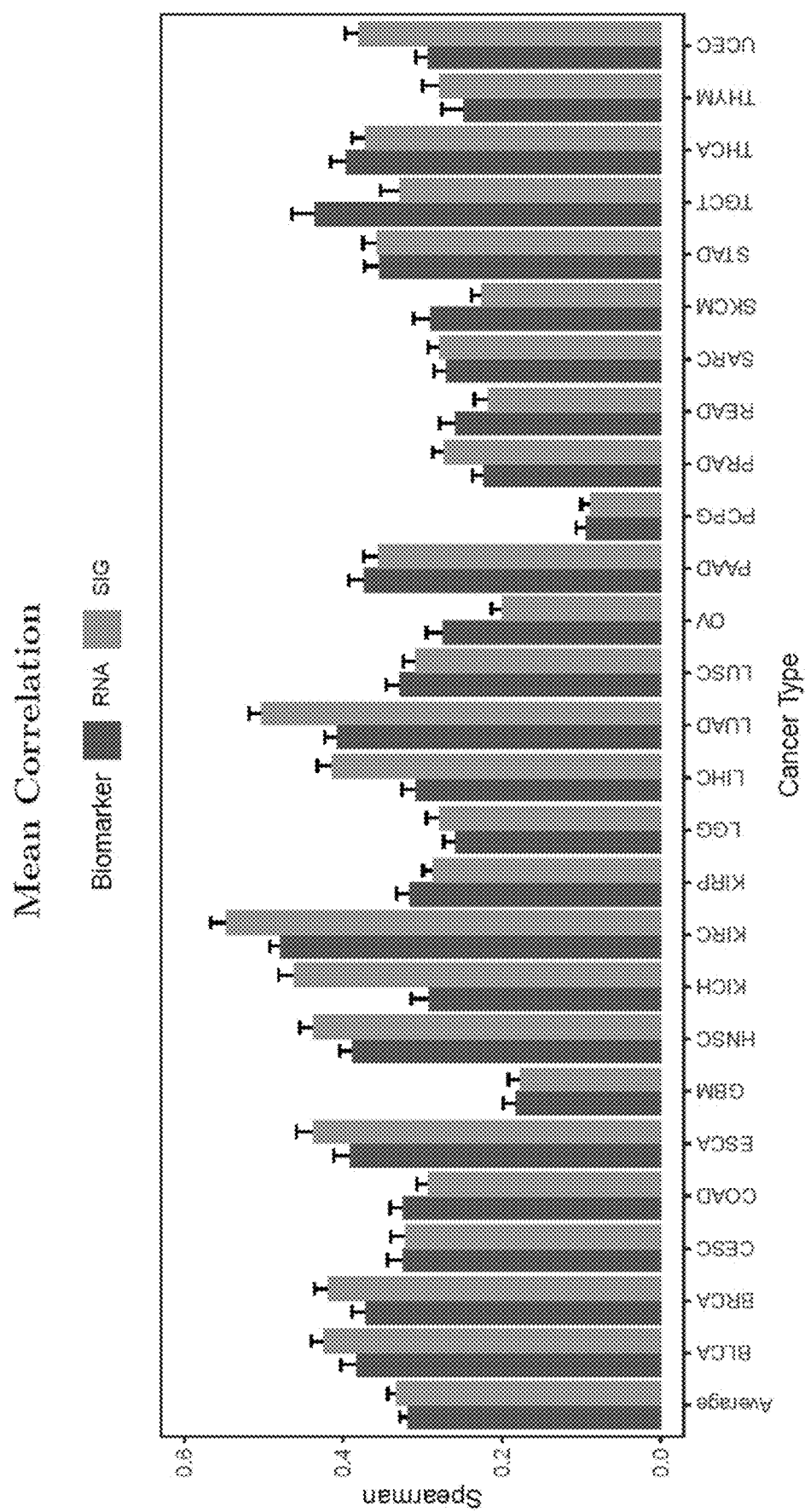
FIG. 22B illustrates mean correlation by cancer type in accordance with some embodiments.
Figure 23A:
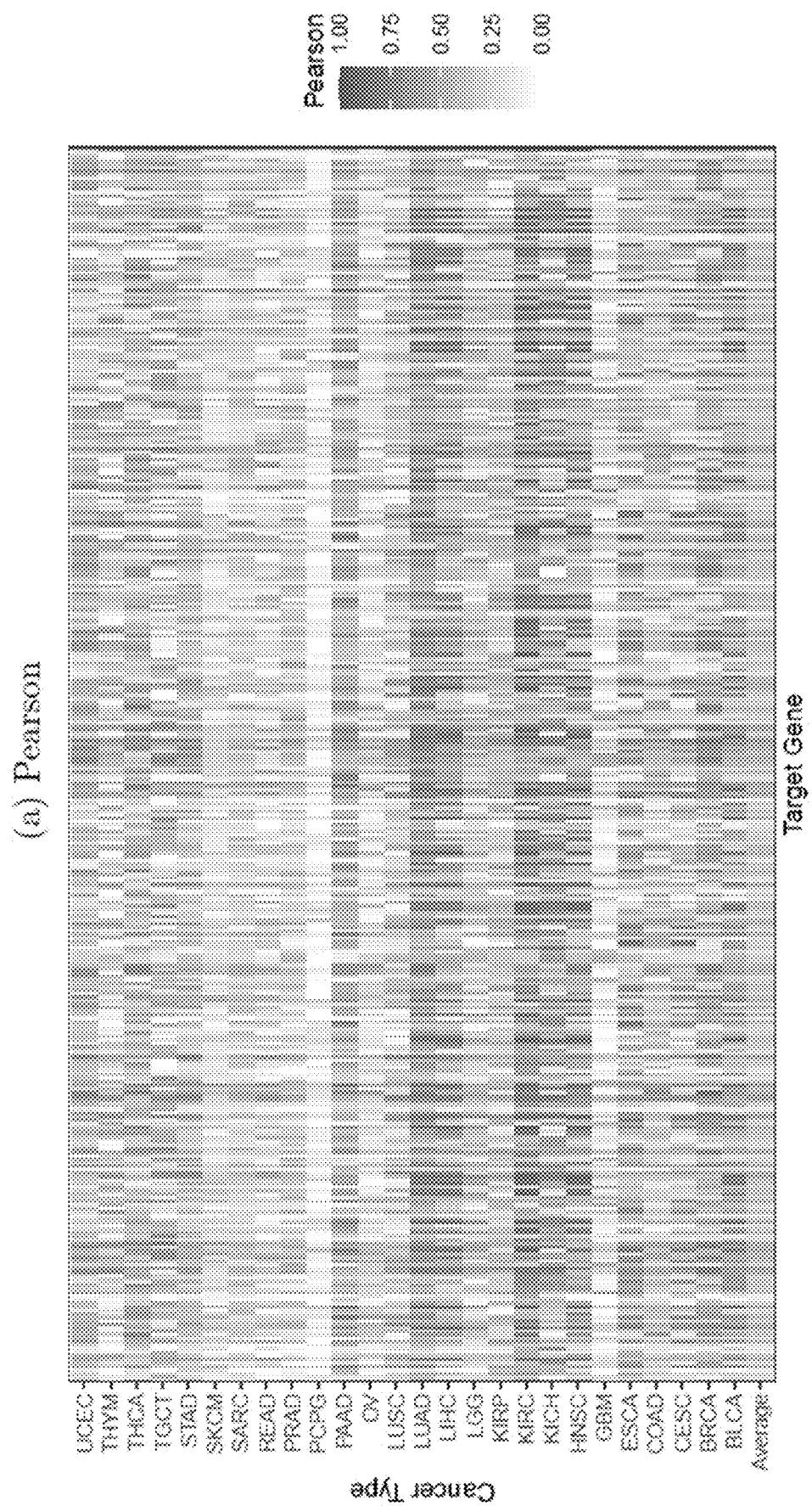
FIGS. 23A and 23B illustrate prediction of amplification signature from digital histopathology, stratified by cancer type in accordance with some embodiments.
Figure 23B:
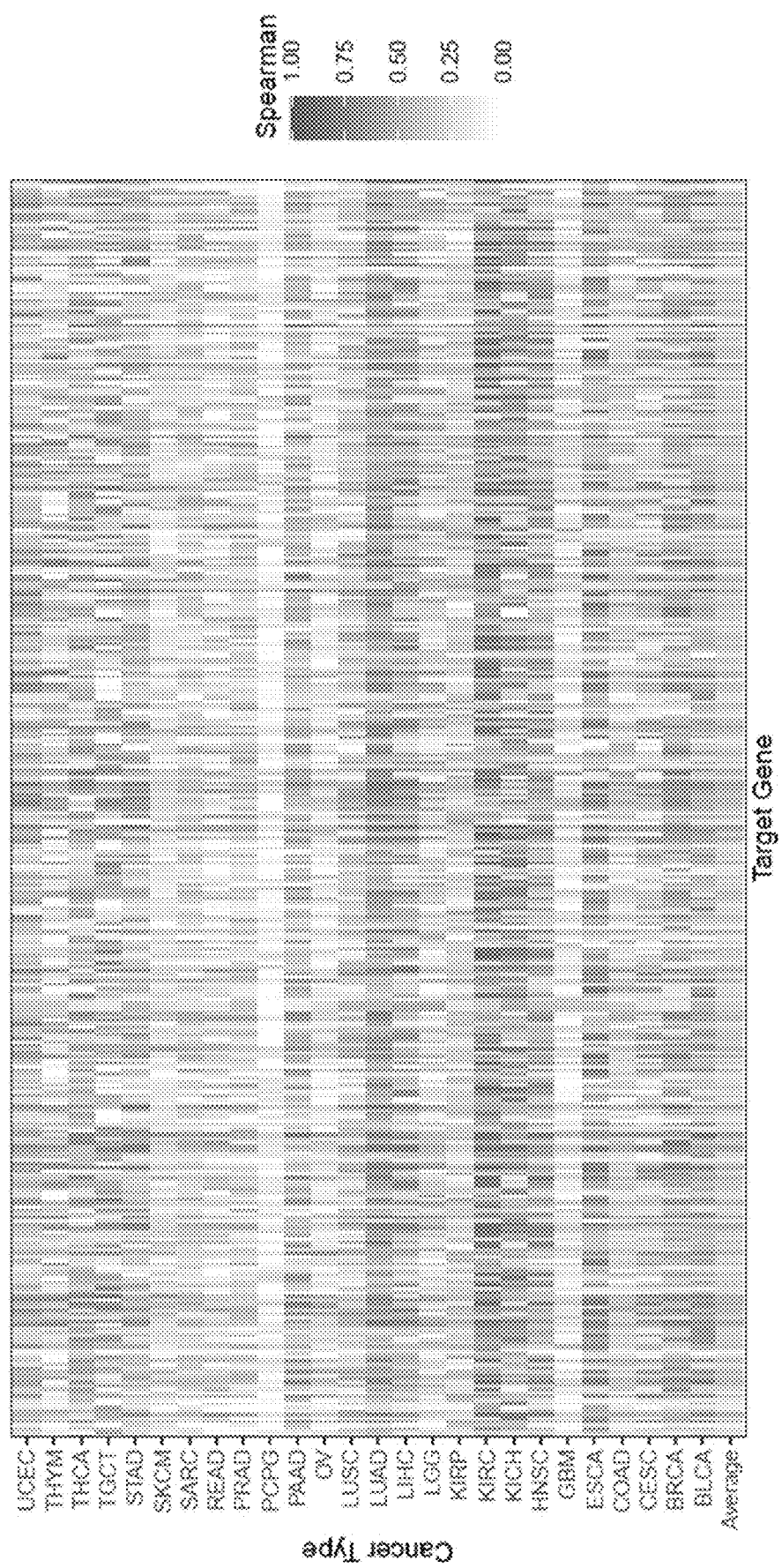

Analogous matrices subset to breast and colorectal cancer are presented in FIG. 21, which depicts a comparison of observed expression/signature matrices with those predicted on the basis of histopathology, stratified by cancer type. Predictions were generated via cross-validation, such that a patient is not used to train the model that generates their predictions. The matrices on the left show the observed gene expression or signature matrix. The matrices in the center show the best-performing prediction model. The matrices on the right show a spatially-aware model that includes tile-level transformer-based attention. The color bar on the left of each plot annotates cancer type. FIG. 22A presents the distribution of correlations, across targets, between a patient's observed and predicted expression levels, and FIG. 22B illustrates the mean correlation by cancer type. Specifically, patient level predictions were first generated via 8-fold CV, then for each target, the correlation between the observed and predicted expression levels was calculated across patients. Metrics were calculated separately in each cancer type with ≥100 patients. The distributions are shown across up to 352 target genes. For RNA, the task is to predict the normalized log 2 expression level. For SIG, the task is to predict the min-max normalized amplification signature. Pan-cancer, the mean cross-validated Spearman correlation was 62.8%, and stratifying by cancer type, the mean Spearman correlation was 31.8% (Table 1). As expected, correlations are higher in the pan-cancer analysis, where the model benefits from learning to distinguish differences both within and between cancer types. FIGS. 23A and 23B presents the correlations for all targets broken down by cancer type. Specifically, FIGS. 23A and 23B show prediction of amplification signature from digital histopathology, stratified by cancer type. Performance was evaluated at the patient level in a held-out evaluation set and averaged across 8 cross-validation folds.

Figure 24A:
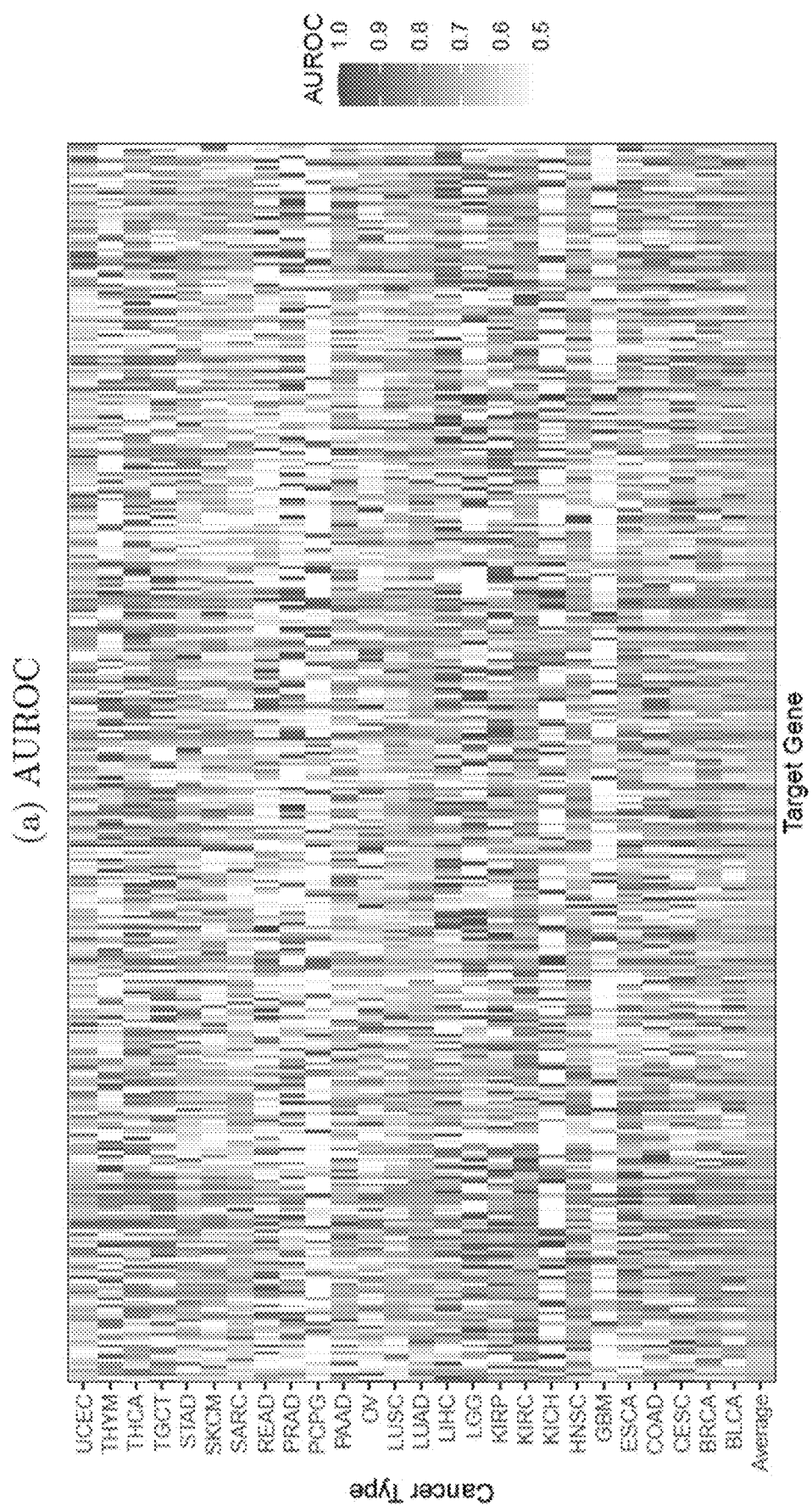
FIGS. 24A and 24B illustrate AUROC and AUPRC of elevated target expression from digital histopathology, stratified by cancer type in accordance with some embodiments.
Figure 24B:
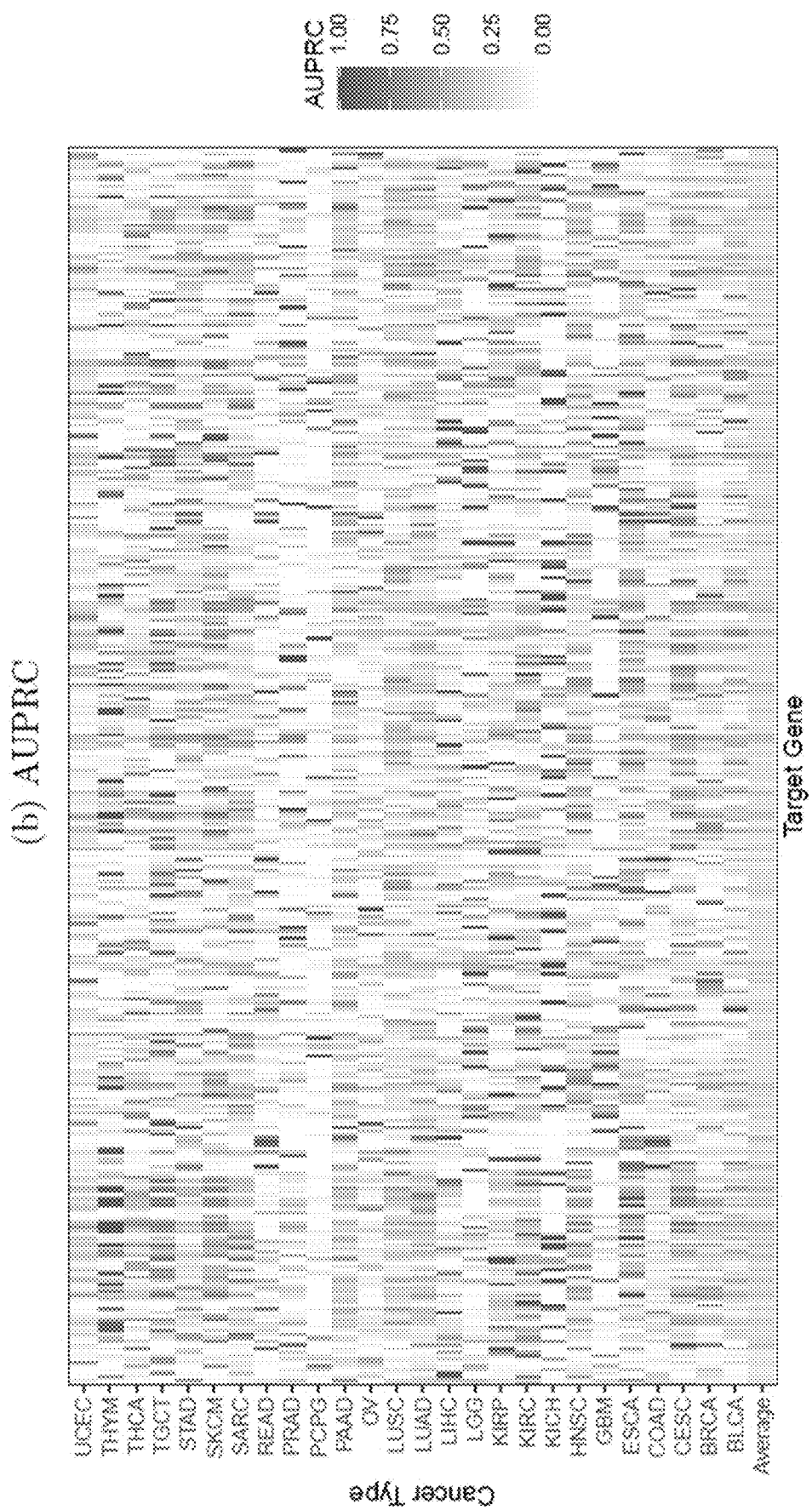

To enable comparison with the binary CNA prediction task, the expression of each target was dichotomized at its 95th percentile (p95), and multi-task binary-outcome models were developed to predict whether a patient's expression exceeded the p95, suggesting that the target was highly expressed. FIGS. 24A and 24B present results for all targets stratifying by cancer type. Specifically, FIGS. 24A and 24B show AUROC and AUPRC of elevated target expression from digital histopathology, stratified by cancer type. A patient was defined to have elevated expression if their expression level exceeds the 95th percentile for a given target. Performance was evaluated at the patient level in a held-out evaluation set and averaged across 8 cross validation folds. FIGS. 17A and 17B presents the distributions and means for each cancer type. As expected, elevated target expression was generally more predictable than CNA status. As shown in Table 1 the pan-cancer AUROC increased from 73.4% to 85.3%, and the stratified AUROC increased from 70.0% to 71.9%.

Amplification Signatures

Figure 25:
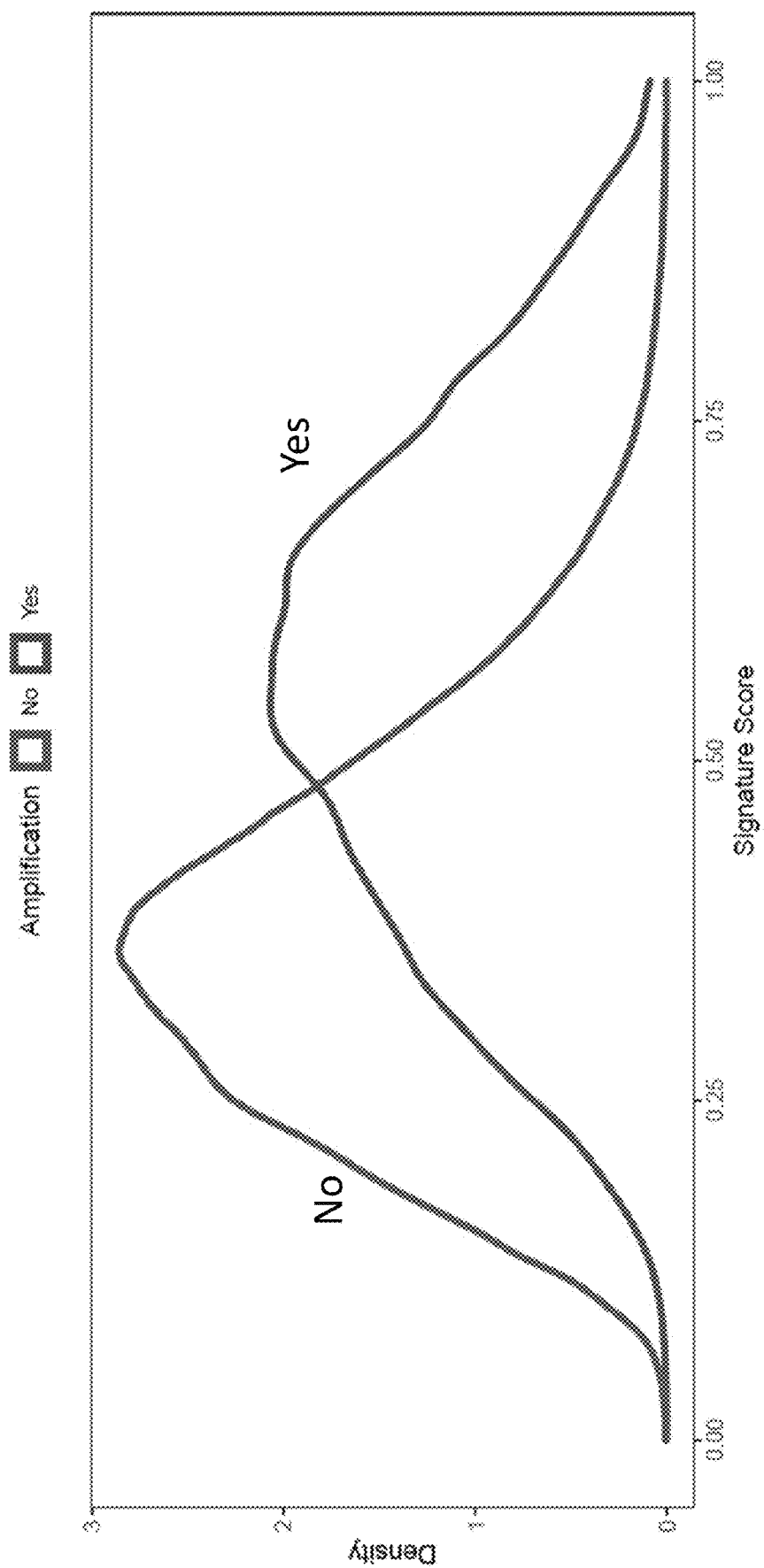
FIG. 25 illustrates a distribution of signature scores in patients with and without amplifications in accordance with some embodiments.
Figure 27:
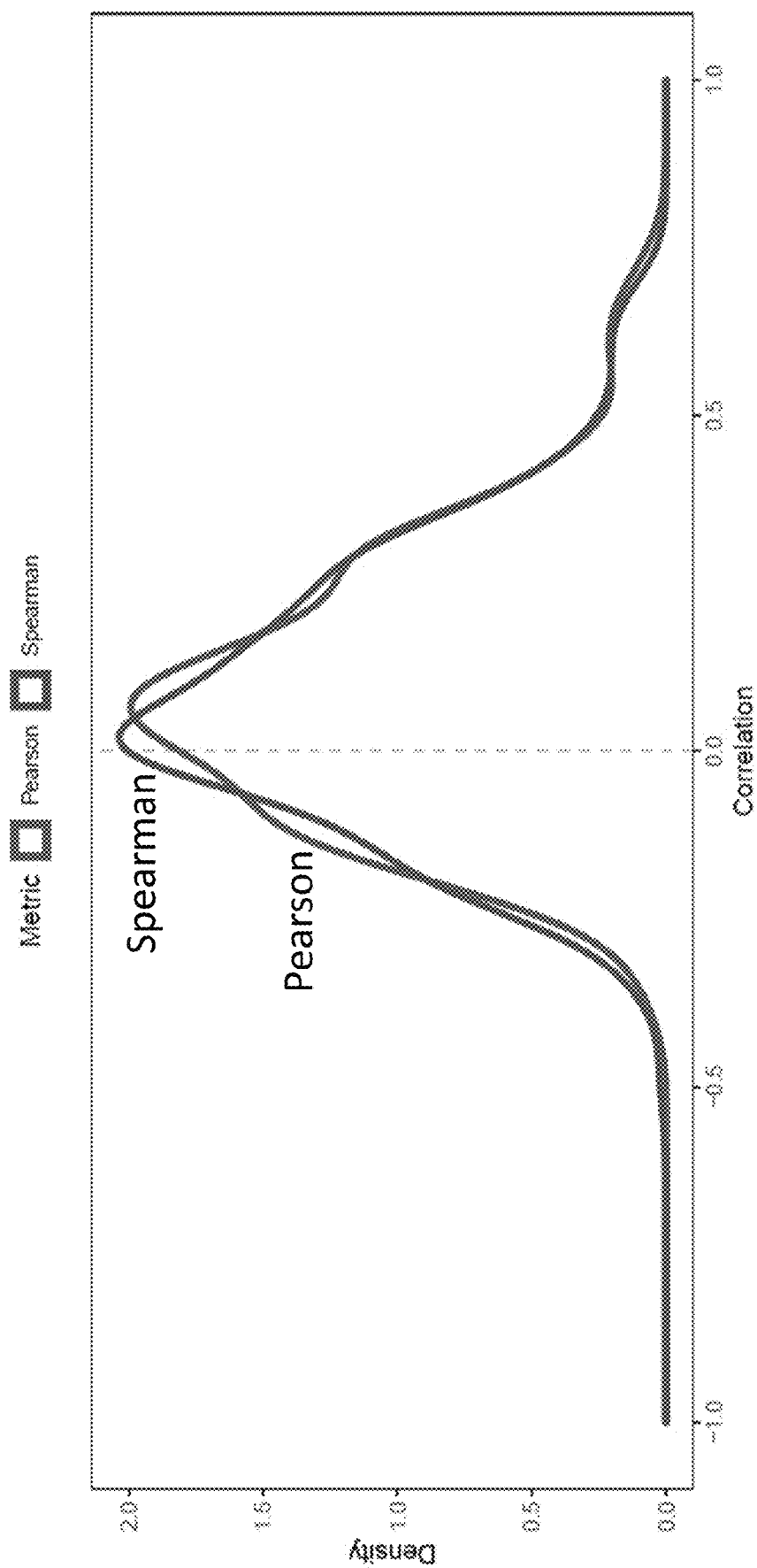
FIG. 27 illustrates the distribution of correlations, across targets and pan-cancer, between the amplification signature and expression of the amplified gene in accordance with some embodiments.

As discussed above (see FIG. 19), there is only modest concordance between CNA and differential expression. Accordingly, a broader transcriptional signature capturing changes in expression beyond those of the target gene alone was developed that was expected to provide a better predictor of target CNA. For each of the 352 targets, all genes differentially expressed between patients with and without amplifications were identified, and the differentially expressed genes were utilized to construct an RNA-based amplification signature (for 1 gene, no differentially expressed genes were identified). The amplification signature is a linear combination of expression levels weighted by the magnitude of evidence for differential expression. Signatures were min-max normalized to the unit interval for ease of comparison. FIG. 25 presents the distribution of signature scores in patients with and without amplifications. Shown is the average distribution across up to 351 amplification signatures. Relative to those without amplifications, the mean signature scores of patients with amplifications were 46.3% higher (FIG. 26). FIG. 26 shows mean signature scores in patients with (cases) and without (controls) amplifications. The mean was calculated across up to 351 amplification signatures. For all 351 amplification signatures, there was at least nominally significant evidence, via the Wilcoxon rank-sum test, of differential scores between patients with and without CNAs (median P-value: $1.4 \times 10^{-}$ 27). FIG. 27 depicts the distribution of correlations, across targets and pan-cancer, between the amplification signature and expression of the amplified gene. For each of 352 targets, the correlation was calculated across 14K subjects. Shown are the distributions of the 352 correlations. In general, the correlation was low, with median R2 of only 2.0% (FIG. 28). FIG. 28 shows squared correlation between the amplification signature and expression of the amplified gene, pan-cancer. For each of 352 targets, the correlation was calculated pan-cancer.

Building on work predicting target expression, multi-task, continuous outcome models were developed, analogous to the expression models, for predicting the 351 amplification signatures from histopathology tile embeddings. FIGS. 22A and 22B presents the distribution of correlations, across targets, between a patient's observed and predicted amplification signatures, and the mean correlation by cancer type. As shown in Table 1 above, predictions of the amplification signature were, on average, more accurate than predictions of target expression. Pan-cancer, the mean cross-validated Spearman correlation was 66.5%, and stratifying by cancer type, the mean Spearman correlation was 33.3% (Table 1). FIGS. 23A and 23B presents the correlations for all targets broken down by cancer type.

Figure 29:
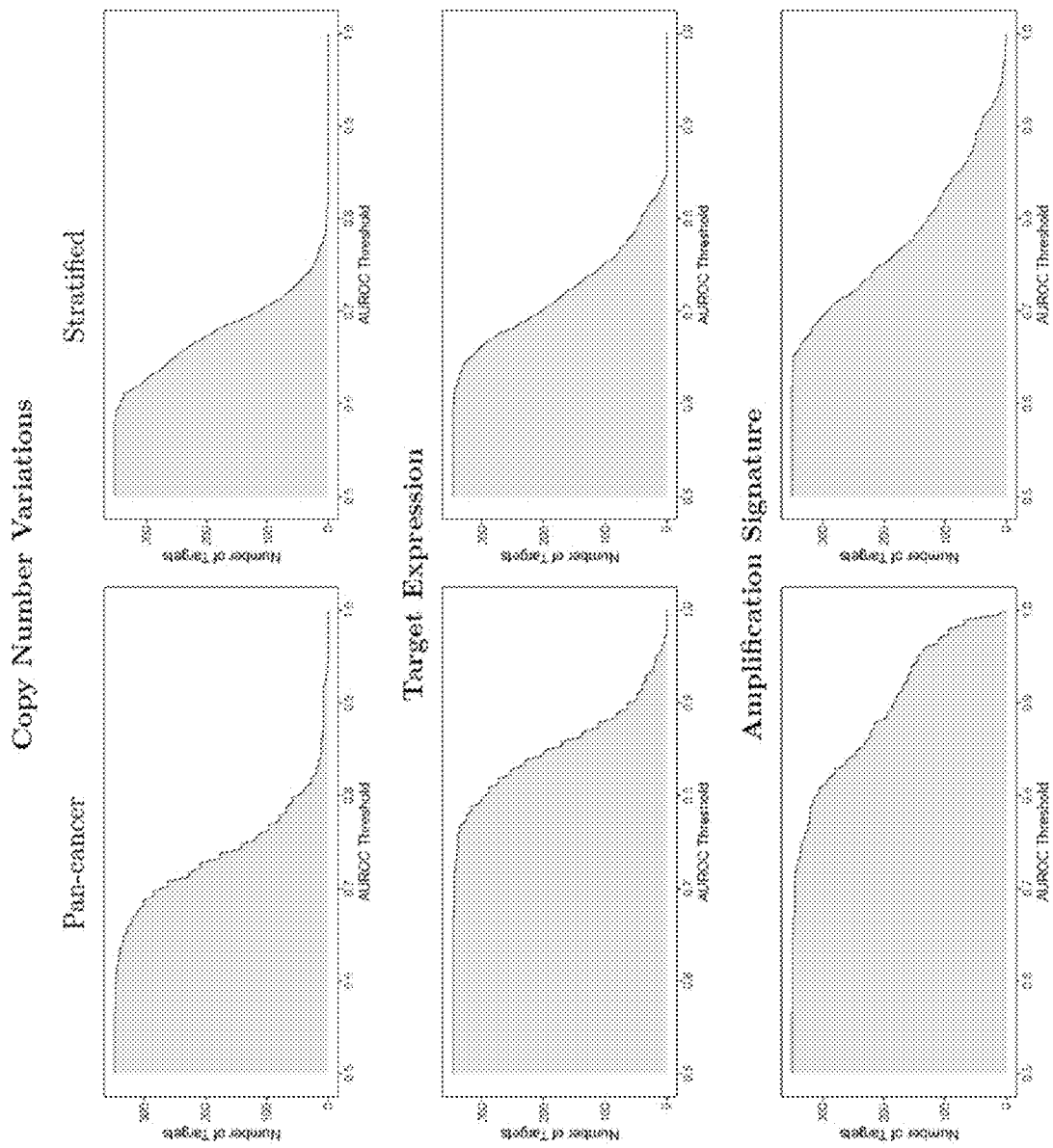
FIG. 29 illustrates the number of targets predicted with an AUROC exceeding a given threshold for the CNA, target expression, and amplification signature binary classification tasks in accordance with some embodiments.

A binary prediction task was also created, wherein the goal was to predict whether a patient harbored an elevated amplification signature, by dichotomizing each amplification signature at its p95. The distribution and mean AUROC across target, stratified by cancer type, are shown in FIGS. 17A and 17B. Pan-cancer, the mean AUROC was 89.7%, and stratified by cancer type, the mean AUROC was 77.9% (Table 1). FIG. 29 presents the number of targets predicted with an AUROC exceeding a given threshold for the CNA, target expression, and amplification signature binary classification tasks. Performance was evaluated at the patient level in a held-out evaluation set and averaged across 8 cross-validation folds. For the pan-cancer evaluation (left), the AUROC is calculated across all patients. For the stratified evaluation (right), the AUROC is calculated separately within each cancer type, then averaged across cancer types. For copy number amplification, the task was to predict whether the patient harbored an amplification. For target expression and the amplification signature, the task was to predict whether the patient's expression/signature level exceeded the 95th percentile. FIG. 30 summarizes the counts exceeding various cutoffs. For example, CNAs in 142 targets, elevated expression in 339 targets, and an elevated signature in 335 targets can be predicted with AUROC exceeding 0.75, pan-cancer. The corresponding counts for the stratified analysis are 25, 97, and 201 for CNA, expression, and signature, respectively. Note that achieving an AUROC of 0.75 or greater in the stratified analysis is a considerably higher bar, as this requires the model to differentiate risk within each cancer type, and do so effectively across many cancer types.

Use Cases

The utility of the model(s) were assessed in a number of distinct applications. Since the study design was based on a set of therapeutically relevant targets, a target driven perspective was taken in exploring use cases.

Use Case: MET Case Study

The first target evaluated was MET, a target for which there are multiple therapies available and under development. Copy number alteration of MET has been associated with worse overall survival across tumor types, and specifically in non-small-cell lung cancer. The standard assessment of whether a patient is eligible for a MET-targeting therapy utilizes an IHC-based biomarker; indeed, the ADC telisotuzumab vedotin has obtained FDA Breakthrough Therapy Designation for patients with high levels of MET overexpression. However, MET IHC has been shown to have poor concordance with MET CNA. Additionally, it is well established that mechanisms other than CNA that drive MET overexpression often also give rise to worse outcomes, and are generally much more common than amplification events. For example, in NSCLC, MET overexpression is found in 25%-75% of cases, whereas amplification occurs only in about 4%. Therefore, there is ample opportunity for the development of better biomarkers for identifying patients eligible for MET-targeting therapies.

Figure 31A:
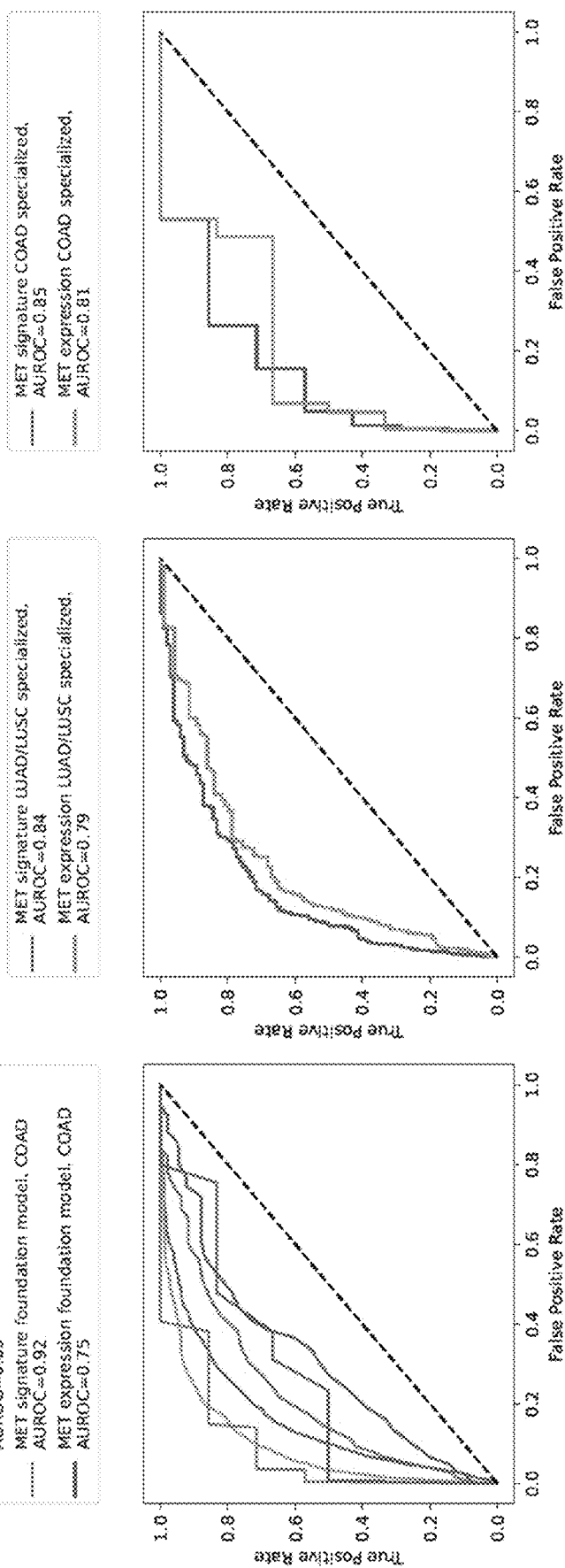
FIG. 31A illustrates performance of models trained to predict overexpression or an elevated amplification signature, performance when the model is further specialized for prediction within NSCLC, and performance of a model trained for colorectal cancer prediction, in the case of MET, in accordance with some embodiments.

The prevalence of MET amplifications in the overall cohort evaluated is 1.8%. The performance of the core (non-specialized) models was first investigated, as described above, predicting MET overexpression and an elevated MET amplification signature. As shown in FIG. 31A, pan-cancer, an AUROC of 0.91 was achieved for predicting MET overexpression, and of 0.84 was achieved for predicting an elevated amplification signature. FIG. 31A shows performance of models trained to predict overexpression or an elevated amplification signature from the foundation model's embeddings (left), the center shows the performance when the model is further specialized for prediction within NSCLC, and the right shows performance of a model trained for colorectal cancer prediction, in the case of MET. Within NSCLC, the pan-cancer model achieved AUROCs of only 0.69 and 0.78 for predicting overexpression and an elevated amplification signature respectively.

It was reasoned that model performance within specific cohorts could be improved by specializing the models (e.g., by training the predictive component of the model on the specific cohorts). Indeed, when models were trained within NSCLC patients specifically, an AUROC of 0.58 was obtained for predicting MET amplification, 0.79 was obtained for overexpression, and 0.84 was obtained for predicting an elevated amplification signature. The model was also able to predict quantitative MET expression with correlation of 0.38. In work done contemporaneously with the work described herein, K Ingale, S H Hong, J S K Bell, et al. *Prediction of met overexpression in non-small cell lung adenocarcinomas from hematoxylin and eosin images*. arXiv, 2023. preprint, similarly predict MET overexpression in NSCLC. Ingale et al., were able to train on a much larger cohort of NSCLC patients—605 MET+ patients versus 38 for the study described herein—but used the typical supervised training approach with a single-task model. Their method achieved an AUROC of 0.74 (compared to the AUROC of 0.79 for overexpression prediction above achieved by the models described herein), but in an artificially balanced test cohort, with equal numbers of cases and controls. In this regime, the approach described herein provided an AUROC of 0.87. Tests were also conducted to determent whether the biomarkers described herein have the potential to increase the set of patients with predicted increased MET activity. Indeed, whereas MET CNA identified only 38 NSCLC patients, MET RNA overexpression identified 72 patients, and the MET amplification signature identified 88 patients.

The pan-cancer approach described herein can also be used to identify new opportunities for biomarker deployment. In particular, the analysis revealed a strong performance in predicting MET in colorectal cancer. Although MET amplification is rare in colorectal cancer, previous work has noted that MET overexpression is more common, and is prognostic of poorer survival outcomes. Therefore, a specialized model was similarly trained for colorectal cancer. As shown in FIG. 31A, this model achieves an AUROC of 0.81 for predicting MET overexpression, and of 0.85 for predicting an elevated amplification signature.

Use Case: TACSTD2 Case Study

Antibody-drug conjugates that target the protein encoded by TACSTD2, known as trophoblast antigen 2 (TROP2), are under active development by several companies. Thus far, Trodelvy (sacituzumab govitecan) has been approved in urothelial cancer and breast cancer (HR+HER2− and TNBC) with active development in NSCLC, among other indications. Similarly, Dato-DXd (datopotamab deruxtecan) is actively being pursued in breast cancer and NSCLC. As an oncology target, TROP2 is of interest due to its expression in many solid tumors and limited expression in normal tissues. Moreover, multi-study meta-analyses have shown that over-expression of TACSTD2 was associated with poor overall survival and reduced disease-free survival.

Leveraging the pan-cancer approach described herein, findings indicated that elevated TACSTD2 expression was predicted pan-cancer with an AUROC of 0.85, in BRCA with an AUROC of 0.63, and in NSCLC with an AUROC of 0.75, as expected. However, the pan-cancer foundation model also suggests predictive power in several additional cancer types, including pancreatic (AUROC: 0.79), stomach (AUROC: 0.89), and thyroid (AROC: 0.73). Previous work has suggested that TROP2 over-expression occurs in these cancer types. Others have also recently reported preclinical evidence of tumor reduction using another TROP2-targeting ADC in xenograft mouse models of pancreatic cancer, consistent with the findings described herein.

Figure 31B:
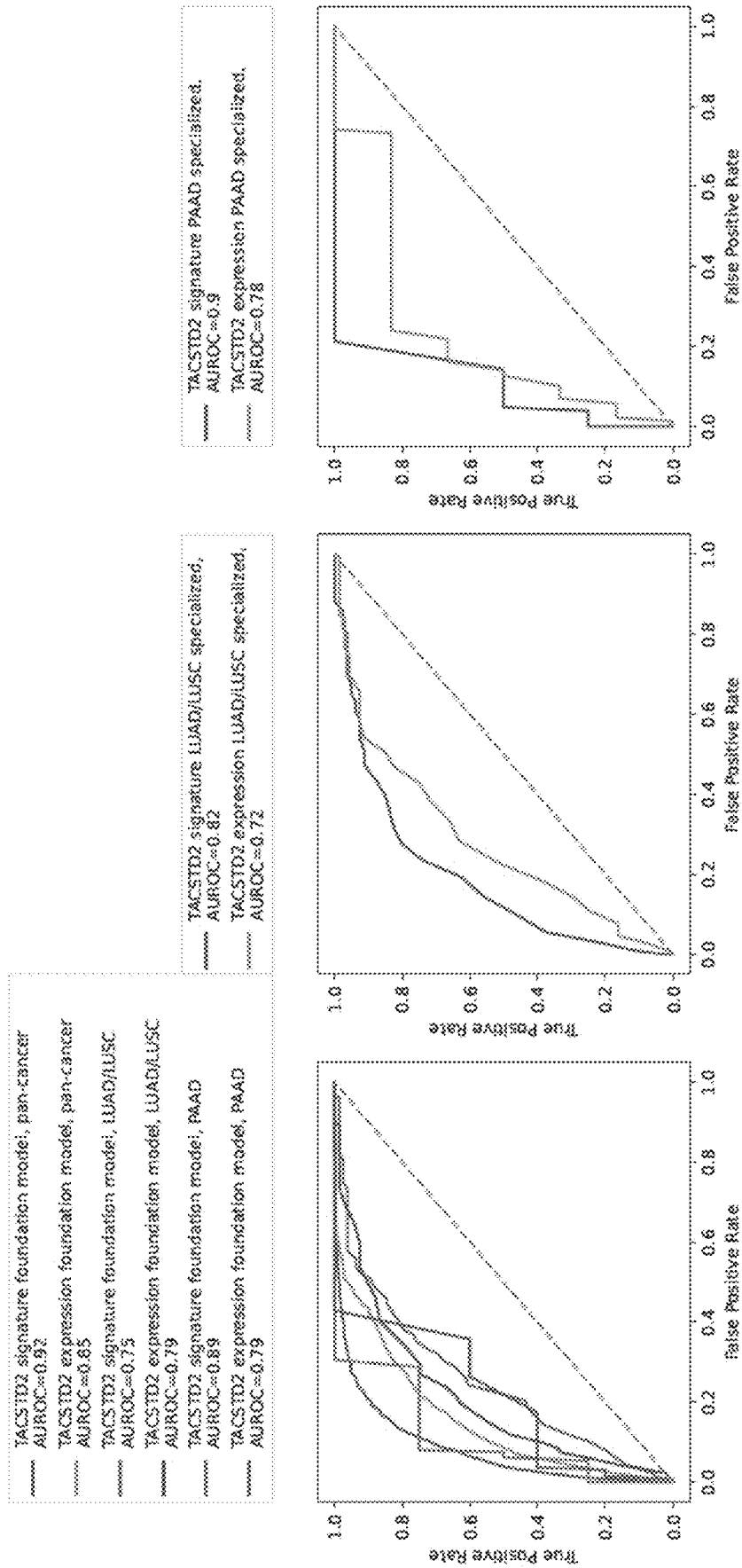
FIG. 31B illustrates performance of models trained to predict overexpression or an elevated amplification signature, performance when the model is further specialized for prediction within NSCLC, and performance of a model trained for pancreatic cancer prediction, in the case of TACSTD2, in accordance with some embodiments.

The potential for TACSTD2 biomarkers was further investigated by developing specialized, cohort-specific over-expression and signature models in NSCLC and pancreatic cancer. Performance of the resulting model is shown in FIG. 31B. FIG. 31B on the left shows performance of models trained to predict overexpression or an elevated amplification signature from the foundation model's embeddings, the center shows the performance when the model is further specialized for prediction within NSCLC, and the right shows performance of a model trained for pancreatic cancer prediction, in the case of TACSTD2. In both cases, specialization improved performance at signature prediction at the cost of some performance in expression prediction. In NSCLC, the AUROC for signature prediction increased from 0.75 to 0.82, and in pancreatic from 0.89 to 0.90. Meanwhile, for over-expression prediction, the AUROC decreased from 0.79 to 0.72 for NSCLC, and 0.79 to 0.78 for pancreatic. In this situation, the pan-cancer model can be retained for predicting over-expression, while deploying the specialized models for amplification signature prediction.

Use Case: Cabozantinib Case Study

A key clinical application of the approach described herein is the ability to use a biomarker to stratify patients into responders and non-responders. Unfortunately, availability of clinical outcomes in the cohorts described herein was limited, especially for targeted therapies, which are often relatively new to clinical practice. To increase the set of examinable hypotheses, the evaluation was expanded beyond biologics to consider any targeted therapies against selected targets for which there were a sufficient number of patients (n>30) to properly power the analysis. This resulted in 38 (indication, target) pairs. Associations between imputed signatures and overall survival (OS) were tested for after adjusting for age at diagnosis, age at disease staging, pre-treatment stage, sex, cancer type, metastatic status, number of unique prior therapies, and time from diagnosis to treatment with the therapy of interest.

Figure 32:
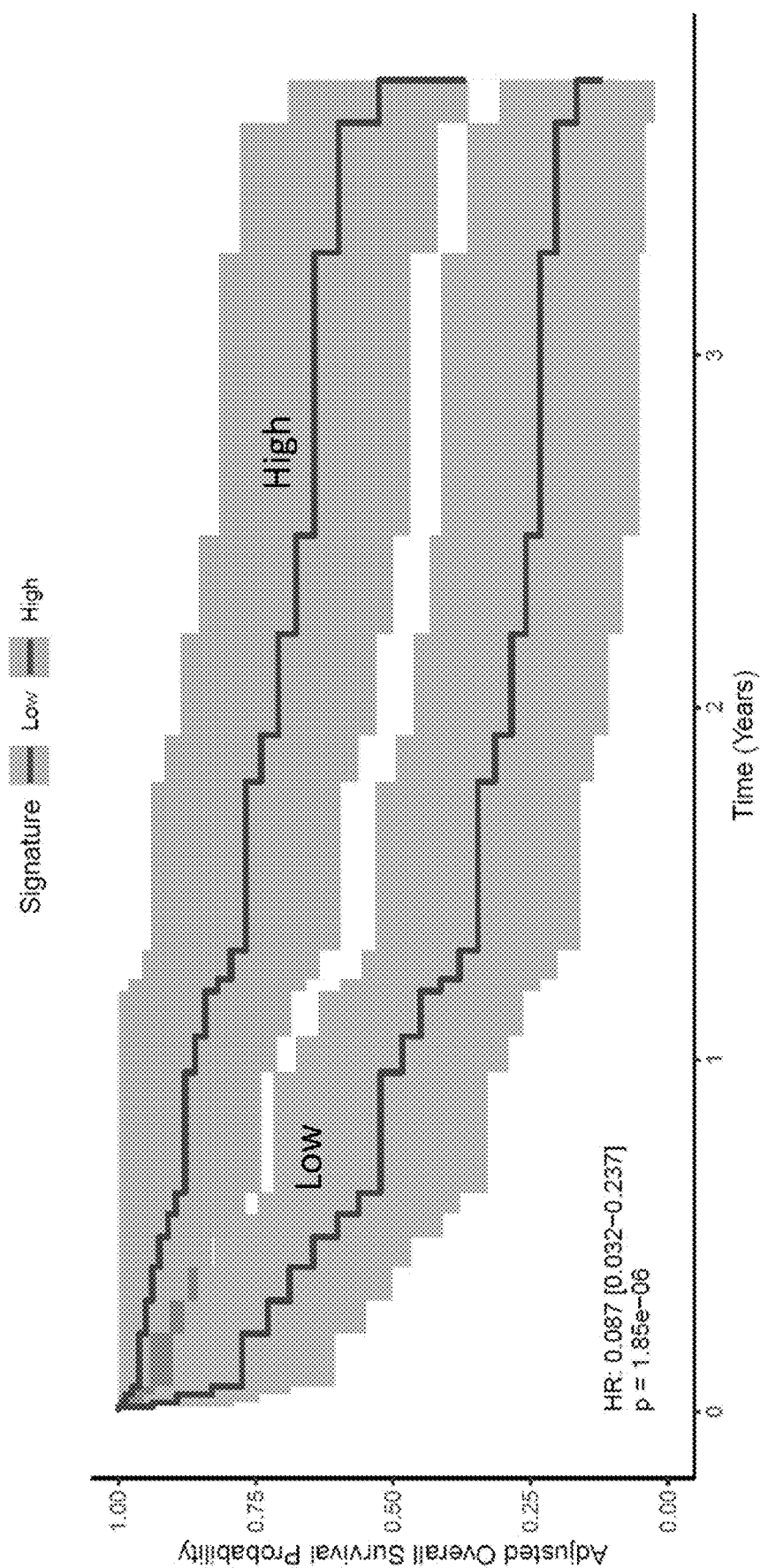
FIG. 32 illustrates covariate-adjusted Kaplan-Meier curves comparing patients with low versus high VEGFR2 signature scores in accordance with some embodiments.

The analysis revealed a significant association between VEGFR2 (KDR) amplification signature and OS among cabozantinib-treated patients (hazard ratio [HR]: 0.087; 95% CI, 0.032 to 0.237; Bonferroni adjusted P=7.0×10-5). The covariate-adjusted Kaplan-Meier curves comparing patients with low versus high VEGFR2 signature scores are presented in FIG. 32. Patients were partitioned into two groups ("high" and "low") on the basis of their VEGFR2 (KDR) amplification signature, but without reference to their survival. The reported hazard ratio (HR) and p-value, comparing patients in the low vs. high VEGFR2 signature groups, were estimated via a Cox model, adjusting for clinical covariates. The KM curves were adjusted for covariates using direct standardization. Importantly, no outcome data (for cabozantinib or any other drug) were used to inform the design of the amplification signature. For comparison, the HR for the MET signature among the same patient group was 1.39 (95% CI, 0.573 to 3.351; P=0.47). An analysis of measured VEGFR2 expression level also suggested an association with improved OS among patients treated with cabozantinib (HR: 0.727), although the evidence was inconclusive (P=0.10), illustrating the increased power of the imputed signatures. Notably, the VEGFR2 signature (measured or imputed) was not correlated with improved OS in 372 cohort A RCC patients more broadly, suggesting that the clinical benefit is specific to cabozantinib.

Cabozantinib is a broad-ranging tyrosine kinase inhibitor (TKI) with activity against MET, RET, AXL, VEGFR2, FLT3, and c-KIT [61], and it has been approved for treatment of renal cell carcinoma (RCC), medullary thyroid cancer, and hepatocellular carcinoma. Of the 31 patients treated with cabozantinib, a majority (22/31) were diagnosed with renal cancer. VEGF-A is a known prognostic marker in metastatic RCC, and high levels of VEGF-A are associated with poorer OS and progression-free survival among patients treated with sunitinib, another TKI. A previous study demonstrated that markers of angiogenesis microvascular density and mast cell density were associated with improved outcomes in metastatic clear cell RCC; however, these did not seem to be predictive of efficacy for cabozantinib compared to everolimus (an mTOR inhibitor). Despite this finding, given the known relationship of RCC biology with VEGF signaling and the proposed MOA of cabozantinib, the highly significant association between VEGFR2 signature and OS among cabozantinib-treated patients could be of interest for future biomarker development, as well as providing suggestive evidence for VEGF as a mechanism by which cabozantinib derives efficacy in RCC.

Use Case: Interrogating Spatial Heterogeneity

An important attribute of the models descried herein is that they may generate biomarker predictions at the resolution of individual tiles. This provides the ability to generate spatial gene expression predictions across WSIs. Specifically, the model may make predictions for each biomarker and for each tile, allowing for creation of a synthetic annotation on top of the WSI, in which the biomarker predictions are overlaid on each tile within the slide. This capability can be useful in a number of ways. First, it "opens the black box" by providing a human expert the ability to interrogate the process that gave rise to the results. Second, it creates a view on the spatial distribution of multiple biomarkers, providing considerable insight into tumor architecture and intra-tumor heterogenity. Indeed, since these imputations are derived directly from the H&E, this capability supports a form of "label-free" staining across a very large set of molecular readouts.

Figure 33A:
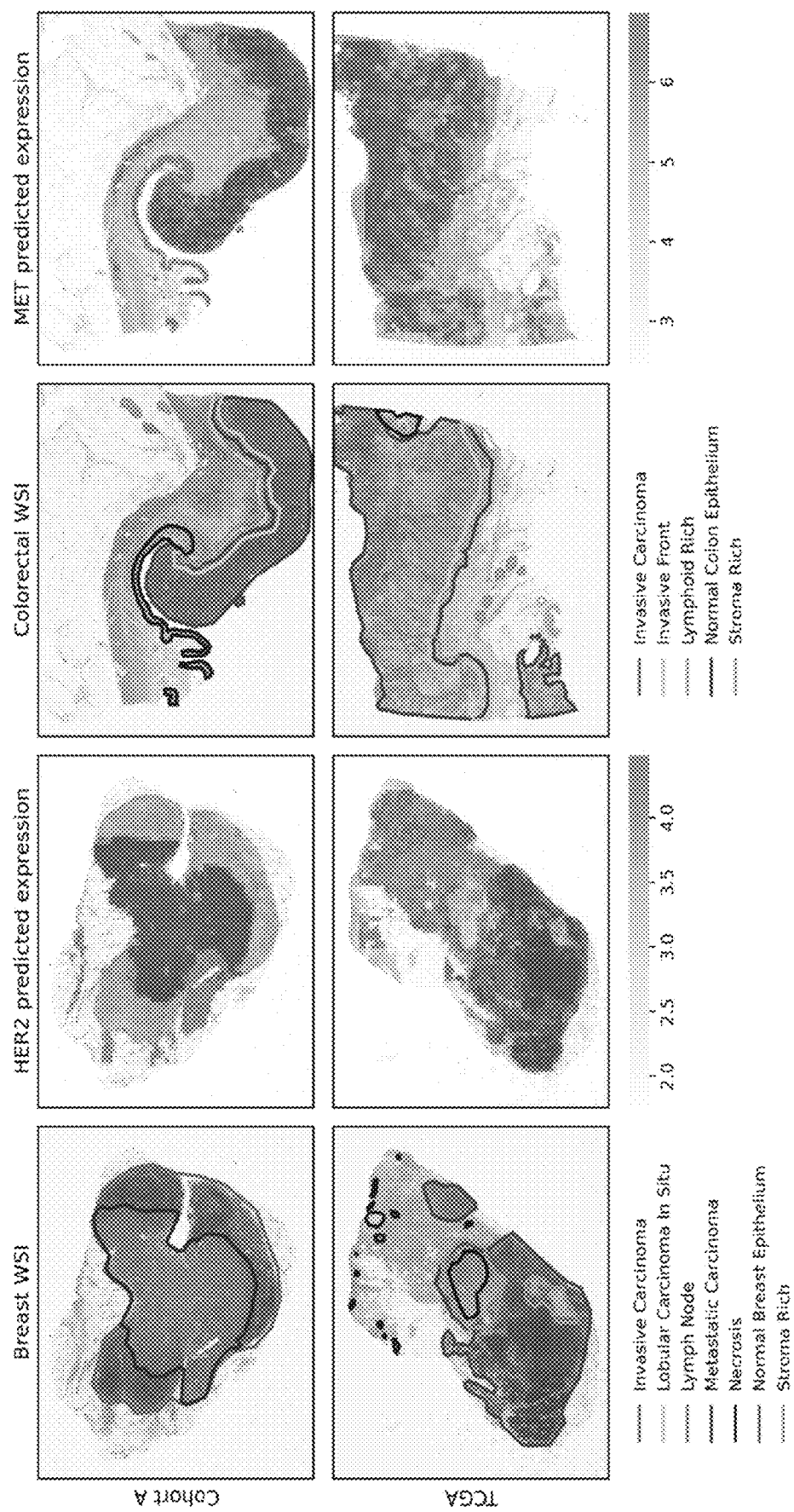
FIG. 33A illustrates examples of synthetic overlays, localizing HER2 expression in breast cancer and MET expression in colorectal cancer, in accordance with some embodiments.
Figure 33B:
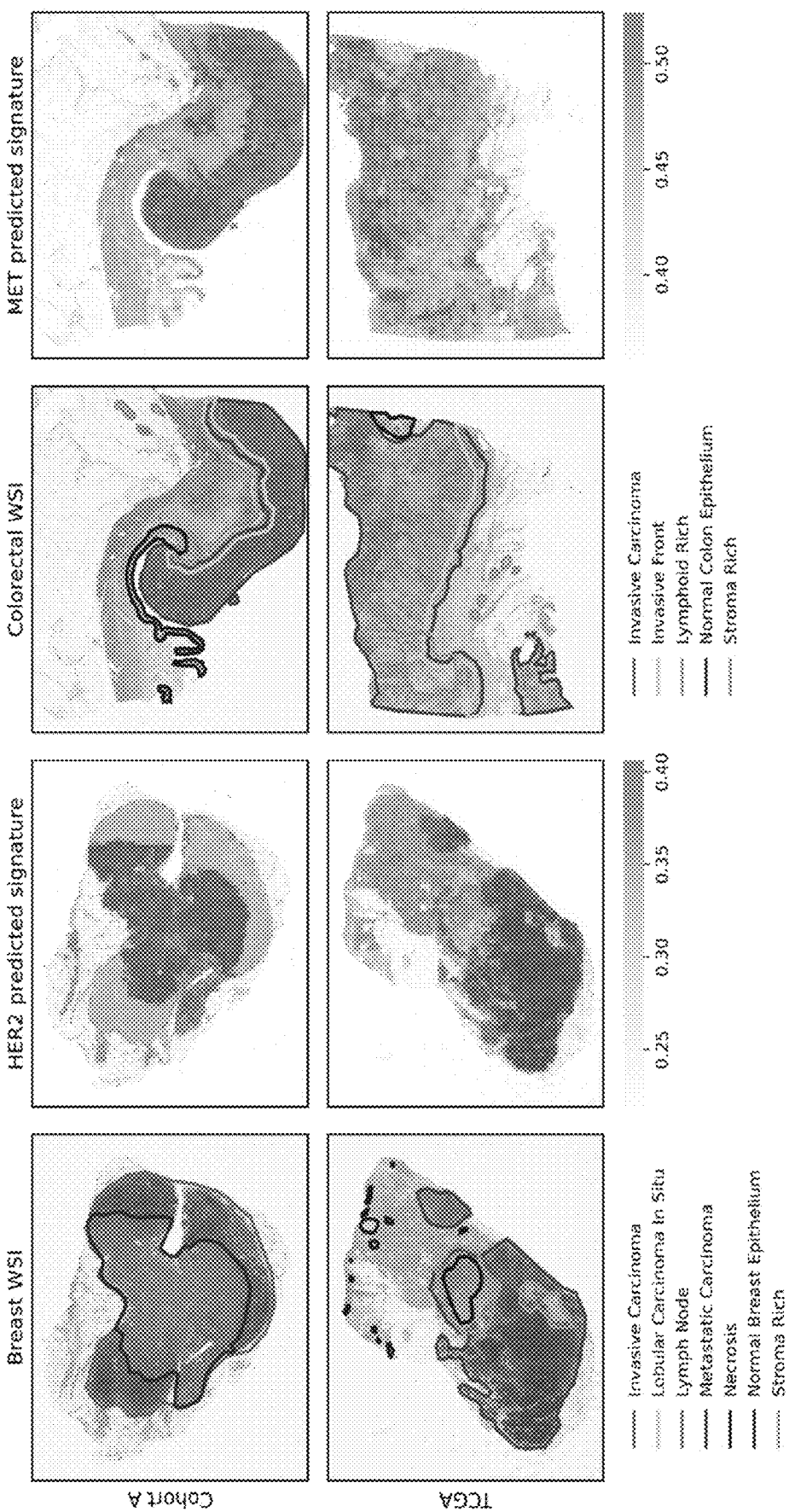
FIG. 33B illustrates examples of synthetic overlays for amplification signature prediction in accordance with some embodiments.
Figure 34:
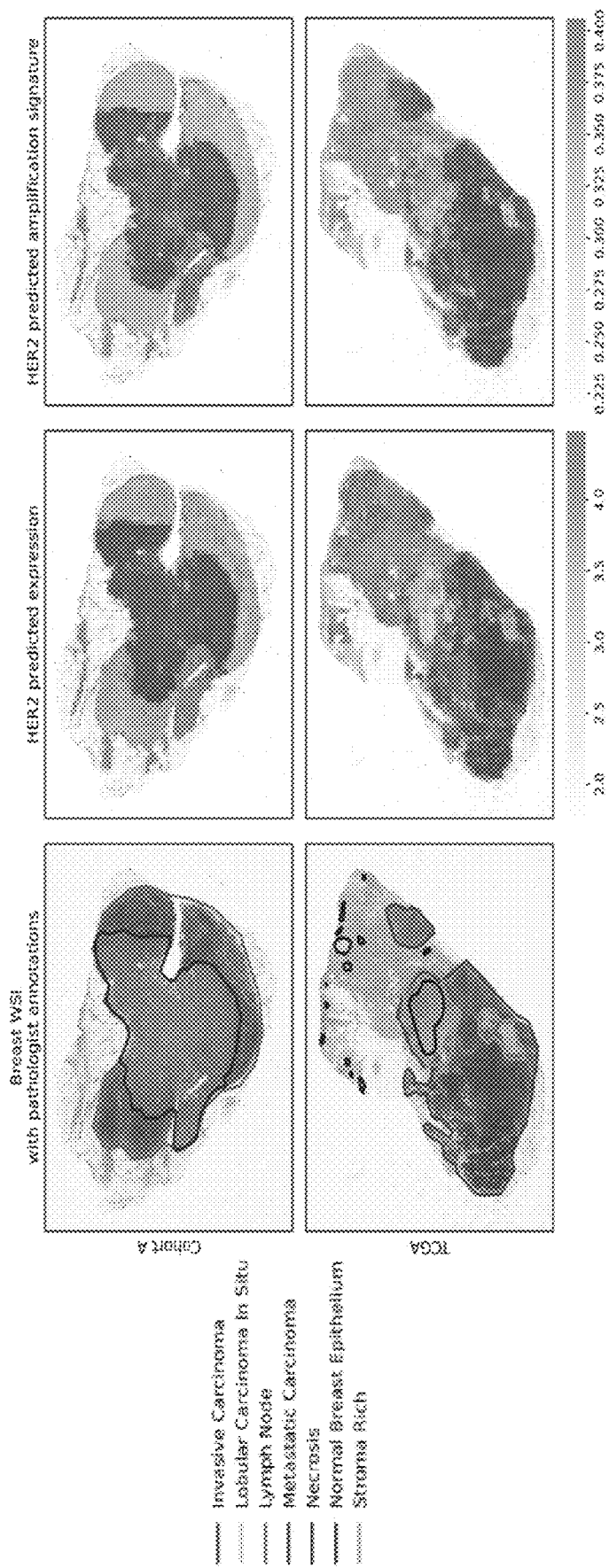
FIG. 34 depicts a comparison of expression and signature predictions with expert pathologist annotations in breast cancer in accordance with some embodiments.
Figure 35:
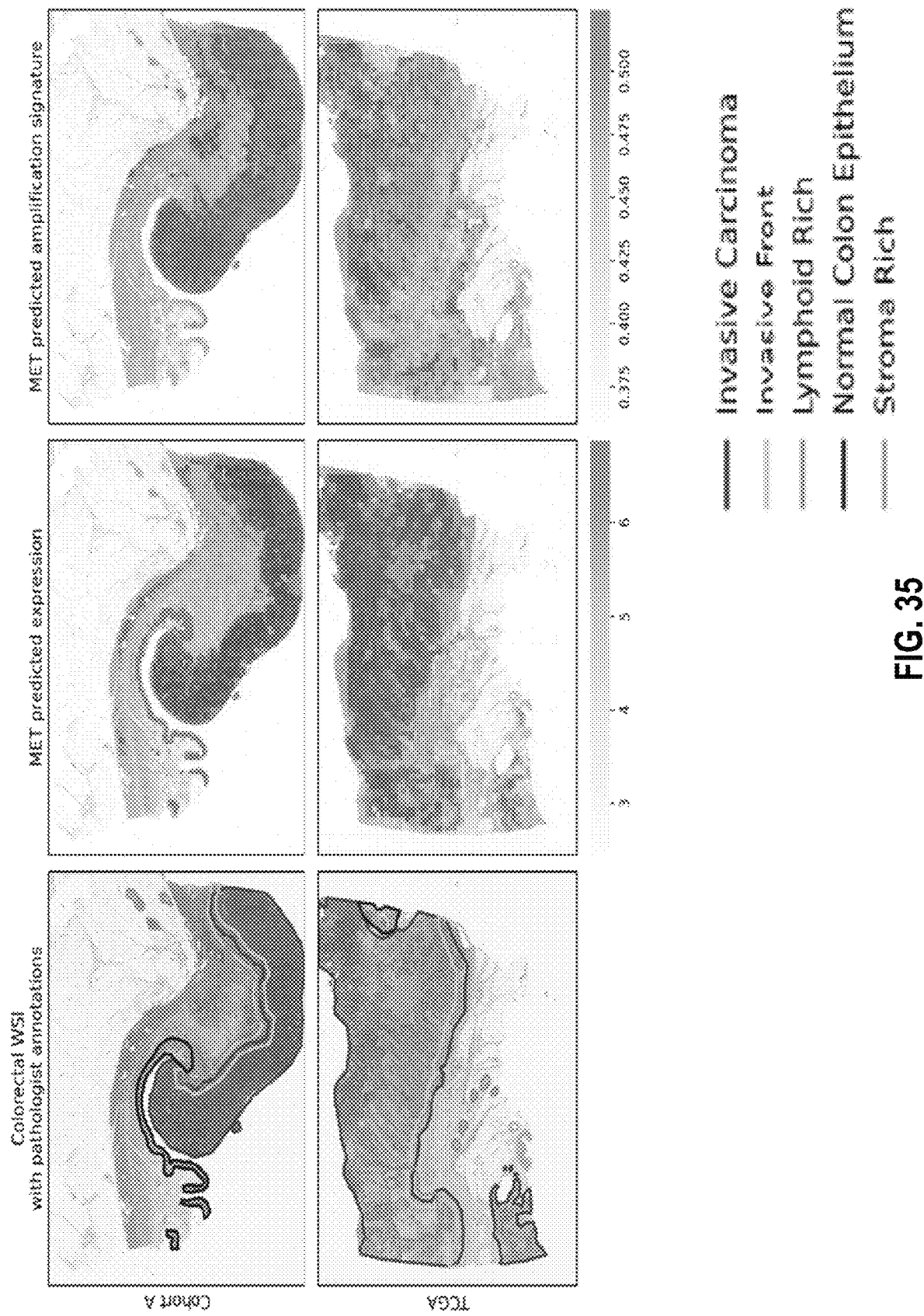
FIG. 35 depicts a comparison of expression and signature predictions with expert pathologist annotations in colorectal cancer in accordance with some embodiments.

FIG. 33A shows some examples of these synthetic overlays, localizing HER2 expression in breast cancer and MET expression in colorectal cancer. FIG. 33B shows similar overlays for amplification signature prediction. To provide a baseline for these predictions, an expert pathologist was asked to annotate a random sample of WSIs from patients with and without amplifications while blinded to all model predictions. The fact that increased expression coincides with regions annotated as cancerous aligns with clinical knowledge and suggests that the model has learned to distinguish between tumor and normal tissue. Importantly, the model has learned this distinction while trained only on bulk, not spatially resolved, expression data. FIGS. 34 and 35 provide an alternate view of these results in which the target expression and amplification signature predictions are juxtaposed. FIG. 34 depicts a comparison of expression and signature predictions with expert pathologist annotations in breast cancer. The pathologist was again blinded to the predictions and although the expression/signature models provide tile-level predictions, they were trained only on bulk, not spatially resolved, information. FIG. 35 depicts a similar comparison of expression and signature predictions with expert pathologist annotations in colorectal cancer.

Figure 36:
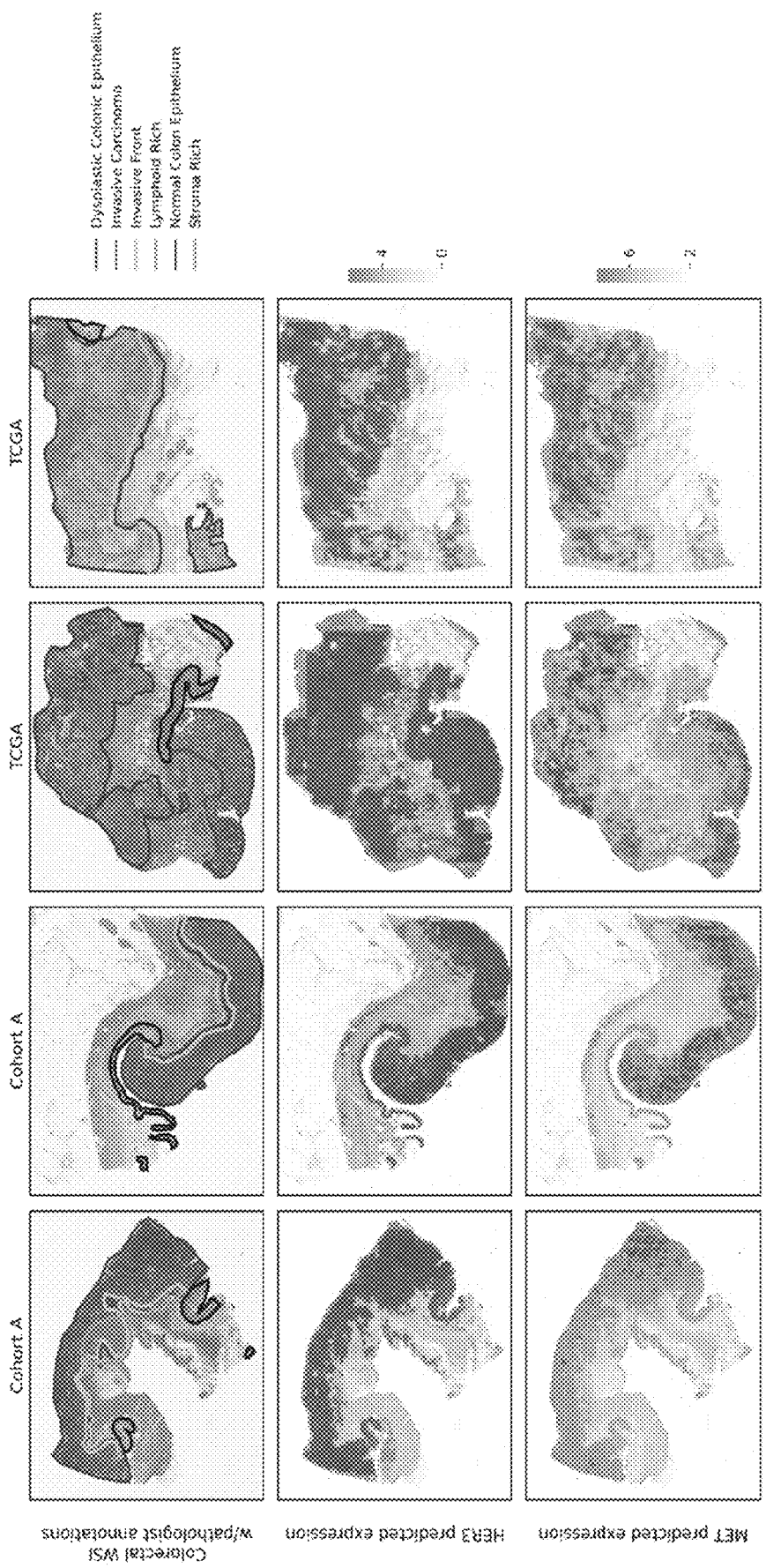
FIG. 36 provide examples of co-expression prediction for HER3 plus MET alongside blinded pathologist annotations in accordance with some embodiments.
Figure 37:
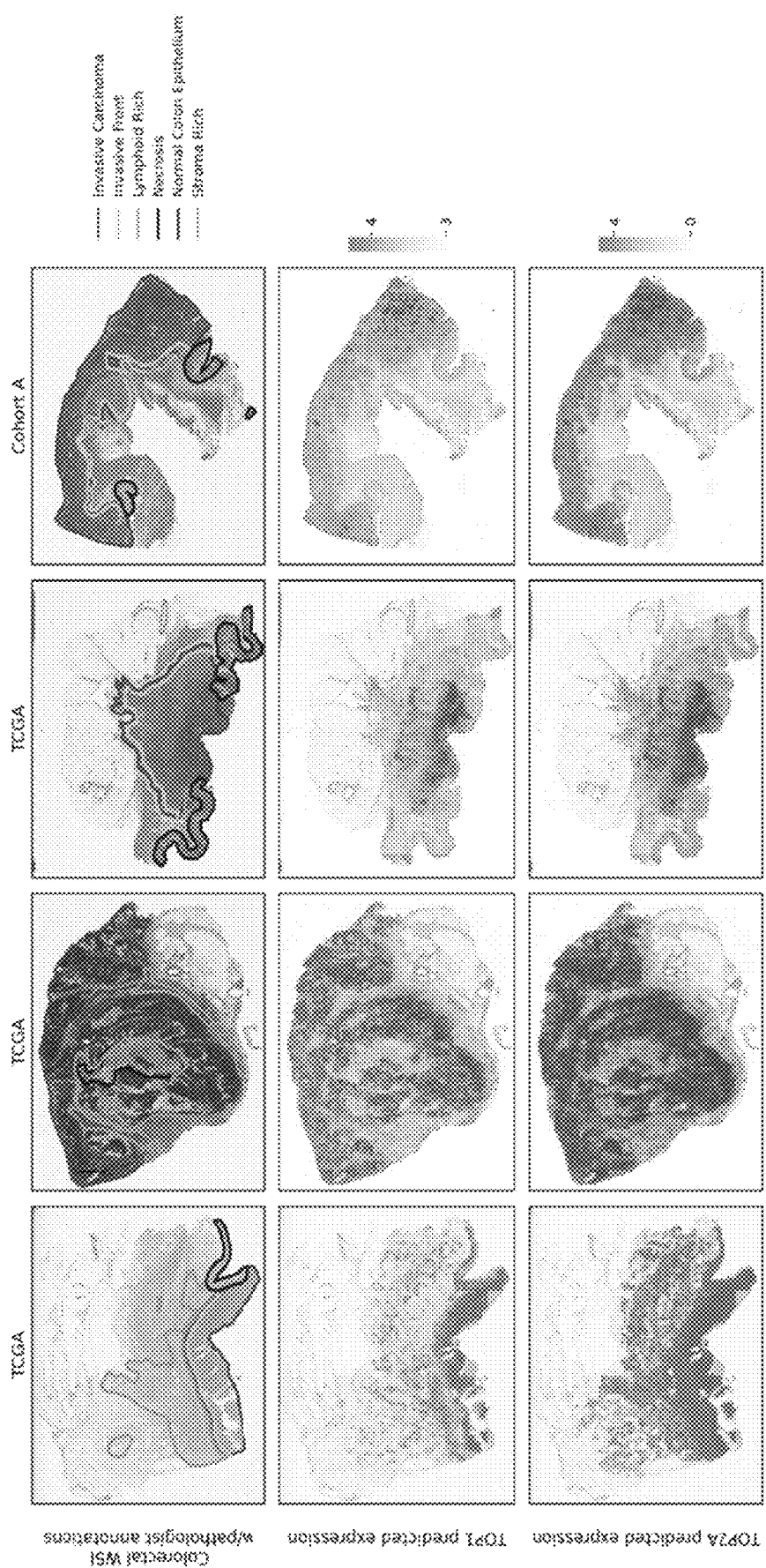
FIG. 37 illustrates examples of co-expression prediction for TOP1 plus TOP2A alongside blinded pathologist annotations in accordance with some embodiments.

Since the molecular labels are all synthetically generated, it is possible to derive multiple labels for the same image. FIG. 36 and FIG. 37 provide examples of co-expression prediction for HER3 plus MET and TOP1 plus TOP2A, respectively, alongside blinded pathologist annotations. The differences in the spatial expression predictions of these target pairs underscore that the model is learning more nuanced expression information than whether or not a tile falls within a cancerous region of the slide.

Machine Learning Modeling Insights

Machine Learning Modeling Insights: Transportability Across Cohorts

An important aspect of machine learning models is the extent to which they generalize outside of the distribution on which they were trained. This generalization is important in assessing the robustness of the approach, i.e., in not overfitting to the specifics of a single data set. It is also useful from a clinical deployment perspective, increasing confidence that the model will behave when applied in a new clinical setting.

Table 2 presents AUROCs from an experiment where multi-task binary outcome models were trained to predict elevated expression and amplification signatures using data from TCGA only, then evaluated on patients from cohort A only. Results are shown pan-cancer and within breast and colorectal cancer. Stratified results are not presented as the set of cancers available in cohort A only differs from the set available in TCGA+cohort A, and the results would not be comparable with those presented elsewhere. Although significant predictive power is retained, some decrease in performance is always expected when applying a model in a new dataset. Surprisingly, for breast and colorectal cancer, elevated signature prediction improved across datasets, perhaps suggesting these cohorts are more heterogeneous in TCGA than in cohort A.

TABLE 2

Transportability of binary expression and amplification predictions across data sets. Reported are the mean AUROCs across targets. The within dataset results were obtained via cross-validation, training and testing with data from both TCGA and cohort A. The across dataset results were obtained by training on TCGA only then evaluating on cohort A only.

| Biomarker | Cohort | Across Dataset | Within Dataset | Relative Change (%) |
| --- | --- | --- | --- | --- |
| RNA | Pan-cancer | 0.742 | 0.853 | −13.0 |
| RNA | Breast | 0.676 | 0.731 | −7.5 |
| RNA | Colorectal | 0.689 | 0.720 | −4.4 |
| SIG | Pan-cancer | 0.797 | 0.897 | −11.2 |
| SIG | Breast | 0.777 | 0.773 | 0.5 |
| SIG | Colorectal | 0.786 | 0.724 | 8.5 |

Machine Learning Modeling Insights: Machine Learning Architectures

Three different model architectures were evaluated in the Exemplary Studies described herein, as summarized in Table 3. Panels (a) and (b) of Table 3 explore different ways in which the information across different tiles might be combined. Panel (a) considers whether the model should receive as input separate embeddings for each tile in a patient's WSI, or the average embedding across tiles. Maintaining separate embeddings for each tile performed better, which essentially provides the model with more, albeit correlated, training examples. Panel (b) considers whether to generate predictions for each tile separately, or to incorporate an attention mechanism, allowing the model to make patient-level predictions while attending to spatially adjacent tiles. While spatial attention did not benefit the models overall, the prediction of certain targets did benefit; for example, in TLR9 the Spearman correlation between observed and predicted expression increased from 20% to 48%. Panel (c) considers the value of training across multiple biomarker tasks. Specifically, the following approaches were compared: (1) training separate models to predict each target, (2) training a single model to simultaneously predict all targets, or (3) training a single model to predict expression transcriptome-wide then subset the targets of interest. The last strategy performed best, and both multi-task strategies substantially outperformed the individual (single-task) strategy for the model architecture.

TABLE 3

| (a) Tile Averaging | |
| --- | --- |
| Average tiles | Spearman |
| No | 0.628 |
| Yes | 0.584 |
| (b) Attention | |
| Tile attention? | Spearman |
| No | 0.628 |
| Yes | 0.404 |
| (c) Multi-tasking | |
| Targets | Spearman |
| Transcriptome | 0.628 |
| All targets | 0.625 |
| Per target | 0.004 |

Additional Data from Exemplary Studies

Figure 38A:
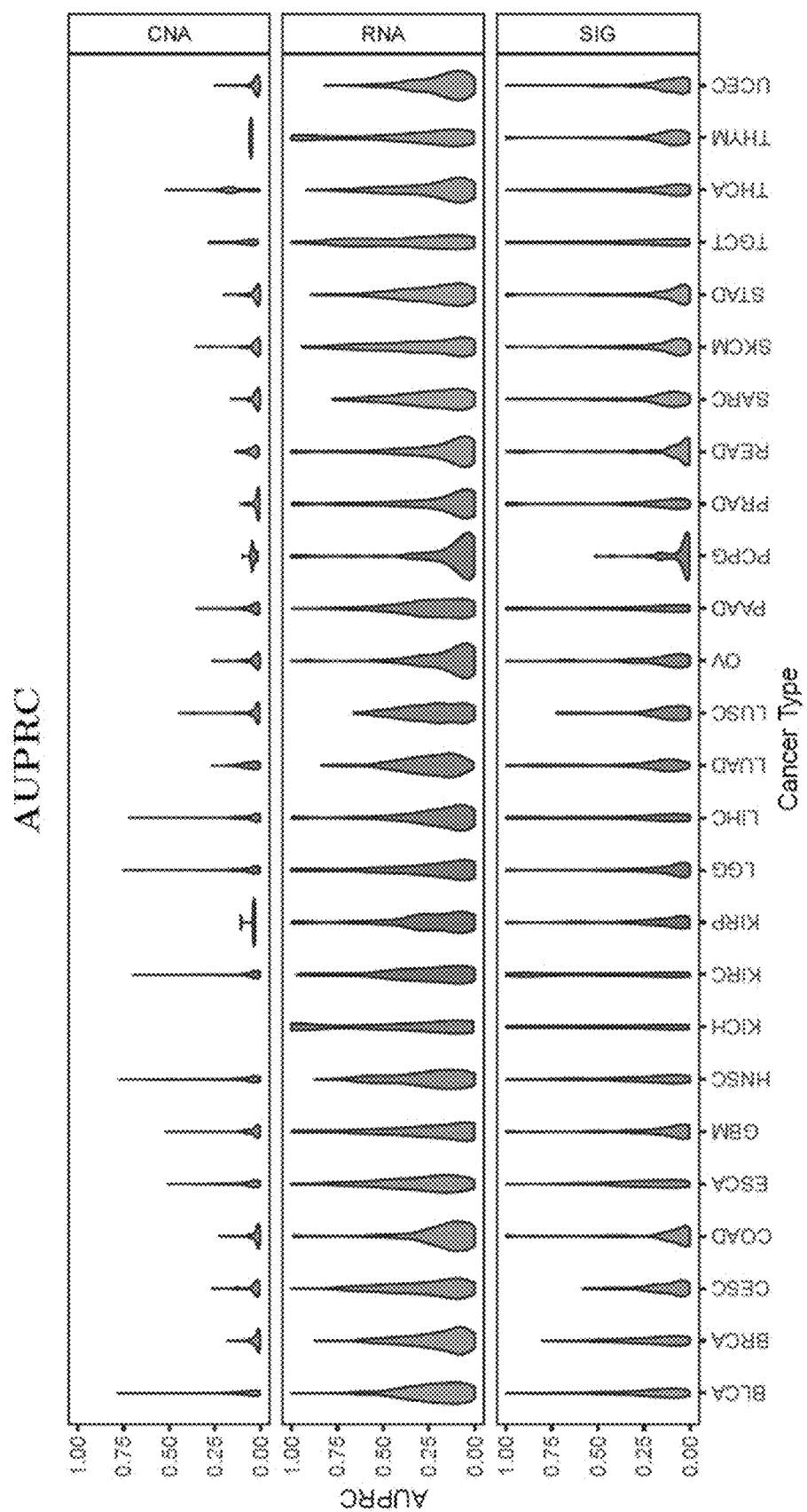
FIGS. 38A and 38B depict cross-modality comparison of binary digital biomarker prediction quality, stratified by cancer-type in accordance with some embodiments.
Figure 38B:
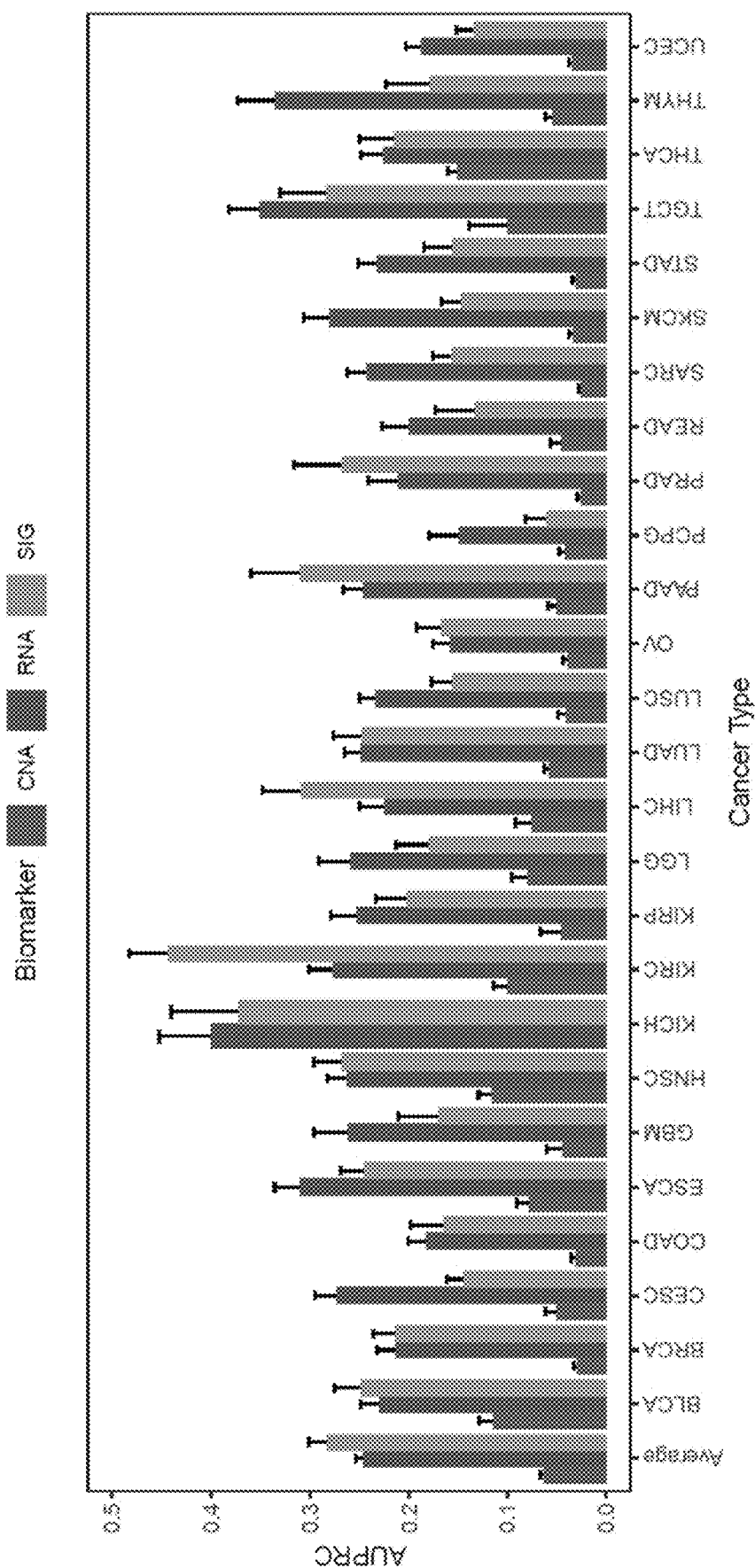

FIGS. 38A and 38B depict cross-modality comparison of binary digital biomarker prediction quality, stratified by cancer-type. Performance was evaluated at the patient level in a held-out evaluation set and averaged across 8 cross-validation folds. Metrics were calculated separately in each cancer type with ≥100 patients. The distributions are shown across up to 352 target genes. For CNA, the task was to predict whether the patient harbored an amplification. For target expression (RNA) and the amplification signature (SIG), the task was to predict whether the patient's expression/signature level exceeded the 95th percentile.

Figure 39A:
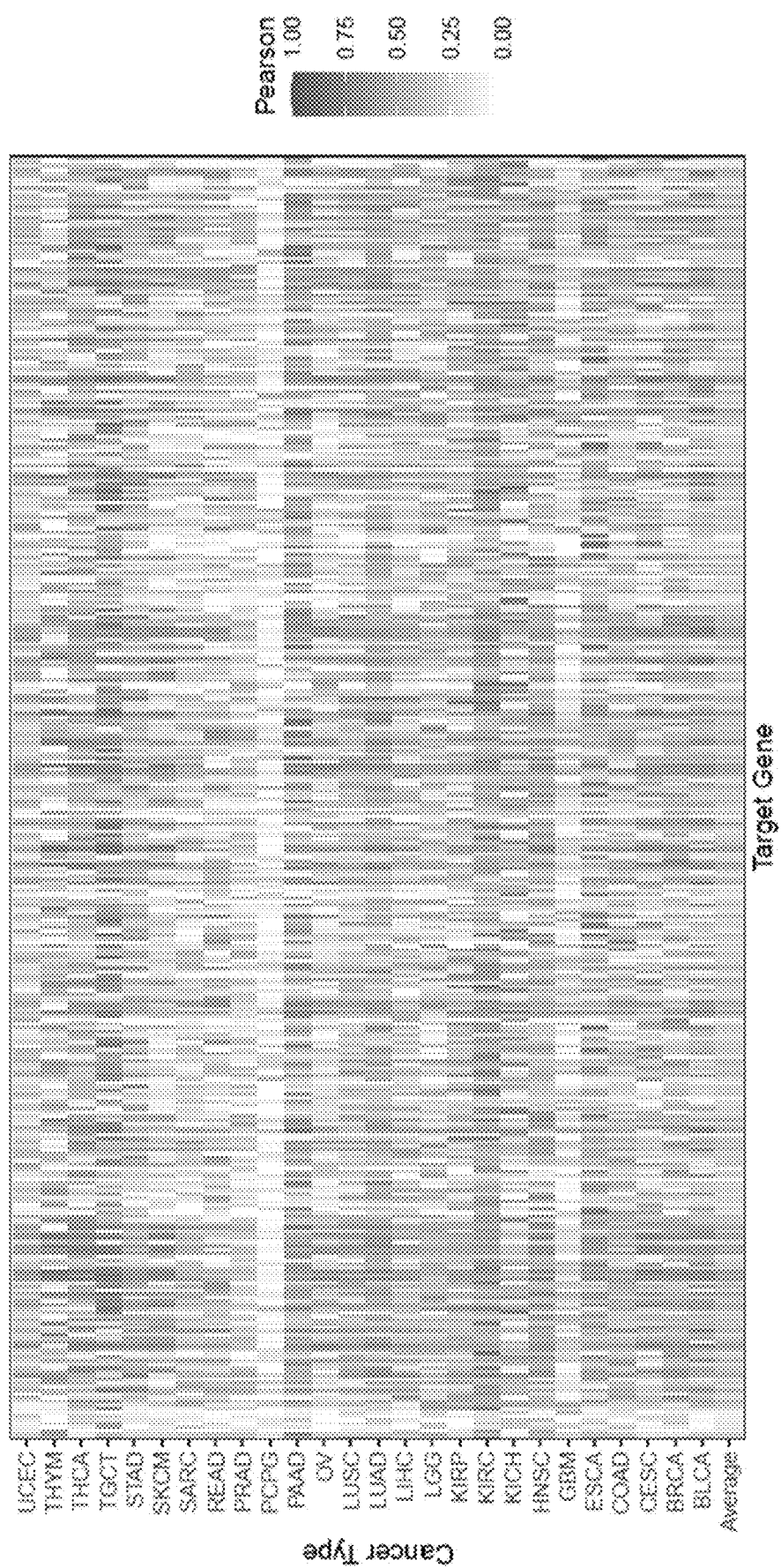
FIGS. 39A and 39B illustrate prediction of target expression level from digital histopathology, stratified by cancer type in accordance with some embodiments.
Figure 39B:
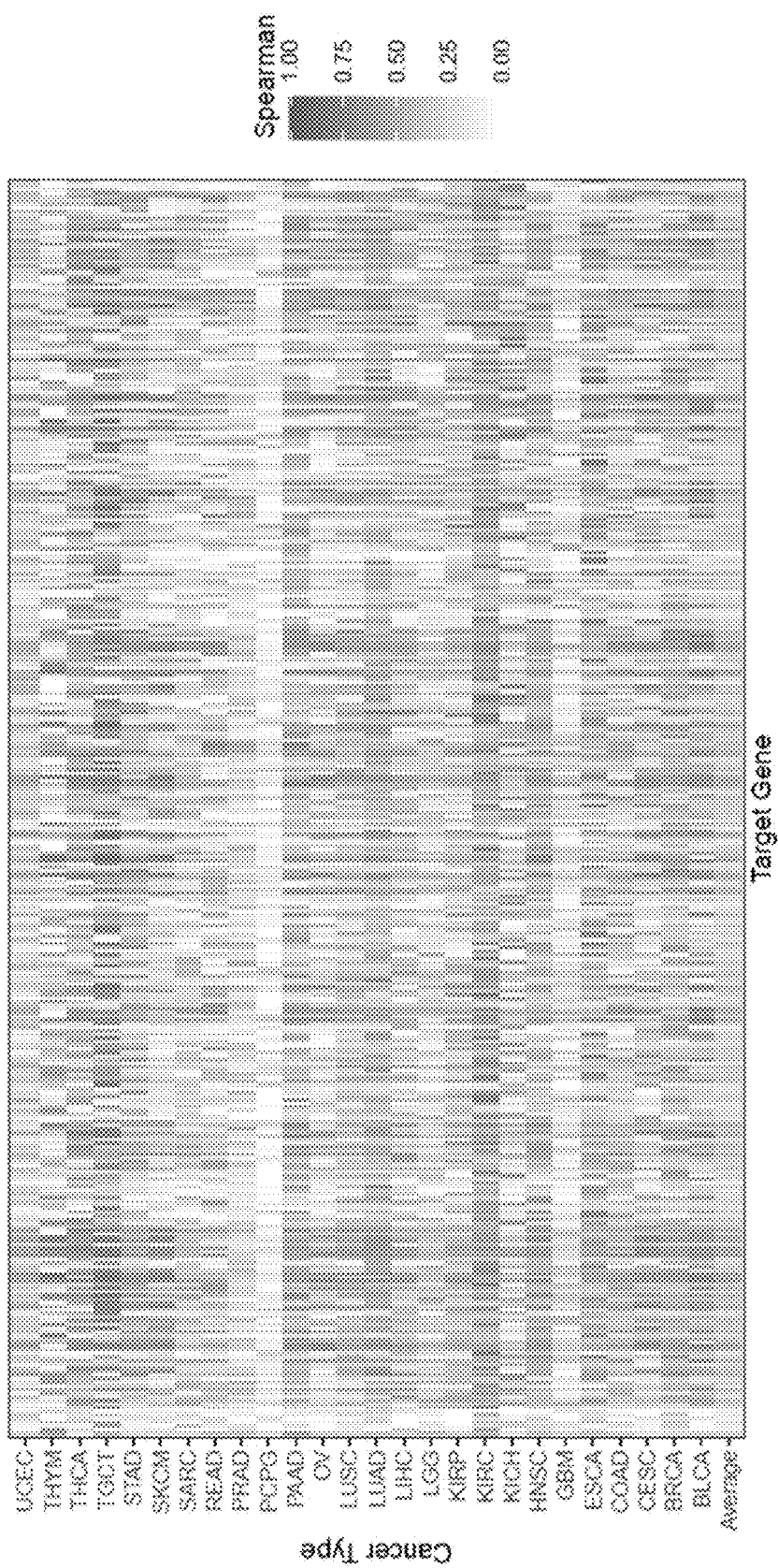

FIGS. 39A and 39B illustrate prediction of target expression level from digital histopathology, stratified by cancer type. Performance was evaluated at the patient level in a held-out evaluation set and averaged across 8 cross-validation folds.

Figure 40A:
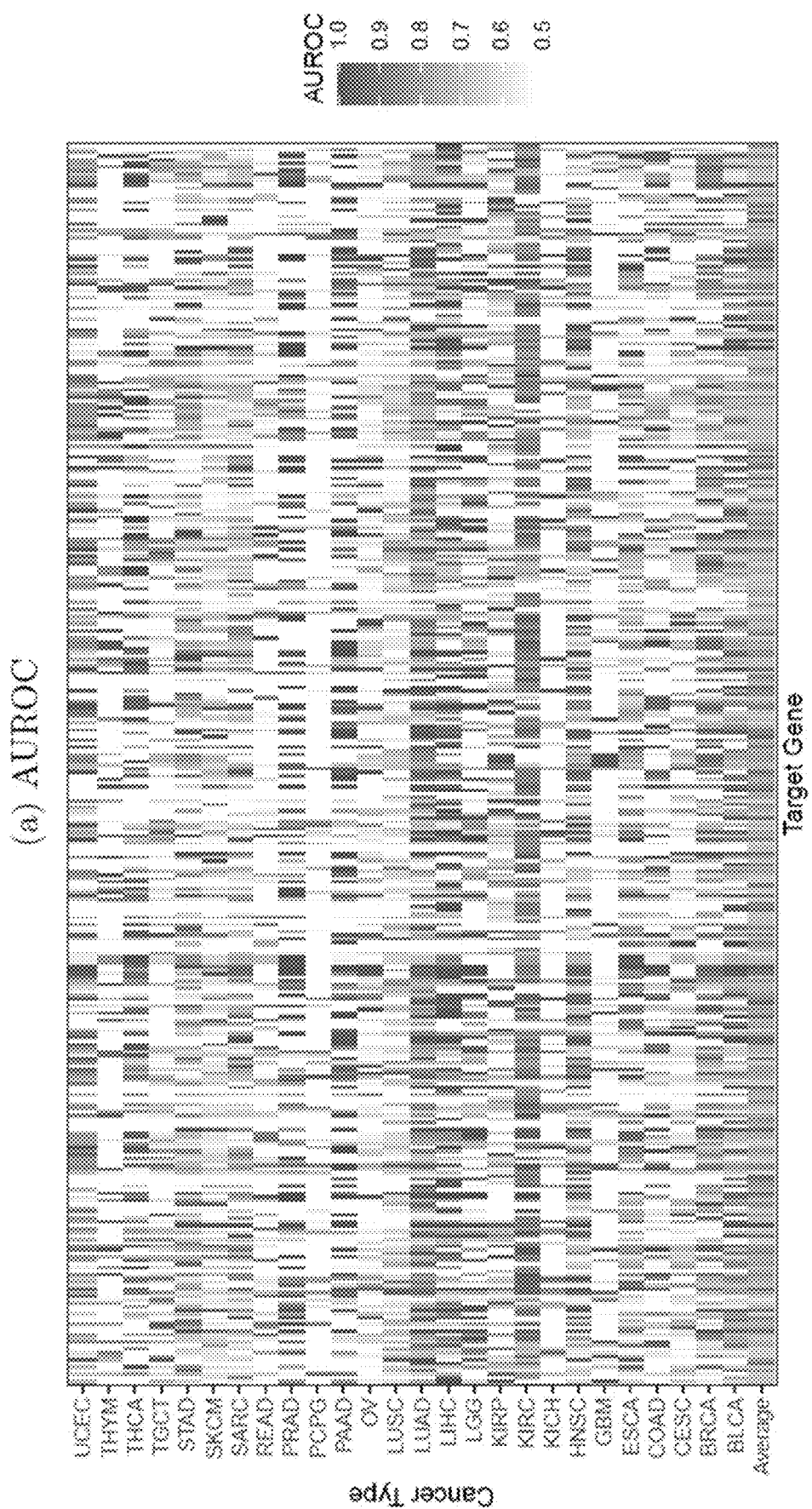
FIGS. 40A and 40B illustrate prediction of elevated amplification signature from digital histopathology, stratified by cancer type in accordance with some embodiments.
Figure 40B:
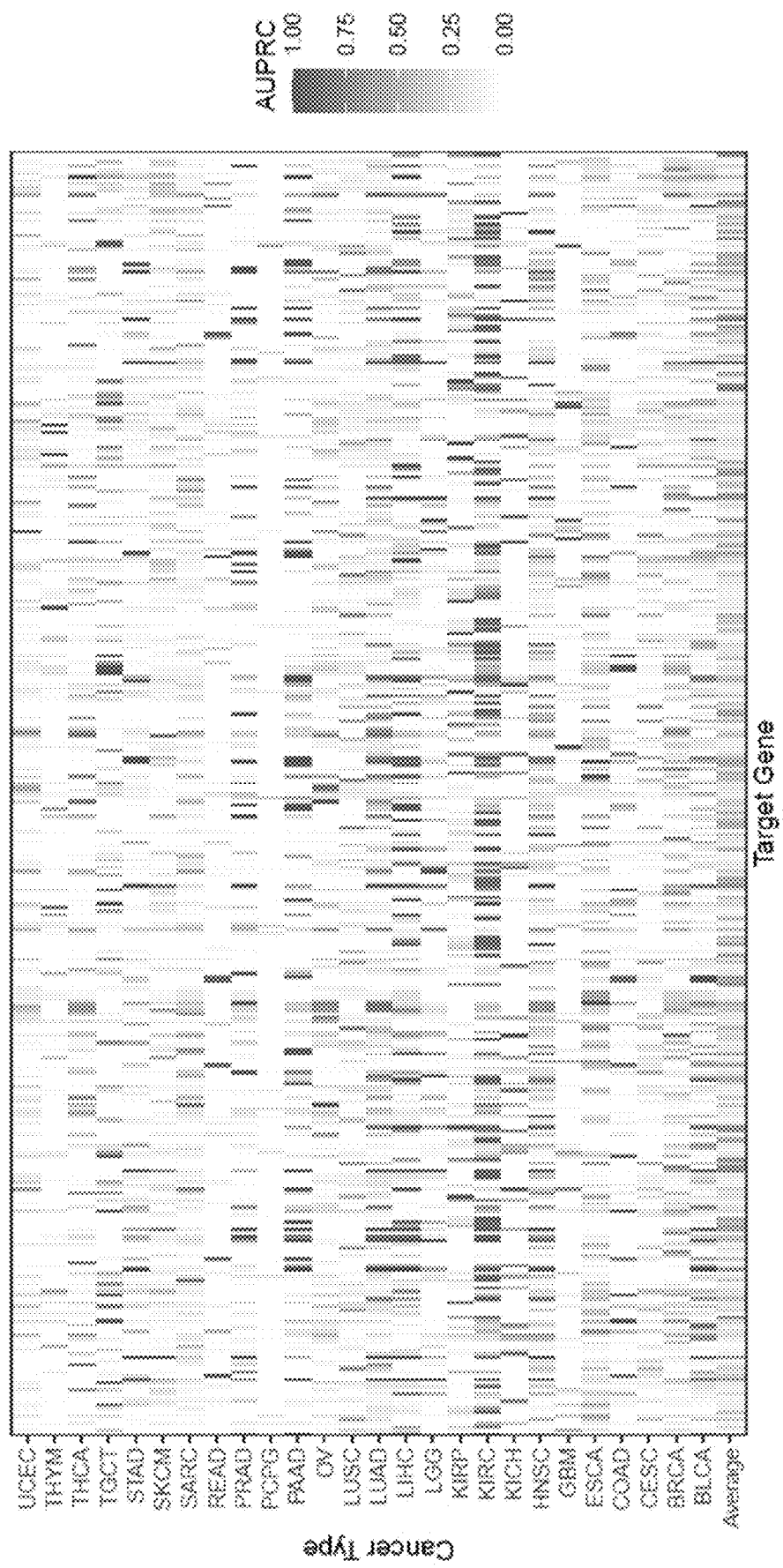

FIGS. 40A and 40B illustrate prediction of elevated amplification signature from digital histopathology, stratified by cancer type. A patient was defined to have an elevated amplification signature if their score exceeded the 95th percentile for a given target. Performance is evaluated at the patient level in a held-out evaluation set and averaged across 8 cross-validation folds.

Figure 41:
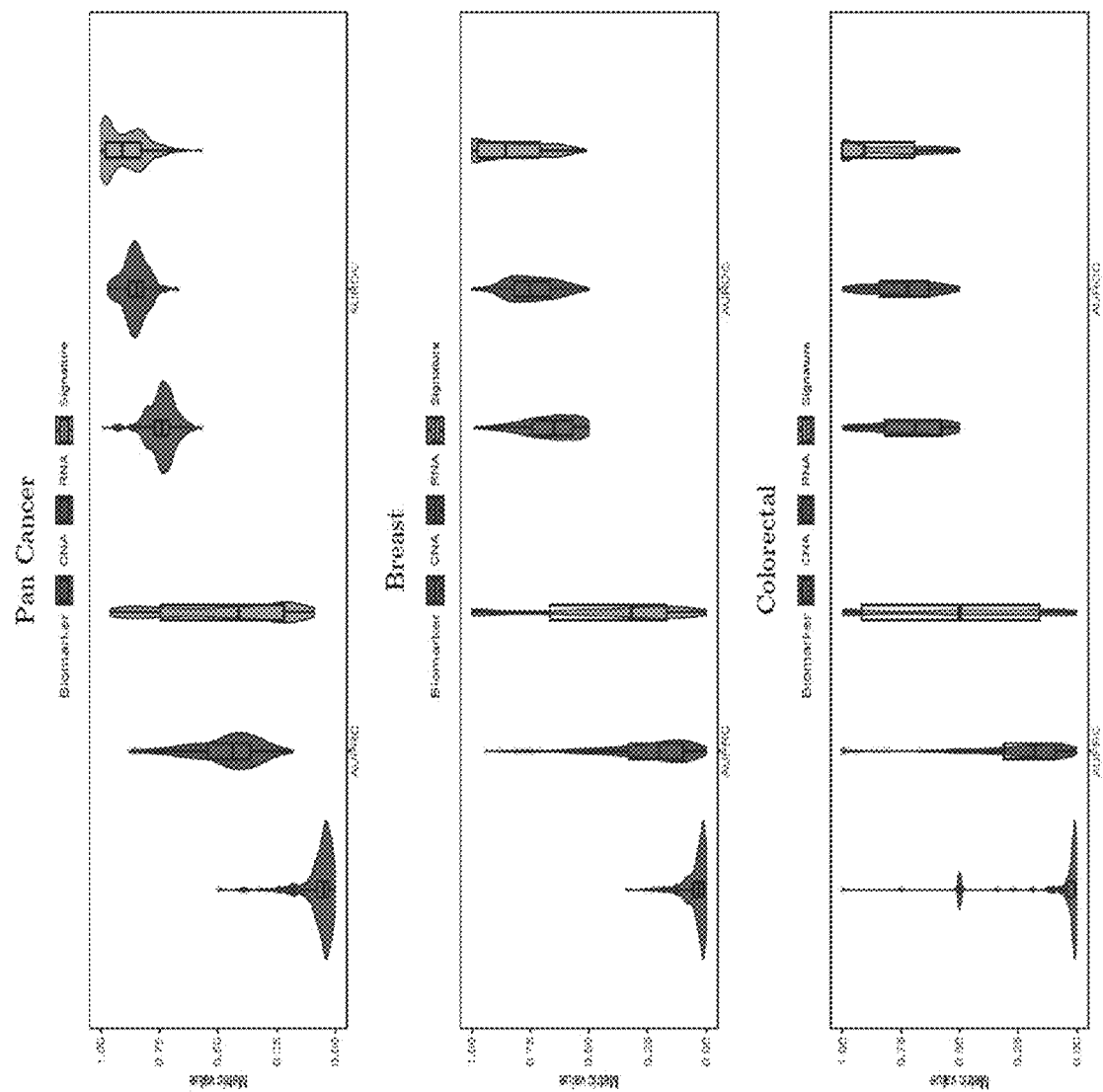
FIG. 41 illustrates model performance on the binary classification task, across biomarkers, stratified by cancer type in accordance with some embodiments.

FIG. 41 illustrates model performance on the binary classification task, across biomarkers, stratified by cancer type. The performance metrics are the areas under the precision-recall (AUPRC) and the receiver operating characteristic (AUROC). Performance is evaluated at the patient level in a held-out evaluation set. For copy number amplification (CNA), the task was to predict whether the patient harbored an amplification. For target expression (RNA) and the amplification signature, the task was to predict whether the patient's expression/signature level exceeded the 95th percentile. Distributions are shown across the 352 target genes.

Figure 42:
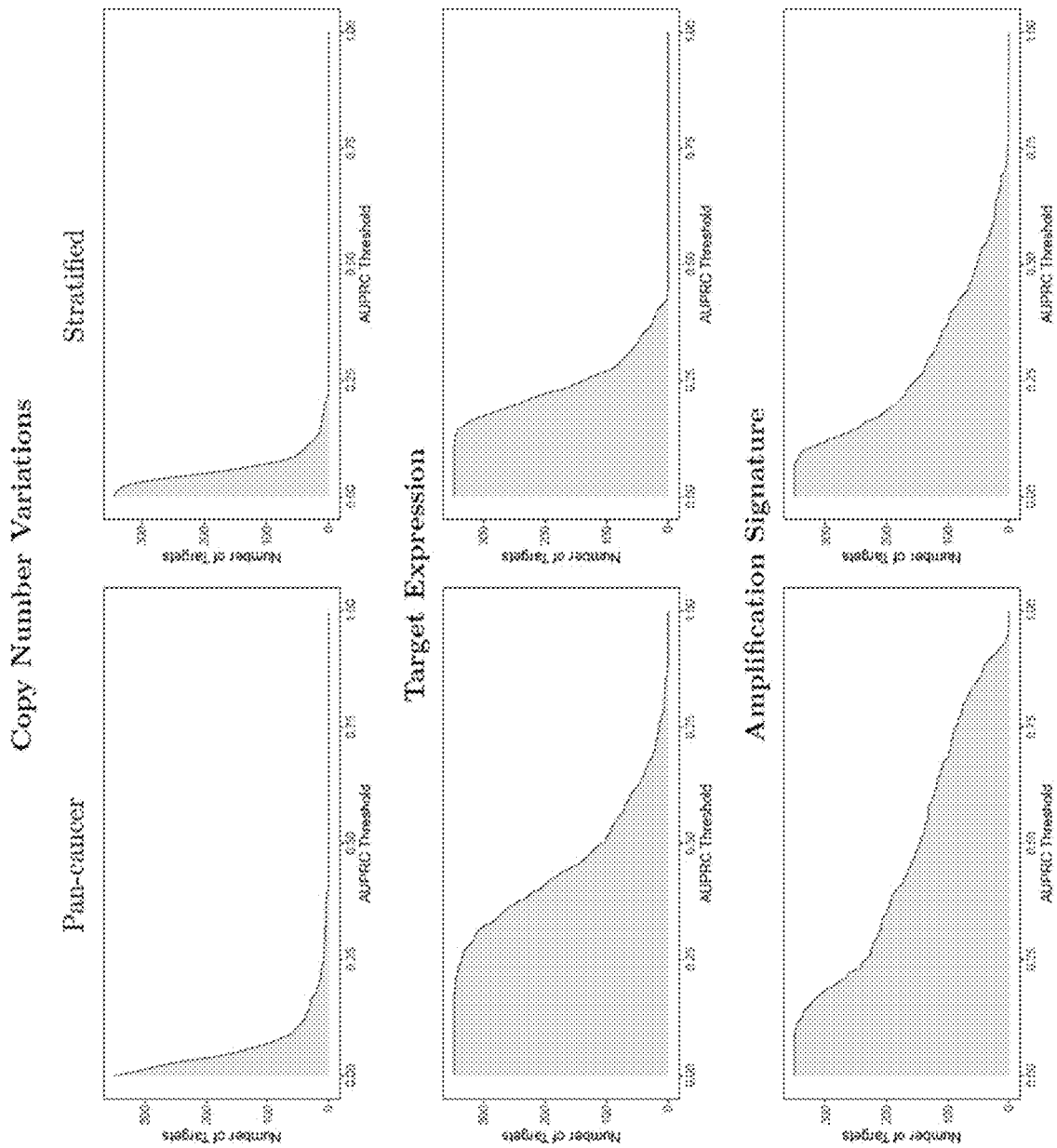
FIG. 42 illustrates a count of targets with AUPRC exceeding a given threshold for the pan-cancer and stratified binary classification task in accordance with some embodiments.

FIG. 42 illustrates a count of targets with AUPRC exceeding a given threshold for the pan-cancer and stratified binary classification task. Performance was evaluated at the patient level in a held-out evaluation set and averaged across 8 cross-validation folds. For the pan-cancer evaluation, the AUPRC is calculated across all patients. For the stratified evaluation, the AUPRC is calculated separately within each cancer type, then averaged across cancer types. For copy number amplification, the task was to predict whether the patient harbored an amplification. For target expression and the amplification signature, the task was to predict whether the patient's expression/signature level exceeded the 95$^{th}$ percentile.

FIG. 43 illustrates a count of genes with AUROC exceeding a given threshold. Performance was evaluated at the patient level in a held-out evaluation set and averaged across 8 cross validation folds. For the pan-cancer evaluation, the AUROC is calculated across all patients. For the stratified evaluation, the AUROC is calculated separately within each cancer type, then averaged across cancer types.

Figure 44A:
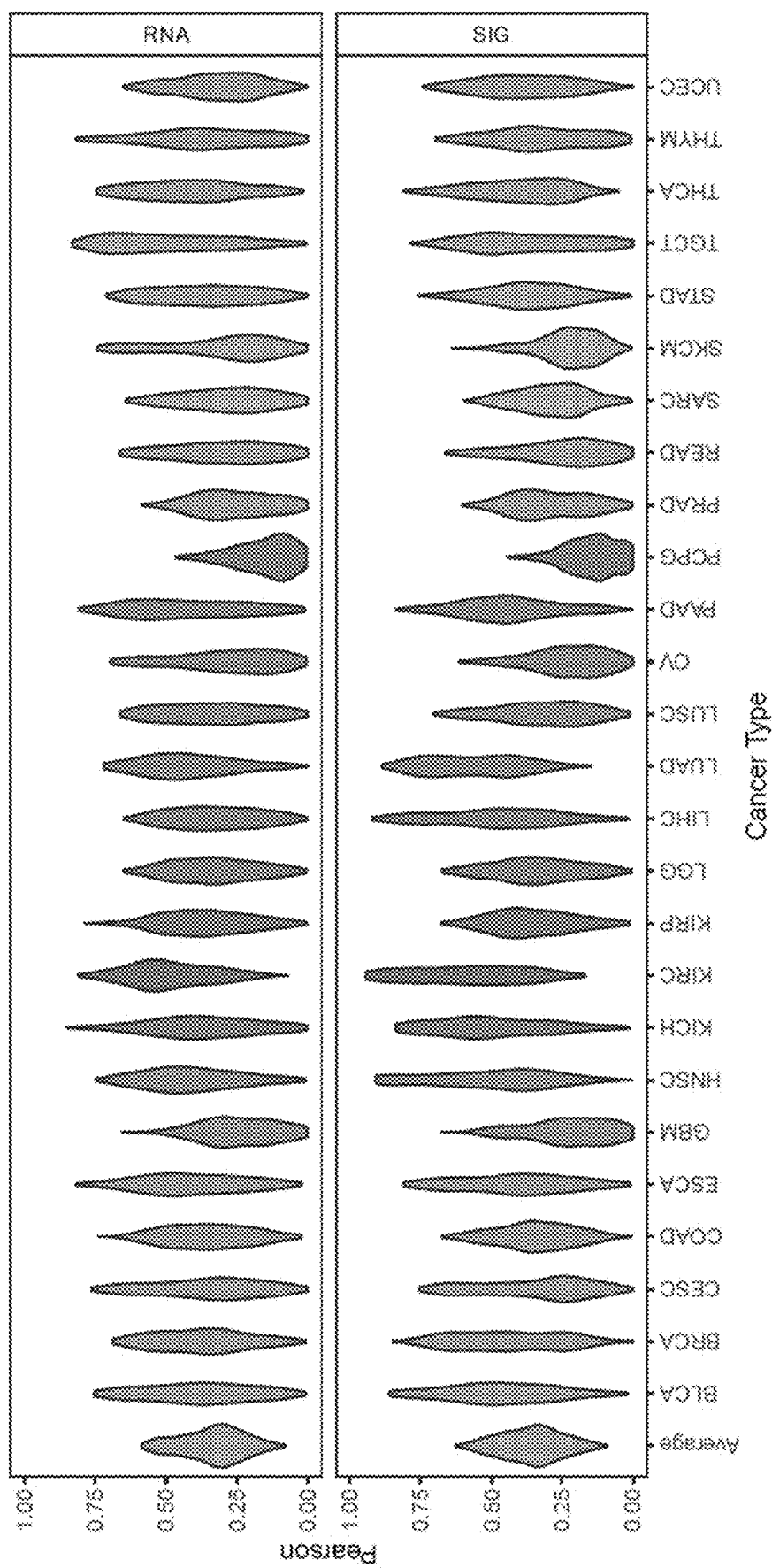
FIGS. 44A and 44B illustrate cross-modality comparison of continuous digital biomarker prediction quality, stratified by cancer-type in accordance with some embodiments.
Figure 44B:
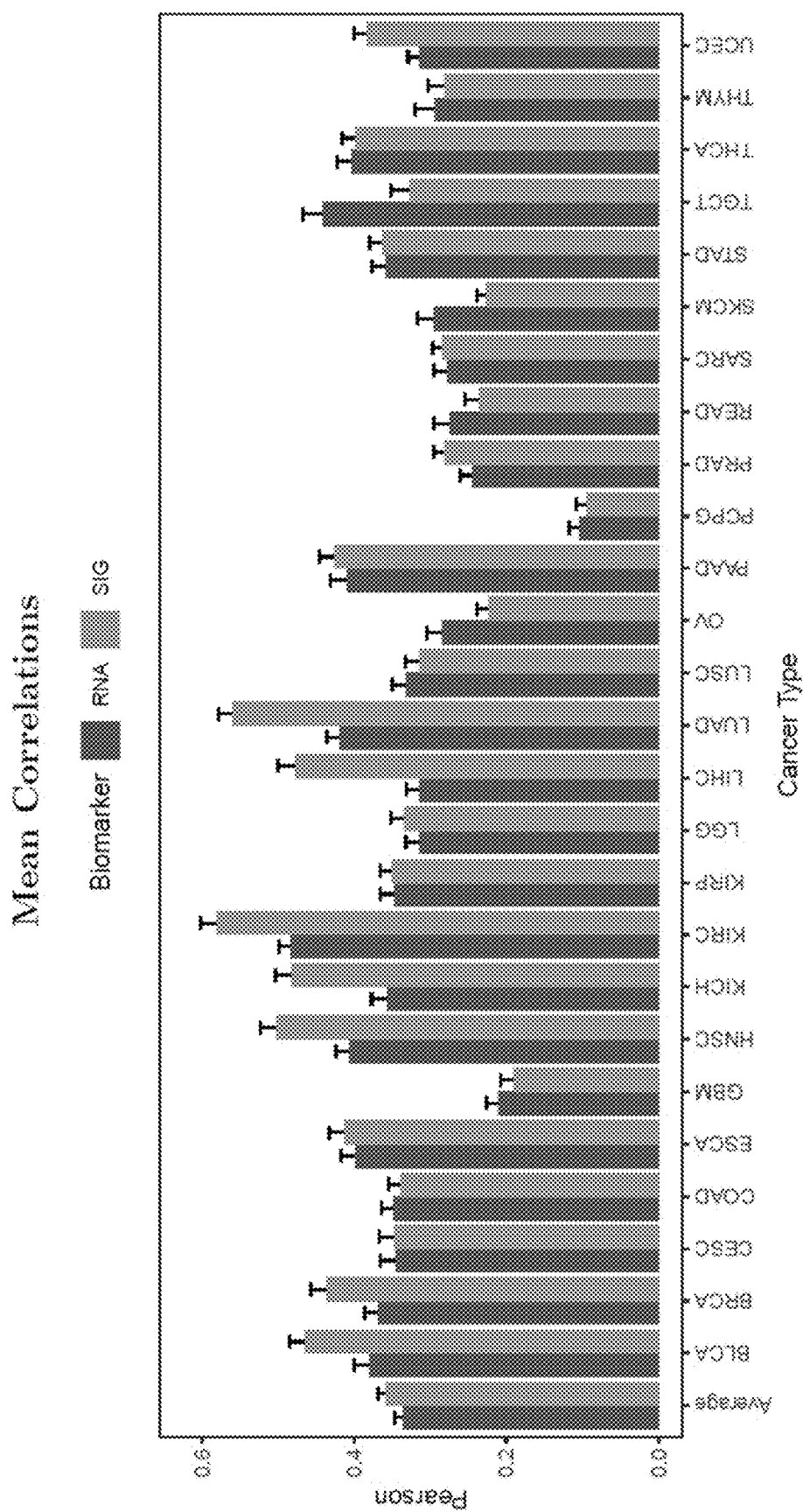

FIGS. 44A and 44B illustrate Cross-modality comparison of continuous digital biomarker prediction quality, stratified by cancer-type. Performance was evaluated at the patient level in a held-out evaluation set and averaged across 8 cross-validation folds. Metrics are calculated separately in each cancer type with ≥100 patients. The distributions are shown across up to 352 target genes. For RNA, the task is to predict the normalized log 2 expression level. For SIG, the task is to predict the min-max normalized amplification signature.

Figure 45:
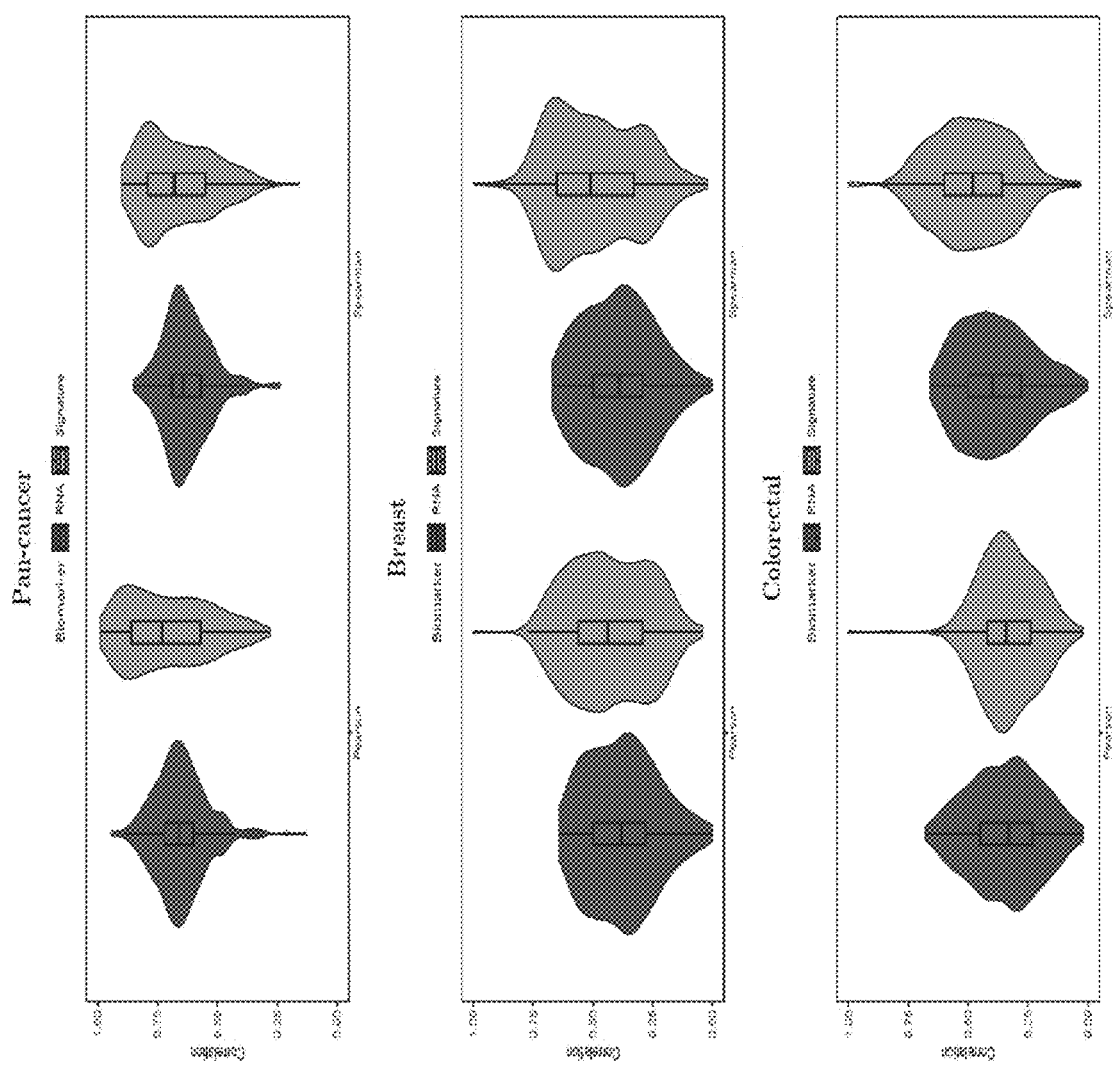
FIG. 45 illustrates performance on a regression task, across biomarkers, pan-cancer and for two specific cancer types in accordance with some embodiments.

FIG. 45 illustrates performance on a regression task, across biomarkers, pan-cancer and for two specific cancer types. The task was to predict the continuous expression level or amplification signature score. Performance was evaluated at the patient level in a held-out evaluation set and averaged across 8 cross-validation folds. Distributions are shown across up to 352 target genes.

Figure 46:
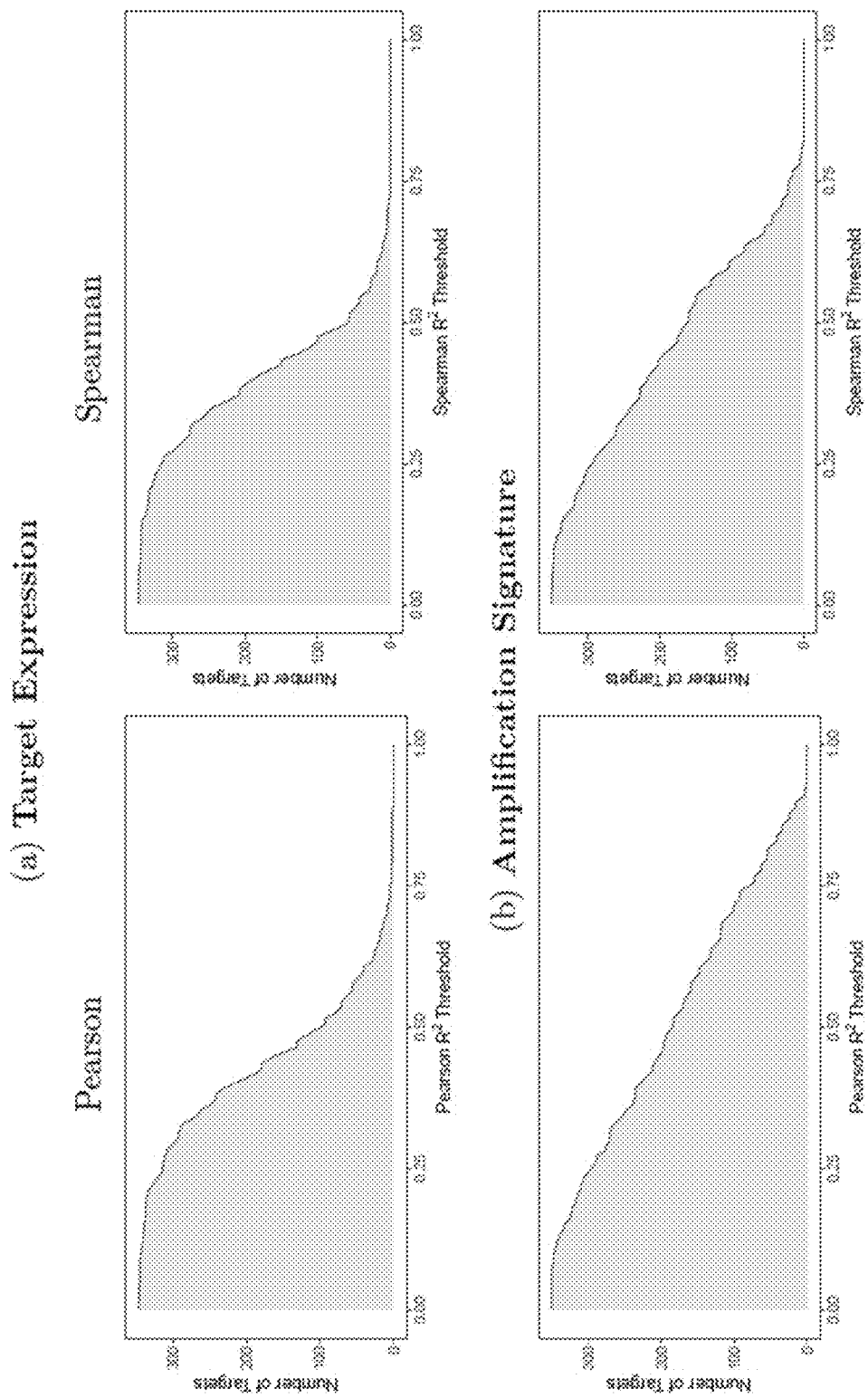
FIG. 46 illustrates a count of targets with Pearson and Spearman R2 exceeding a given threshold for the pan-cancer regression task in accordance with some embodiments.

FIG. 46 illustrates a count of targets with Pearson and Spearman R2 exceeding a given threshold for the pan-cancer regression task. Performance was evaluated at the patient level in a held-out evaluation set and averaged across 8 cross-validation folds. Pearson and Spearman are calculated pan-cancer.

Figure 47:
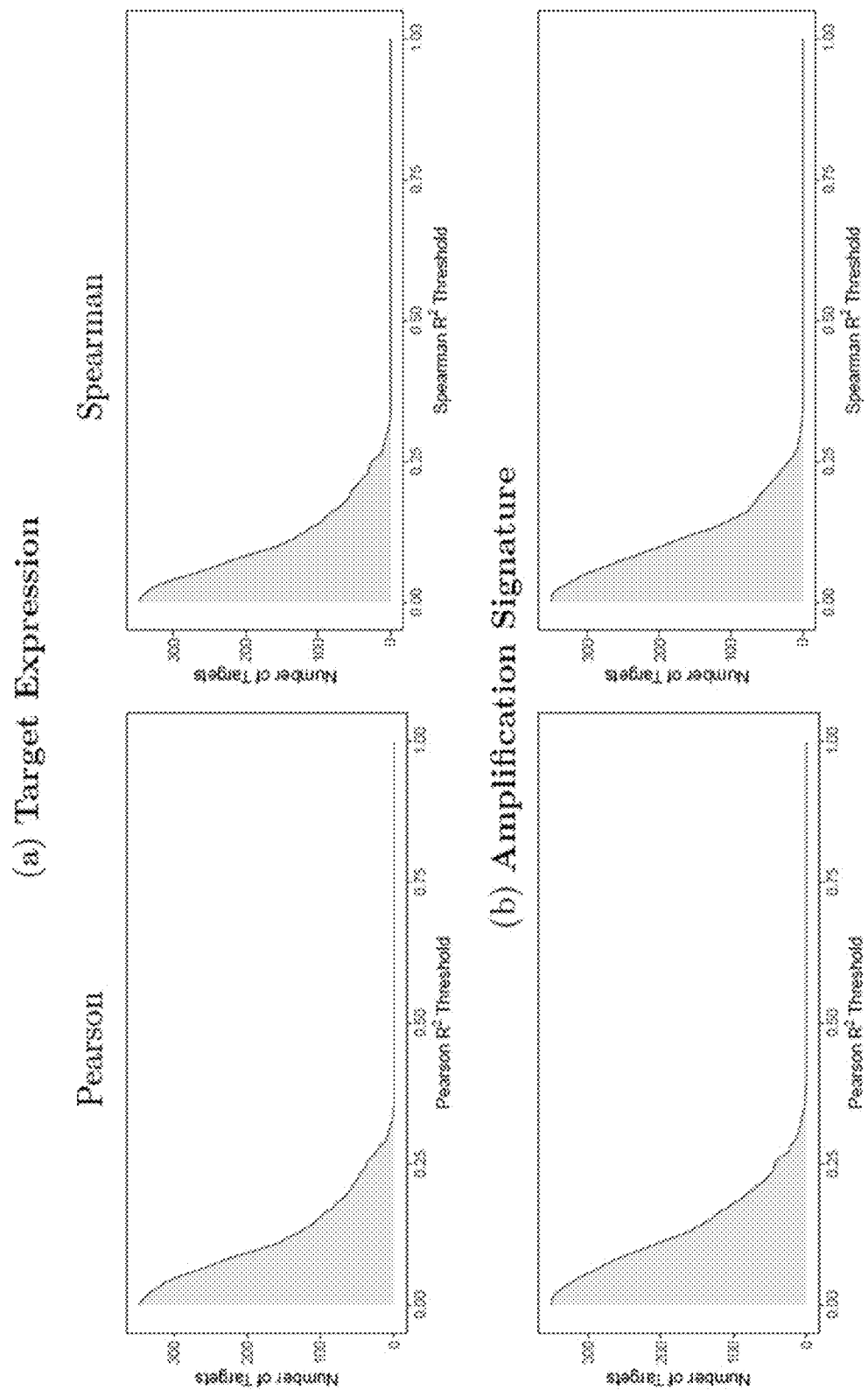
FIG. 47 illustrates a count of targets with Pearson and Spearman R2 exceeding a given threshold for the stratified regression task in accordance with some embodiments.

FIG. 47 illustrates a count of targets with Pearson and Spearman R2 exceeding a given threshold for the stratified regression task. Performance was evaluated at the patient level in a held-out evaluation set and averaged across 8 cross-validation folds. Pearson and Spearman are calculated separately in each cancer type with ≥100 patients, then averaged across cancer types.

Figure 48A:
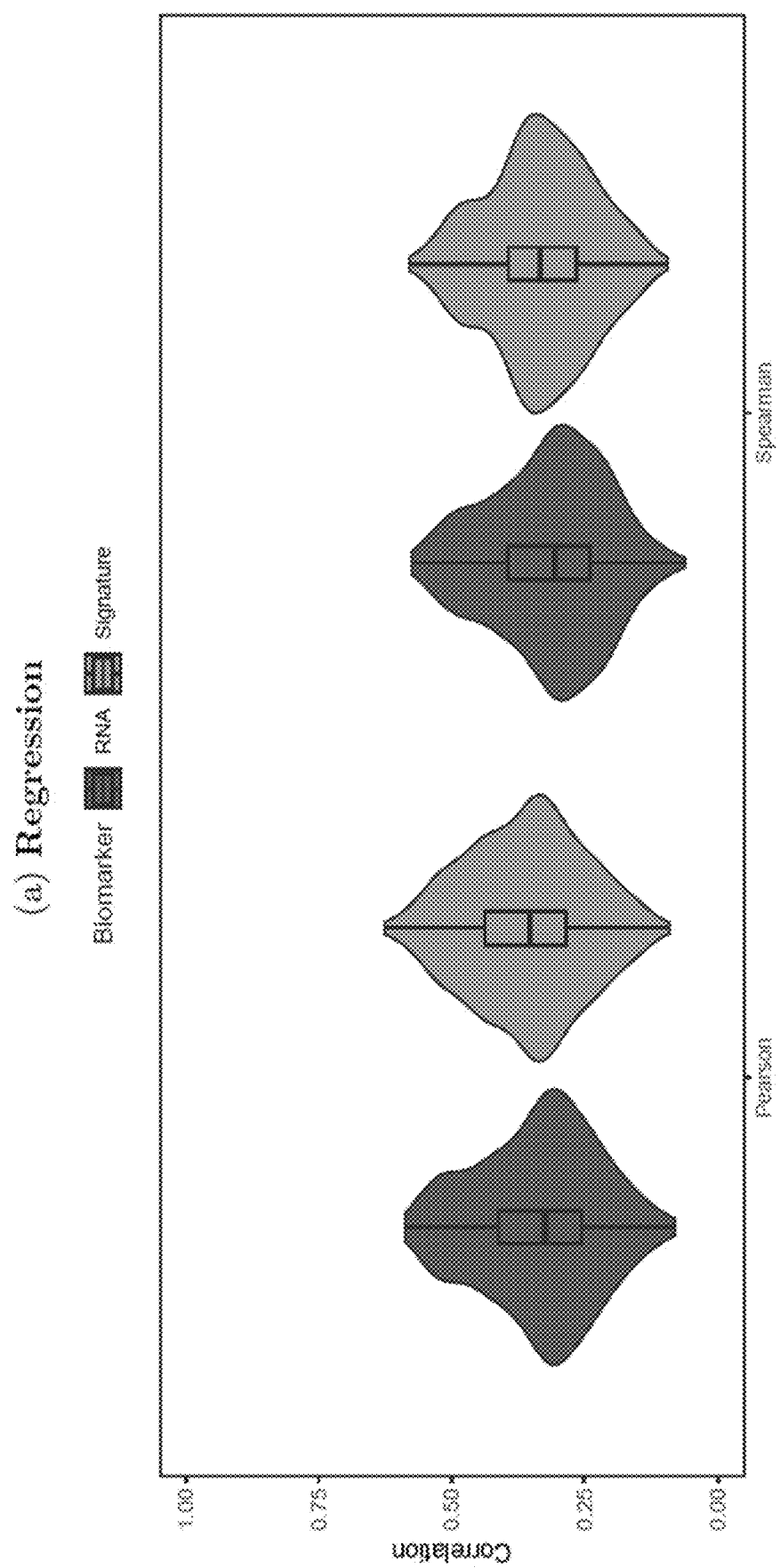
FIGS. 48A and 48B illustrate cross-modality comparison of digital biomarker prediction quality, stratified by cancer-type in accordance with some embodiments.
Figure 48B:
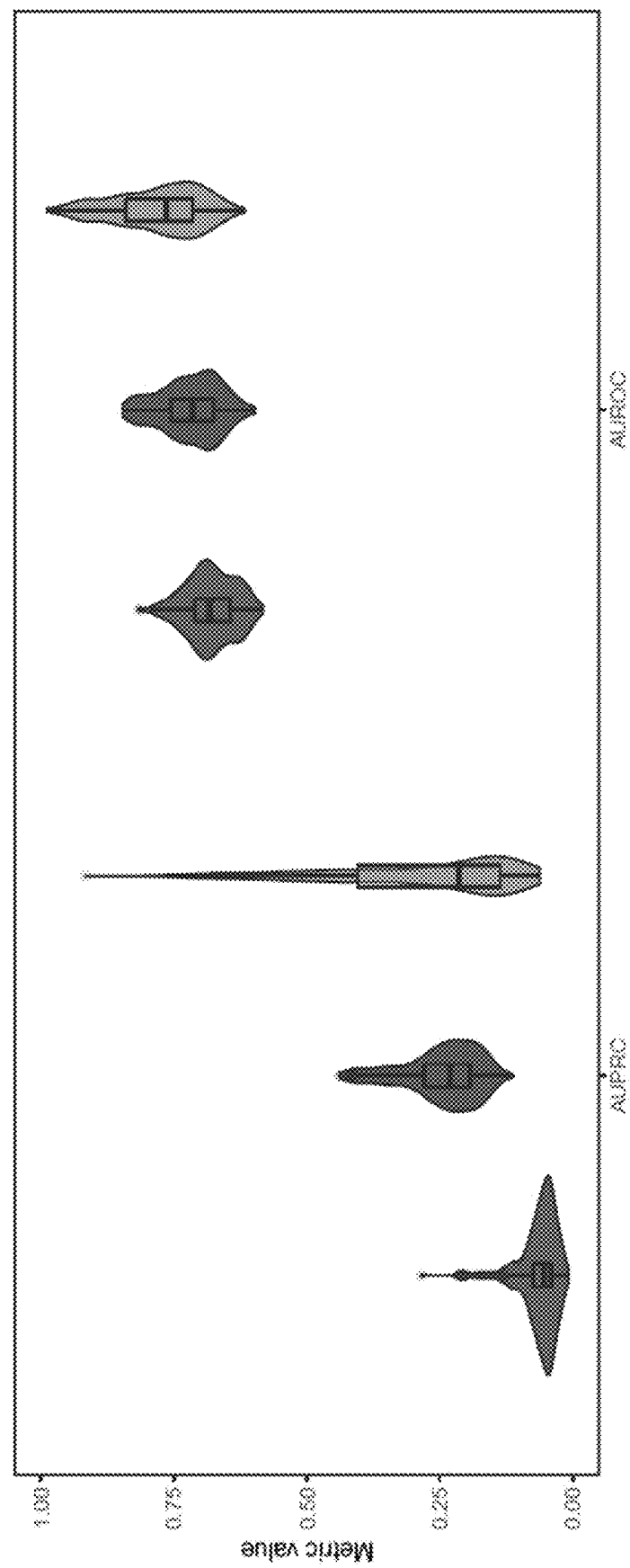

FIGS. 48A and 48B illustrate cross-modality comparison of digital biomarker prediction quality, stratified by cancer-type. Performance was evaluated at the patient level in a held-out evaluation set and averaged across 8 cross-validation folds. Metrics are calculated separately in each cancer type with ≥100 patients, then averaged across cancer types. The distributions are shown across up to 352 target genes. FIG. 48A show prediction of continuous target expression (RNA) and amplification signature levels. FIG. 48B shows prediction of binary copy number amplification (CNA) status or being in the upper 5th percentile (RNA & signature). RNA expression is measured as log 2 transcripts per million. Amplification signatures are based on those genes differentially expressed in patients with and without amplification.

Figure 49:
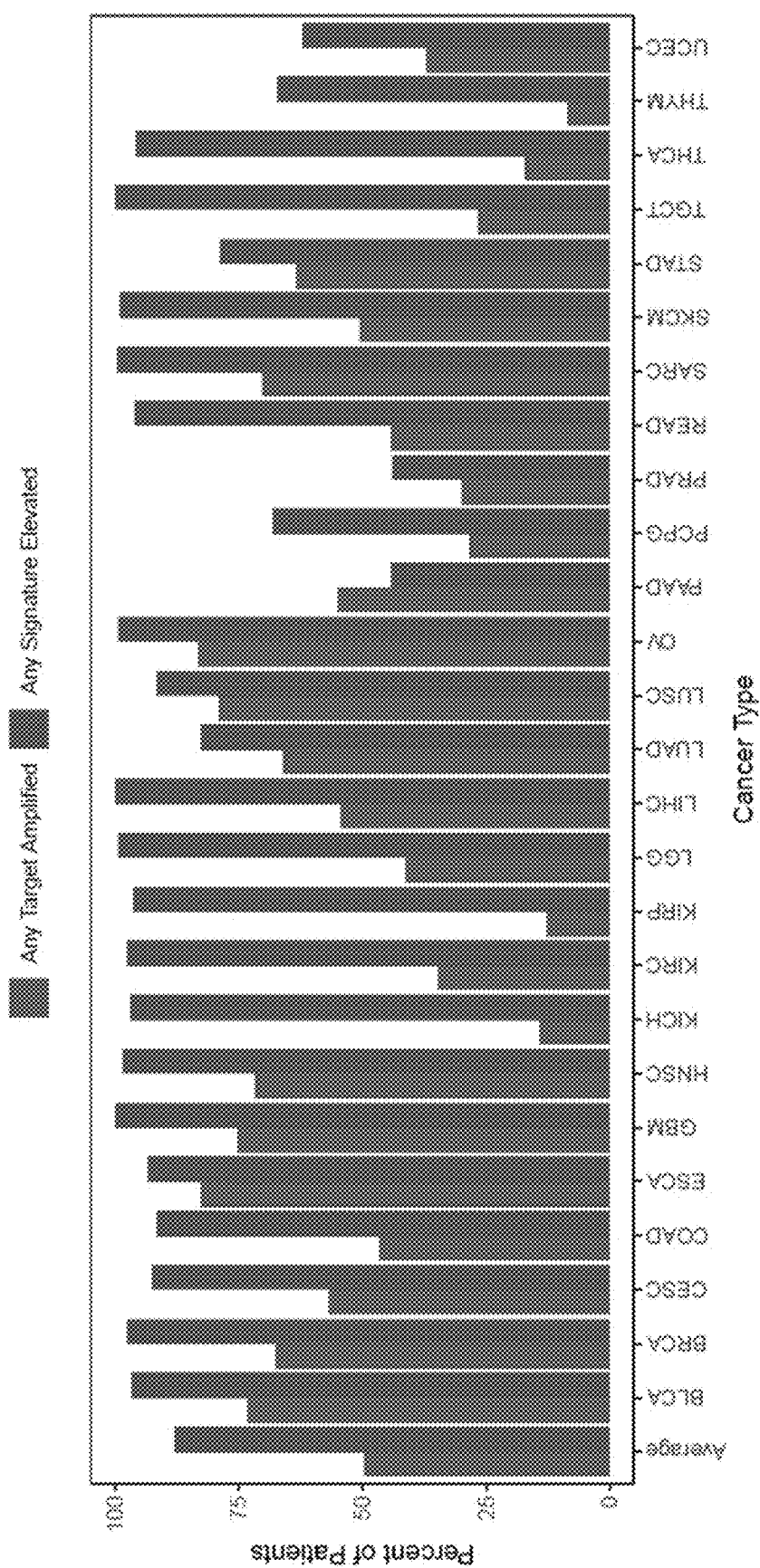
FIG. 49 illustrates prevalence of any target amplified versus any amplification signature elevated stratified by cancer type in accordance with some embodiments.

FIG. 49 illustrates prevalence of any target amplified versus any amplification signature elevated stratified by cancer type. Prevalence is calculated at the patient-level across up to 352 target genes. A patient was considered to have an elevated amplification signature if their score exceeded the 95th percentile for a given target.

Figure 50:
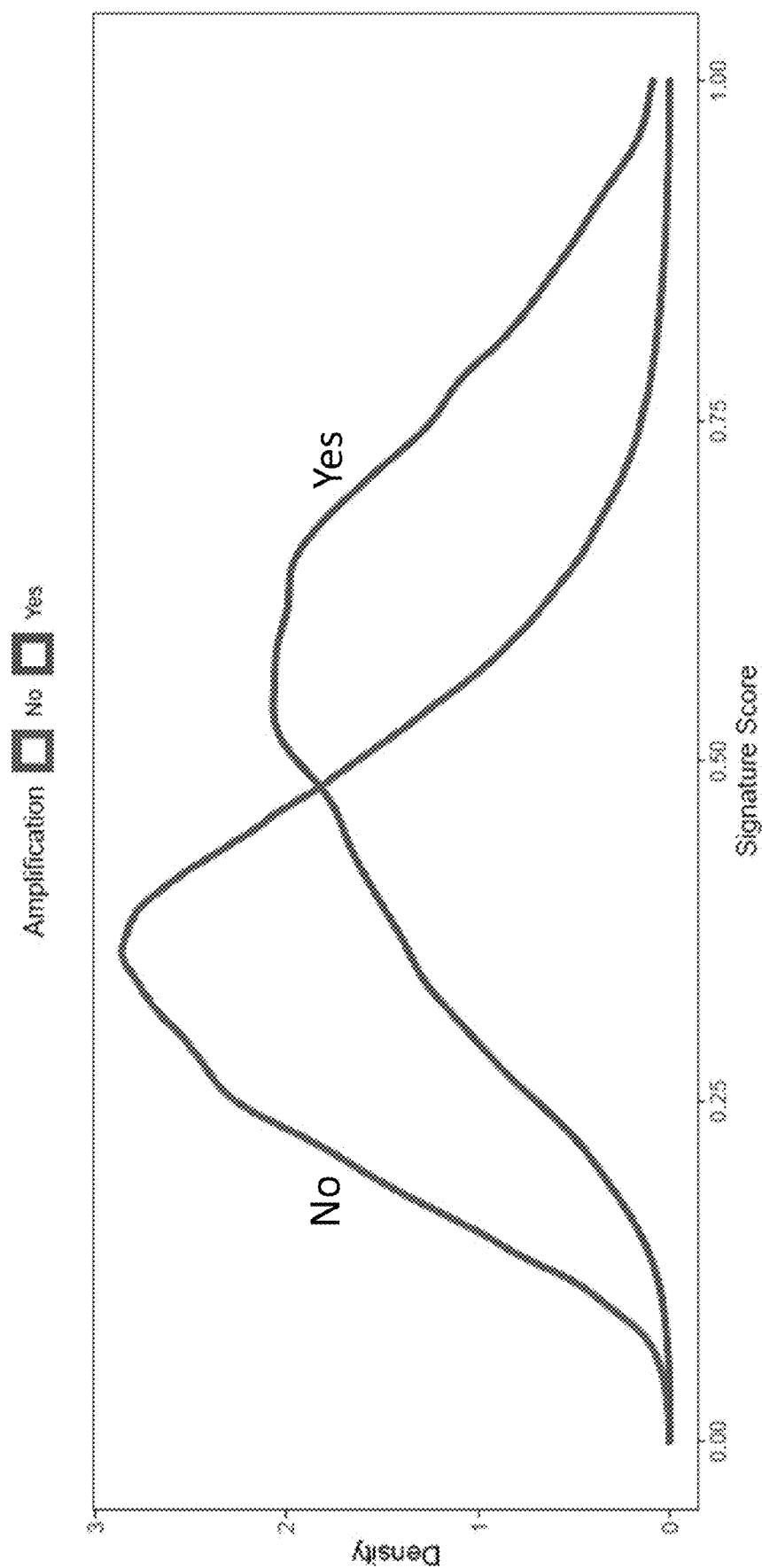
FIG. 50 illustrates signature distribution by patient amplification status. Shown is the average distribution across up to 351 amplification signatures in accordance with some embodiments.
Figure 51:
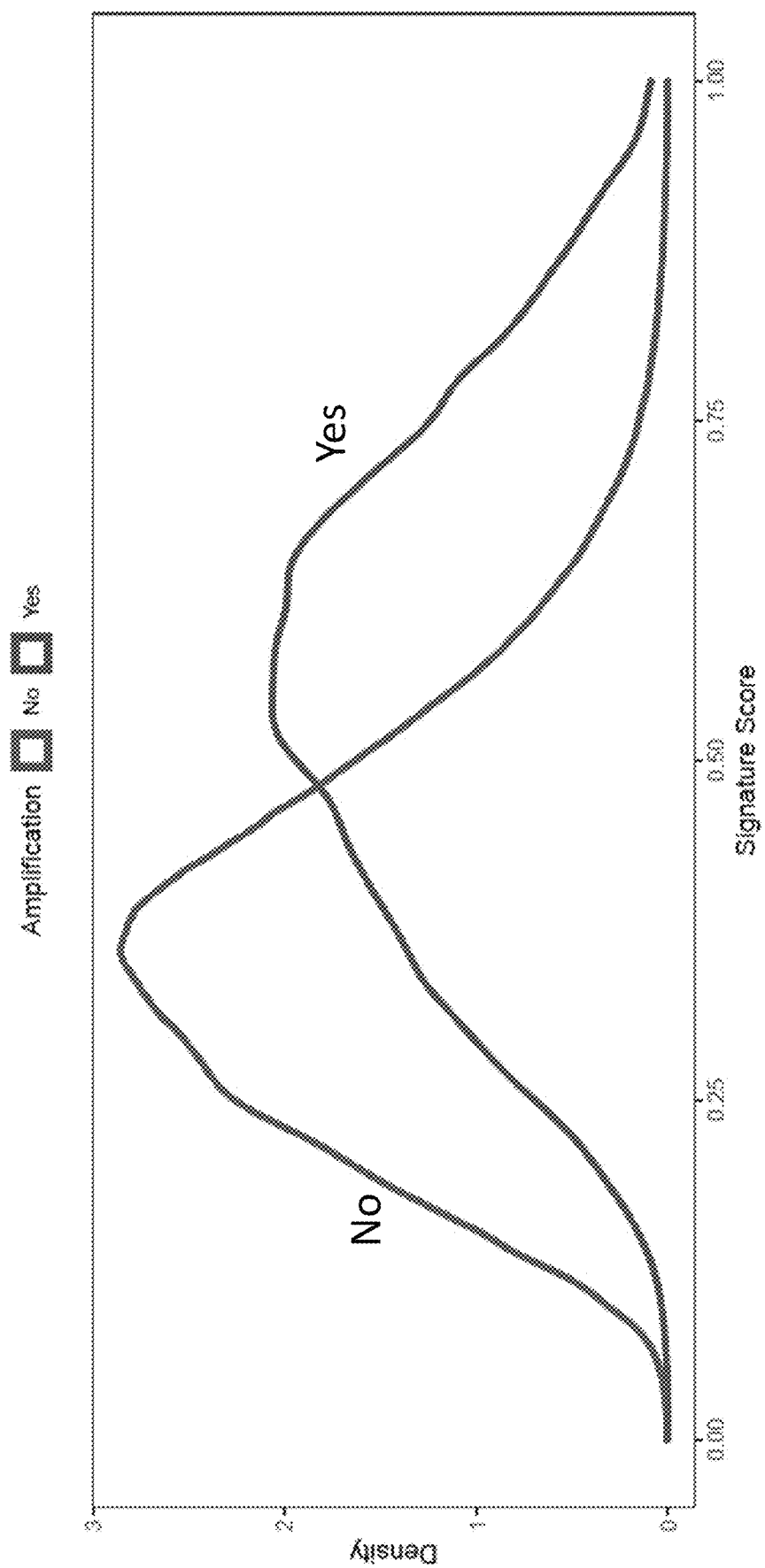
FIG. 51 illustrates distribution of correlations between amplification signatures and expression of the amplified gene pan-cancer in accordance with some embodiments.

FIG. 50 illustrates signature distribution by patient amplification status. Shown is the average distribution across up to 351 amplification signatures. FIG. 51 illustrates distribution of correlations between amplification signatures and expression of the amplified gene pan-cancer. For each of 352 targets, the correlation is calculated across 14K subjects. Shown are the distributions of the 352 correlations.

FIG. 52 illustrates squared correlation between the amplification signature and expression of the amplified gene, stratified. Correlations are first calculated within cancer types, then the mean is taken across cancer types. Shown are summary statistics for up to 352 correlations.

The approach described herein enables derivation of full molecular profiles from routinely collected histopathology images, defining a "semi-synthetic" cohort where imputed molecular data, inferred from real H&E, complements other measured covariates, including patient demographics, medical histories, treatments, and clinical outcomes. Given the abundance of cohorts that comprise H&E alongside these other covariates, one can produce a very large semi-synthetic cohort that is highly powered for a broad set of exploratory analyses. Specifically, diverse multi-modal biomarkers can be explored and even constructed, assessments can be performed as described herein to determined which are well-predicted, and associations with clinically relevant covariates (such as CNAs, survival, or treatment response) can be determined.

In addition to identifying biomarkers for a given target within a select tumor type, the approach described herein also enables the identification of potential new therapeutic opportunities. Specifically, the pan-cancer results described herein demonstrate an ability to accurately impute expression levels across multiple cancers from very diverse tissues of origin. These predictions can help highlight cancers where a cancer target is significantly expressed, at a level that might be therapeutically relevant (as compared with other cancers where that MOA is deployed). This may suggest new opportunities to expand the set of indications for a given targeted drug. While these insights could potentially be derived from molecular data collected across tumor types, such data are not regularly collected as part of the standard of care, making it difficult to detect those opportunities, especially for rare cancers and/or smaller patient subpopulations. In cases where clinical outcomes in response to treatment are available, associations between a signature (e.g., amplification signature) and these outcomes can be evaluated. As demonstrated in a preliminary analysis on cabozantinib response described below in the Exemplary Studies section, these associations could potentially inform an understanding of which aspect of the drug's MOA is driving efficacy, and hence suggest potential avenues for generating improved chemical matter. The preliminary results from the cabozantinib case study demonstrate the potential for a machine-learning defined signature to be predictive of superior clinical outcomes for a specific targeted therapy without requiring training on any response or outcome data for that drug.

In summary, this approach enables the use of the H&E images that are ubiquitously collected to identify patients that are likely to benefit from targeted therapies. This capability can be deployed in a variety of ways. For instance, it can be used as a rapid triage step for suggesting a set of therapeutic interventions that might be relevant to a patient; this step could be followed by the deployment of other, more standard, biomarker assay(s) such as genetic sequencing or IHC, to verify that the patient is indeed eligible for the drug, given the currently approved label. Such ML-based H&E biomarkers could be deployed rapidly, across geographies, and without specialized equipment or reagents beyond H&E staining and scanning, making them accessible on a broad scale. As another example, the techniques described herein may allow for direct use of an individual patient's H&E-derived biomarkers to identify and prescribe therapeutic interventions. Unlike most other biomarkers, which generally focus on one or two molecular measurements, the H&E biomarkers described herein rely on the full context of whole-slide images, which provide a broad, detailed, multi-scale phenotype. As such, they may detect more diffuse slide-level evidence that better captures coherent groups of patients that may have similar outcomes on treatment. This analysis might help identify patients who are unlikely to benefit, enabling a clinician to suggest a different course of treatment. Additionally, new patients might be identified. Indeed, the sets of patients at the higher end (95th percentile) of the RNA (expression) and amplification signature biomarkers are considerably larger than those defined by CNAs directly; thus, the expression and amplification signature biomarkers could help expand the population of patients who might benefit from a drug. Notably, this approach is generalizable across a broad set of targeted therapies.

The foregoing description, for the purpose of explanation, has been described with reference to specific examples or aspects. However, the illustrative discussions above are not intended to be exhaustive or to limit the invention to the precise forms disclosed. For the purpose of clarity and a concise description, features are described herein as part of the same or separate variations; however, it will be appreciated that the scope of the disclosure includes variations having combinations of all or some of the features described. Many modifications and variations are possible in view of the above teachings. The variations were chosen and described in order to best explain the principles of the techniques and their practical applications. Others skilled in the art are thereby enabled to best utilize the techniques and various variations with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

What is claimed is:

1. A system for predicting activity of a molecular analyte of a patient, comprising:
   one or more processors;
   a memory; and
   one or more programs, wherein the one or more programs are stored in the memory and configured to be executed by the one or more processors, the one or more programs including instructions for:
      training a first module of a machine learning model based on a plurality of medical images of a first cohort, wherein the first module comprises an embedding module;
      training a second module of the machine learning model based on one or more molecular analyte data sets obtained from a second cohort, wherein the second module comprises one or more heads;
      receiving a medical image from the patient;
      inputting the medical image from the patient into the first module of the machine learning model to obtain an embedding; and
      predicting, using the embedding and the trained second module of the machine learning model, the activity of the molecular analyte from the medical image of the patient.

2. The system of claim 1, wherein the predicted activity of the molecular analyte comprises amplification signature data and/or a chromosome accessibility score comprising an ATAC-seq peak value.

3. The system of claim 2, wherein the amplification signature data is generated based on a plurality of differentially expressed genes with respect to an amplification and a plurality of weights.

4. The system of claim 1, the one or more programs further including instructions for:
   training a third module of the machine learning model based on a third cohort, the third cohort comprising a plurality of medical images and associated clinical outcomes, wherein the third module of the machine learning model is configured to predict a therapeutic and/or clinical outcome.

5. The system of claim 4, the one or more programs further including instructions for: using the third machine learning model to determine a measure of significance or prognostic value of the molecular analyte to dynamically select a subset of molecular analytes for subsequent use.

6. The system of claim 5, wherein the patient is a first patient, the method further comprising:
predicting, using the trained first and second module of the machine learning model, activity of at least one of the subset of molecular analytes from a medical image of a second patient,
identifying, based on the predicted activity, an Antibody-Drug Conjugate (ADC) therapy for the second patient.

7. The system of claim 4, wherein the second module of the machine learning model and/or the third module of the machine learning model are trained using transfer learning.

8. The system of claim 4, wherein the third cohort comprises a plurality of medical images and associated clinical outcomes.

9. The system of claim 4, wherein the first, second or third cohort further comprise one or more clinical covariates.

10. The system of claim 9, wherein the one or more clinical covariates comprise patient gender, patient age, height, weight, patient diagnosis, patient histology data, patient radiology data, patient medical history, or any combination thereof.

11. The system of claim 4, the one or more programs further including instructions for removing data-specific biases in the first, second, and third cohort.

12. The system of claim 1, wherein the one or more molecular analyte data sets comprises:
gene expression data;
copy number amplification (CNA) data;
chromatin accessibility data;
DNA methylation data;
histone modification;
RNA data;
protein data;
spatial biology data;
whole-genome sequencing (WGS) data;
somatic mutation data;
germline mutation data; or
any combination thereof.

13. The system of claim 12, wherein the one or more molecular analyte data sets comprise:
a gene expression value comprising an abundance of a transcript;
a copy number amplification value;
an amplification signature value;
abundance of one or more histone modifications comprising a ChIP-seq value;
abundance of one or more mRNA sequences;
abundance of one or more proteins;
the presence of one or more somatic mutations;
the presence of one or more germline mutations;
the presence or absence of one or more specific DNA methylation marks in one or more specific genomic regions,
or any combination thereof.

14. The system of claim 1, wherein the medical image from the patient is obtained from a fourth cohort comprising a plurality of medical images of a plurality of patients and optionally one or more associated molecular analyte data sets for each of the plurality of medical images.

15. The system of claim 14, the one or more programs further including instructions for determining for each of the patients of the fourth cohort that the patient belongs to one or more subgroups.

16. The system of claim 1, wherein the first cohort comprises a plurality of medical images from a plurality of patients.

17. The system of claim 16, wherein the plurality of medical images comprises:
one or more histopathology images;
one or more magnetic resonance imaging (MRI) images;
one or more computerized tomography (CT) scans; or
any combination thereof.

18. The system of claim 16, wherein the plurality of medical images are unlabeled and the first module is trained using unsupervised learning.

19. The system of claim 1, wherein the first cohort and second cohort are the same cohort.

20. The system of claim 1, the one or more programs further including instructions for:
receiving a medical image of a new patient;
obtaining an embedding by providing the medical image of the new patient to the first module;
mapping the embedding based on domain adaptation.

21. The system of claim 1, wherein the molecular analyte is a first molecular analyte, the one or more programs further including instructions for:
training a fourth module of the machine learning model based on the second module using transfer learning, wherein the fourth module is configured to predict a second molecular analyte related to the first molecular analyte.

22. The system of claim 1, wherein training the second module of the machine learning model comprises:
in a first stage, training a generalized module based on training data from the one or more molecular analyte data sets obtained from the second cohort; and
in a second stage, finetuning the generalized module based on a subset of the training data to obtain the second module.

23. The system of claim 22, wherein the subset of training data corresponds to a patient attribute.

24. The system of claim 23, wherein the patient attribute comprises a patient cohort, a disease, a biomarker, or any combination thereof.

25. The system of claim 23, wherein the patient has the patient attribute.

26. The system of claim 1, wherein the first module of the machine learning model is trained to generate tile-level embeddings based on a plurality of tiles of the medical image, and wherein the tile-level embeddings are input into the second module of the machine learning model.

27. The system of claim 1, the one or more programs further including instructions for:
generating an annotation map of the predicted activity of the molecular analyte; and
overlaying the annotation map on the medical image.

28. A method for predicting activity of a molecular analyte of a patient, comprising:
training a first module of a machine learning model based on a plurality of medical images of a first cohort, wherein the first module comprises an embedding module;
training a second module of the machine learning model based on one or more molecular analyte data sets obtained from a second cohort, wherein the second module comprises one or more heads;

receiving a medical image from the patient;
inputting the medical image from the patient into the first module of the machine learning model to obtain an embedding; and
predicting, using the embedding and the trained second module of the machine learning model, the activity of the molecular analyte from the medical image of the patient.

29. A non-transitory computer-readable storage medium storing one or more programs for predicting activity of a molecular analyte of a patient, the one or more programs comprising instructions, which when executed by one or more processors of an electronic device, cause the electronic device to perform:
training a first module of a machine learning model based on a plurality of medical images of a first cohort, wherein the first module comprises an embedding module;
training a second module of the machine learning model based on one or more molecular analyte data sets obtained from a second cohort, wherein the second module comprises one or more heads;
receiving a medical image from the patient;
inputting the medical image from the patient into the first module of the machine learning model to obtain an embedding; and
predicting, using the embedding and the trained second module of the machine learning model, the activity of the molecular analyte from the medical image of the patient.

* * * * *